US012414995B2

United States Patent
Wan et al.

(10) Patent No.: US 12,414,995 B2
(45) Date of Patent: Sep. 16, 2025

(54) BIFUNCTIONAL COMPOUNDS COMPRISING APCIN-A AND THEIR USE IN THE TREATMENT OF CANCER

(71) Applicant: Northwestern University, Evanston, IL (US)

(72) Inventors: Yong Wan, Evanston, IL (US); Zhuan Zhou, Evanston, IL (US); Junlong Chi, Evanston, IL (US); Gary Schiltz, Evanston, IL (US)

(73) Assignee: Northwestern University, Evanston, IL (US)

( * ) Notice: Subject to any disclaimer, the term of this patent is extended or adjusted under 35 U.S.C. 154(b) by 944 days.

(21) Appl. No.: 17/603,876

(22) PCT Filed: Apr. 14, 2020

(86) PCT No.: PCT/US2020/028061
§ 371 (c)(1),
(2) Date: Oct. 14, 2021

(87) PCT Pub. No.: WO2020/214555
PCT Pub. Date: Oct. 22, 2020

(65) Prior Publication Data
US 2022/0241424 A1    Aug. 4, 2022

Related U.S. Application Data

(60) Provisional application No. 62/834,550, filed on Apr. 16, 2019.

(51) Int. Cl.
*A61K 47/55*     (2017.01)
*A61K 31/138*    (2006.01)
*A61K 31/337*    (2006.01)
*A61K 31/506*    (2006.01)
*A61K 47/54*     (2017.01)
*A61P 35/00*     (2006.01)

(52) U.S. Cl.
CPC ............ *A61K 47/55* (2017.08); *A61K 31/138* (2013.01); *A61K 31/337* (2013.01); *A61K 31/506* (2013.01); *A61K 47/54* (2017.08); *A61K 47/545* (2017.08); *A61P 35/00* (2018.01)

(58) Field of Classification Search
CPC ........ A61K 31/506; A61K 47/55; A61P 35/00
See application file for complete search history.

(56) References Cited

U.S. PATENT DOCUMENTS

2015/0328214 A1*  11/2015  King ................... A61K 31/436
                                                          435/375
2018/0215731 A1*  8/2018  Crew .................... A61K 47/55

FOREIGN PATENT DOCUMENTS

WO    WO-2018/144649 A1    8/2018

OTHER PUBLICATIONS

Chi et al., "A novel strategy to block mitotic progression for targeted therapy," Ebiomedicine, Oct. 25, 2019, 49:40-54.
International Search Report and Written Opinion dated Jul. 15, 2020 in PCT/US2020/028061.
Ottis et al., "Assessing Different E3 Ligases for Small Molecule Induced Protein Ubiquitination and Degradation," ACS Chemical Biology, Sep. 5, 2017, 12(10):2570-2578.
Sackton et al., "Synergistic blockade of mitotic exit by two chemical inhibitors of the APC/C," Nature, Aug. 24, 2014, 514(7524):646-649.
Wang et al., "Proteolysis Targeting Chimera (PROTAC): A Paradigm-Shifting Approach in Small Molecule Drug Discovery," Current Topics in Medicinal Chemistry, Nov. 26, 2018, 18(16):1354-1356.
Wang et al., "Targeting Cdc20 as a novel cancer therapeutic strategy," Pharmacology and Therapeutics, Apr. 4, 2015, 151:141-151.

* cited by examiner

*Primary Examiner* — Theodore R. Howell
(74) *Attorney, Agent, or Firm* — Foley & Lardner LLP

(57) ABSTRACT

Described herein are compounds of Formula I, or their pharmaceutically acceptable salts thereof, compositions comprising the same, and methods of using such compounds or compositions in inducing Cdc20 degradation in a cell, blocking mitotic progression, inhibiting tumor proliferation, treating cancer, and/or re-sensitizing a subject to cancer treatment with tamoxifen.

17 Claims, 32 Drawing Sheets

BIFUNCTIONAL COMPOUNDS COMPRISING APCIN-A AND THEIR USE IN THE TREATMENT OF CANCER

CROSS-REFERENCE TO RELATED APPLICATIONS

This application is the U.S. National Stage of PCT/US2020/028061, filed Apr. 14, 2020, which claims the benefit of priority to U.S. Provisional Patent Application No. 62/834,550, filed on Apr. 16, 2019, the contents of which are incorporated by reference herein in their entirety.

FIELD

The present invention relates generally to the field of cancer treatment. More specifically, the present invention involves targeting the Cdc20-APC/C pathway for cancer treatment.

SUMMARY

Provided herein, in one aspect, are compounds of Formula I, or a pharmaceutically acceptable salt or ester thereof:

X-L-Y (Formula I)

wherein X is a cell-division cycle protein 20 (Cdc20) binding moiety; Y is an E3 ubiquitin ligase binding moiety; and L is a linker covalently attached to X and Y or a bond between X and Y. In some embodiments, X comprises a moiety selected from the group consisting of Apcin and Apcin-A, or a derivative thereof. In some embodiments, X comprises:

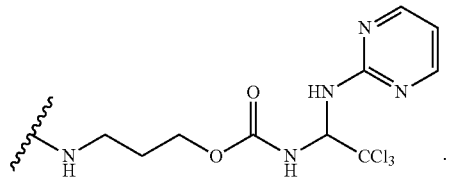

In some embodiments, Y is a moiety that binds an E3 ubiquitin ligase selected from the group consisting of Von Hippel-Lindau (VHL) E3 ubiquitin ligase, cereblon (CRBN), IAP, and MDM2. In some embodiments, Y comprises a moiety selected from:

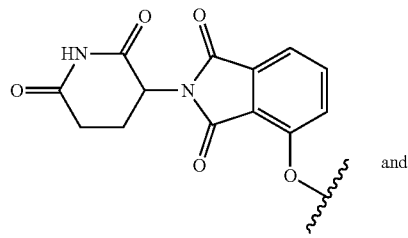

and

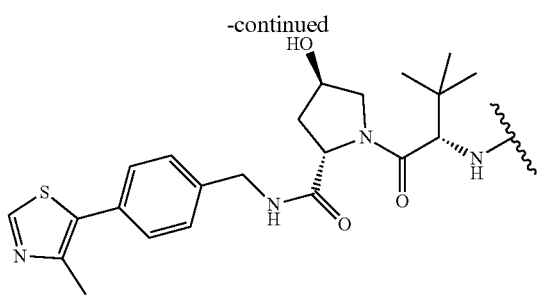

In some embodiments, L comprises:

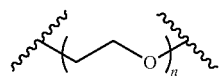

wherein n is an integer greater than or equal to 2. In some embodiments, L is selected from the group consisting of:

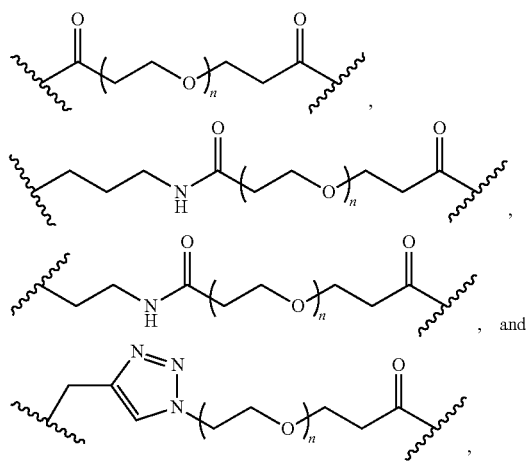

wherein n is an integer greater than or equal to 2.

Provided herein, in another aspect, are compositions comprising an effective amount of a compound of Formula I. In some embodiments, the composition further comprises at least one additional active agent. In some embodiments, the at least one additional active agent is an anti-cancer agent.

Provided herein, in another aspect, are methods of treating cancer in a subject in need thereof, the method comprising, consisting essentially of, or consisting of administering to the subject a therapeutically effective amount of a compound of Formula I or a composition comprising or consisting essentially of a compound of Formula I. In some embodiments, the cancer is breast cancer.

Provided herein, in another aspect, are methods of inducing Cdc20 degradation in a cell, the method comprising, consisting essentially of, or consisting of contacting the cell with an effective amount of a compound of Formula I or a composition comprising or consisting essentially of a compound of Formula I.

Provided herein, in another aspect, are methods of blocking mitotic progression in a subject, the method comprising, consisting essentially of, or consisting of administering to the subject a therapeutically effective amount of a compound of Formula I or a composition comprising or consisting essentially of a compound of Formula I.

Provided herein, in another aspect, are methods of inhibiting tumor proliferation in a subject, the method comprising, consisting essentially of, or consisting of administering to the subject a therapeutically effective amount of a compound of Formula I or a composition comprising or consisting essentially of a compound of Formula I.

Provided herein, in another aspect, are methods of re-sensitizing a subject to cancer treatment with tamoxifen, the method comprising, consisting essentially of, or consisting of administering to the subject a therapeutically effective amount of a compound of Formula I or a composition comprising or consisting essentially of a compound of Formula I, wherein the subject is resistant to treatment with tamoxifen prior to administration of the compound of Formula I or the composition comprising or consisting essentially of the compound of Formula I.

BRIEF DESCRIPTION OF THE DRAWINGS

(FIG. 13E) 0-40 ns, (FIG. 13F) 40-80 ns, (FIG. 13G) 80-120 ns, (FIG. 13H) 120-160 ns and (FIG. 13I) 160-200 ns. Up to 10 most frequent interactions are displayed in FIGS. 13A-13I. Seven top-ranking residue-residue interactions shown in FIG. 13I played a key role in stabilizing the final conformer. Results from run 4 are not shown since the apcin-A fragment of CP5V got detached from the D-box binding site of Cdc20. Stars indicate residue-residue interactions that were transiently stabilized during simulations.

DETAILED DESCRIPTION

Figure 1A:
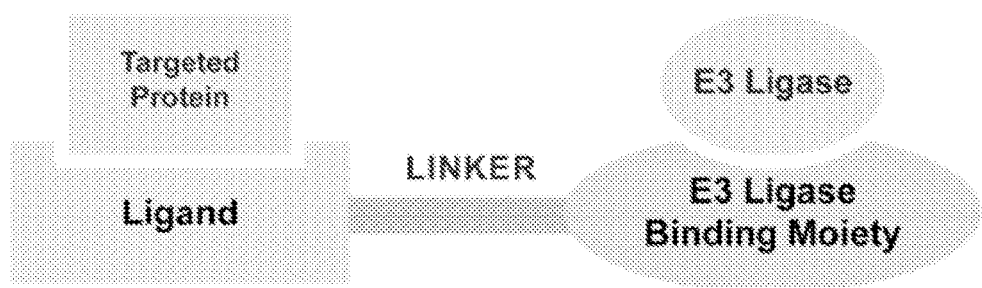
FIG. 1A shows a general structure of the compounds of the present disclosure.
Figure 1B:
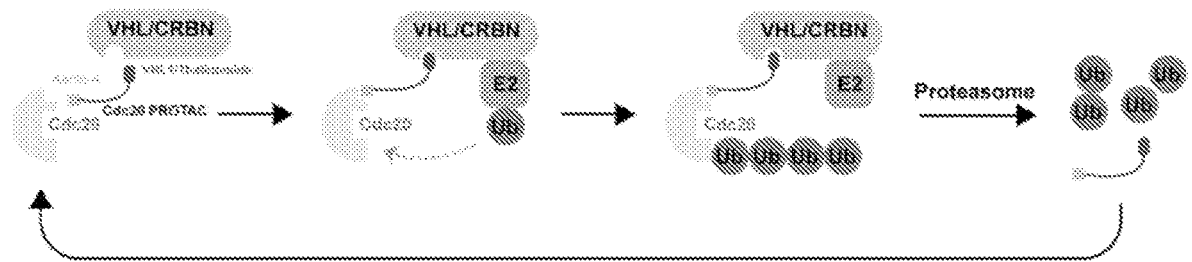
FIG. 1B shows a non-limiting example of the mechanism of action for some embodiments of the compounds of the present disclosure. More specifically, in these embodiments, Apcin-A is utilized as a Cdc20 targeting ligand, and VHL- or CRBN-binding moieties are used to recruit VHL/VBC complex or Celebron E3 ligase to the compound. A series of Polyethylene glycol (PEG) are used to link Apcin-A and the VHL- or CRBN-binding moiety.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Definitions

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "Apcin" is a compound of formula:

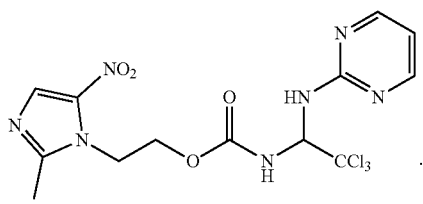

Apcin may be modified so as to be covalently bound to form a compound of the present disclosure. In some embodiments, Apcin is modified to provide a derivative that is covalently bound to form a compound of the present disclosure. One non-limiting example of an Apcin derivative is Apsin-A. Other non-limiting examples of such derivatives include compounds with pyrimidine replacement, pyrimidine substitution, elongation or truncation of the propyl linker between the primary amine and carbamate moieties, and substitution of the propyl linker between the primary amine and carbamate moieties, or any combination of two or more thereof. In some embodiments, the elongation of the propyl linker comprises, consists essentially of, or consists of the addition of one or more methylene groups.

As used herein, "Apcin-A" is a compound of formula:

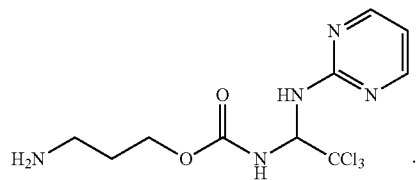

Apcin-A may be covalently bound at the primary amine position to form a compound of the present disclosure. In some embodiments, Apcin-A is modified to provide a derivative that is covalently bound to form a compound of the present disclosure. Non-limiting examples of such derivatives include compounds with pyrimidine replacement, pyrimidine substitution, elongation or truncation of the propyl linker between the primary amine and carbamate moieties, and substitution of the propyl linker between the primary amine and carbamate moieties, or any combination of two or more thereof. In some embodiments, the elongation of the propyl linker comprises, consists essentially of, or consists of the addition of one or more methylene groups.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

As used herein, "subject" refers to an animal, such as a mammal (including a human), that has been or will be the object of treatment, observation or experiment. "Subject" and "patient" may be used interchangeably, unless otherwise indicated. Mammals include, but are not limited to, mice, rodents, rats, simians, humans, farm animals, dogs, cats, sport animals, and pets. The methods described herein may be useful in human therapy and/or veterinary applications. In some embodiments, the subject is a mammal. In some embodiments, the subject is a human.

The terms "therapeutically effective amount" and "effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver.

The term "treatment" or "treating" means administering a compound disclosed herein for the purpose of: (i) delaying the onset of a disease, that is, causing the clinical symptoms of the disease not to develop or delaying the development thereof, (ii) inhibiting the disease, that is, arresting the development of clinical symptoms; and/or (iii) relieving the disease, that is, causing the regression of clinical symptoms or the severity thereof.

Unless defined otherwise, all technical and scientific terms used herein have the same meaning as commonly understood by one of ordinary skill in the art to which this present invention belongs. Although any methods and materials similar or equivalent to those described herein can also be used in the practice or testing of the present invention, representative illustrative methods and materials are described herein.

Cdc20-APC/C Pathway

The cell-division cycle protein 20 (Cdc20) is a substrate receptor of anaphase-promoting complex or cyclosome (APC/C), which orchestrates the initiation of anaphase and the exit from mitosis through time-dependent degradation of securin and cyclin B (Zur and Brandeis 2001; Wang, Zhang et al. 2015; Zhou, He et al. 2016). In addition to its mitotic function, the role of Cdc20-APC/C can be linked to a variety of cellular processes beyond cell cycle, including apoptosis, neurogenesis, stem cell expansion and epigenetic regulation (Wang, Zhang et al. 2015; Zhou, He et al. 2016; Kapanidou, Curtis et al. 2017). Malfunction of Cdc20-APC/C often results in chromosomal instability that could further lead to human diseases or dispose normal cells to become malignant (Wang, Zhang et al. 2015; Zhou, He et al. 2016). Results from TCGA and pathological analyses have revealed a strong connection between aberrant upregulation of Cdc20 with various types of cancers (Kato, Daigo et al. 2012; Ding, Wu et al. 2014; Karra, Repo et al. 2014). For instance, severe accumulation of Cdc20 has been detected in breast cancer cells and colon cancer cells compared to normal epithelial cells and adjacent normal tissues in cancer patient specimens (Harley, Allen et al. 2010; Wu, Hu et al. 2013; Karra, Repo et al. 2014). Immunohistochemistry analysis have further described the elevated Cdc20 and securin as the hallmark of a triple-negative breast cancer (TNBC) with a short survival time window for breast cancer patients (Karra, Repo et al. 2014). Moreover, Cdc20 upregulation has been associated with aggressive tumor progression and poor prognosis in gastric cancer (Ding, Wu et al. 2014) and primary non-small cell lung cancer (Kato, Daigo et al. 2012). Surprisingly, the increased expression of Cdc20 has been detected in metastatic liver tissue in patients with colorectal cancer (Vogtmann, Xiang et al. 2014). In addition, overexpression of Cdc20 has been measured with a high grade in bladder, cervical, colonic, endometrial, gastric, liver, ovarian, prostatic, and renal carcinomas (Schutte, Bisht et al. 2014). Thus, Cdc20 is thought to be to a potential biomarker and a possible target for cancer therapy.

Blockade of mitotic progression can induce mitotic catastrophe to kill cancer cells (Huang, Shi et al. 2009; Manchado, Guillamot et al. 2012; Agarwal and Varma 2017). The inhibition of several steps during mitosis, such as mitotic checkpoint, microtubule polymerization, chromatid segregation, cytokinesis and the exit from mitosis, have been considered for the development of anti-mitotic drugs (Manchado, Guillamot et al. 2012). A series of mitotic drug and mitotic inhibitors have been developed, including paclitaxel and inhibitors for Aurora kinase A/B, Cdk1, CENP-E, Eg5 and Polo-like kinase (Manchado, Guillamot et al. 2012).

Because of the important role of Cdc20-APC/C in controlling chromatid separation and the exit from mitosis, Cdc20-APC/C has been thought to be a pivotal target for drug development. The endeavor of screening for small molecule inhibitors in suppressing the activity for Cdc20-APC/C has led to the development of several APC inhibitors such as TAME, ProTAME, Apcin, and Apcin-A (Zeng, Sigoillot et al. 2010; Zeng and King 2012; Sackton, Dimova et al. 2014). While these APC inhibitors have shed light on how to efficiently block APC activation in the cell-free assay, some challenges, such as efficacy in inhibiting mitosis and suppressing cancer cell growth in vivo, limit their current potential for clinical translation.

Compounds

In one aspect, provided herein are bifunctional compounds which to recruit an endogenous ubiquitin protein ligase in order to induce ubiquitinylation of target proteins for destruction. These bifunctional compounds bind to a target protein with one end while the other end binds to an E3 ligase to form a ternary complex. The recruited E3 ligase then mediates the transfer of ubiquitin from an E2 enzyme to the target protein. The ternary complex subsequently dissociates, and the ubiquitinated target protein is removed by a proteasome.

In another aspect, the bifunctional compounds are compounds of Formula I, or a pharmaceutically acceptable salt thereof:

$$X-L-Y \quad \text{(Formula I)}$$

wherein:

X is a cell-division cycle protein 20 (Cdc20) binding moiety;

Y is an E3 ubiquitin ligase binding moiety; and

L is a linker covalently attached to X and Y or a bond between X and Y.

In some embodiments, X comprises, consists essentially of, or consists of a moiety selected from the group consisting of Apcin and Apcin-A, or a derivative thereof.

In some embodiments, X comprises, consists essentially of, or consists of:

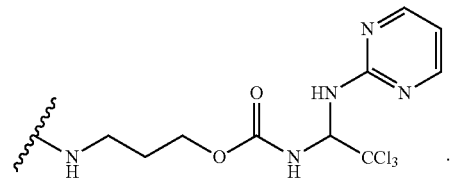

In some embodiments, Y is a moiety that binds an E3 ubiquitin ligase selected from the group consisting of Von Hippel-Lindau (VHL) E3 ubiquitin ligase, cereblon (CRBN), IAP, and MDM2. In some embodiments, Y is VHL E3 ubiquitin ligase. In some embodiments, Y is CRBN. In some embodiments, Y is IAP. In some embodiments, Y is MDM2. In some embodiments, Y is VHL E3 ubiquitin ligase or CRBN.

In some embodiments, Y comprises, consists essentially of, or consists of a moiety selected from:

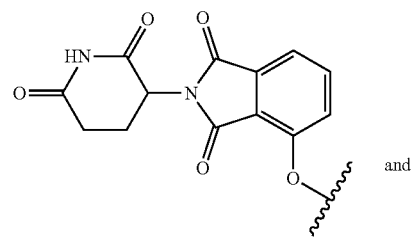

and

-continued

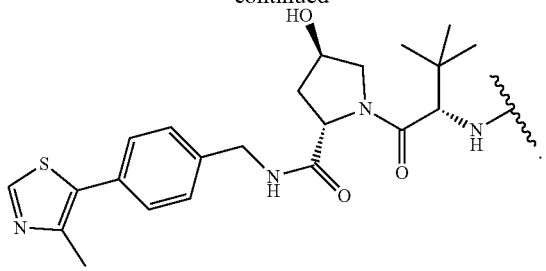

In some embodiments, Y comprises, consists essentially of, or consists of:

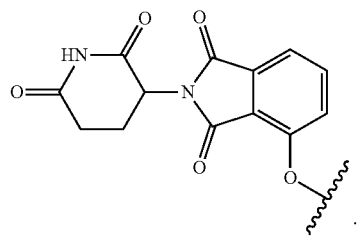 [SMILES: *Oc1cccc2c1C(=O)N(C1CCC(=O)NC1=O)C2=O]

In some embodiments, Y comprises, consists essentially of, or consists of

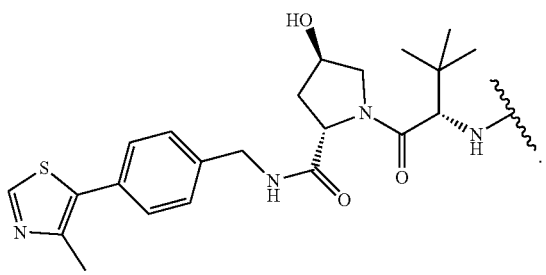 [SMILES: *N[C@H](C(=O)N1C[C@H](O)C[C@H]1C(=O)NCc1ccc(-c2scnc2C)cc1)C(C)(C)C]

Other non-limiting examples of Y are described in WO2019023553, WO2018226542, WO2018144649, WO2018140809, WO2018102067, WO2018119448, WO2018119441, WO2018119357, WO2018118598, WO2018102725, WO2018102067, WO2018071606, WO2018053354, WO2017030814, WO2017011590, WO2017011371, WO2016197114, WO2016197032, WO2016149668, WO2016118666, and WO2015160845, each of which is incorporated by reference herein.

In some embodiments, L comprises, consists essentially of, or consists of

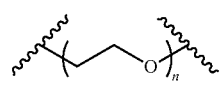

wherein n is an integer greater than or equal to 2. In some embodiments, n is 2, 3, 4, 5, 6, 7, 8, 9, 10, 11, 12, 13, 14, or 15. In some embodiments, n is 2, 3, 4, 5, 6, 7, 8, or 9. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9.

In some embodiments, L is selected from the group consisting of:

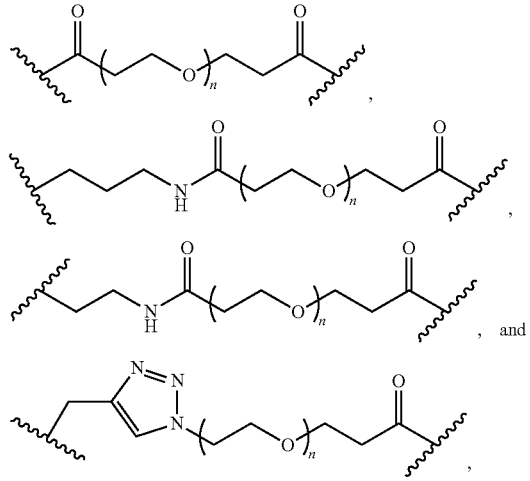

wherein n is an integer greater than or equal to 2.

In some embodiments, L is selected from the group consisting of:

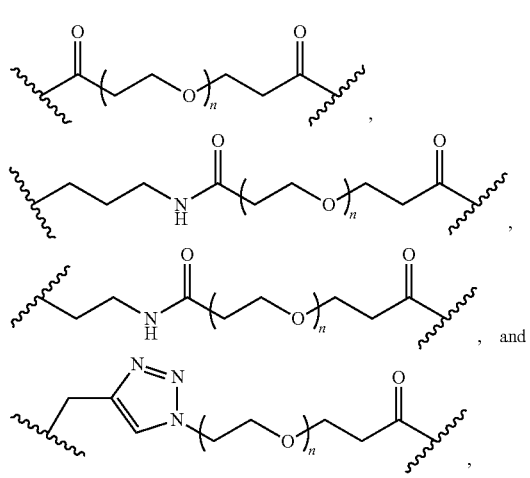

wherein n is 2, 3, 4, 5, 6, 7, 8, 9, 10, 11, 12, 13, 14, or 15. In some embodiments, L is selected from the group consisting of:

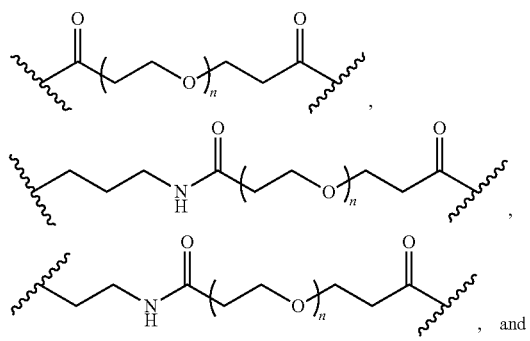

-continued

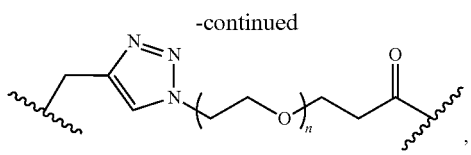

wherein n is 2, 3, 4, 5, 6, 7, 8, or 9. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9.

In some embodiments, L is

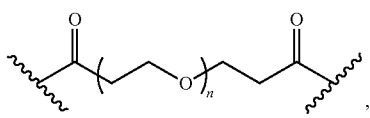

wherein n is 2, 3, 4, 5, 6, 7, 8, 9, 10, 11, 12, 13, 14, or 15. In some embodiments, n is 2, 3, 4, 5, 6, 7, 8, or 9. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9.

In some embodiments, L is

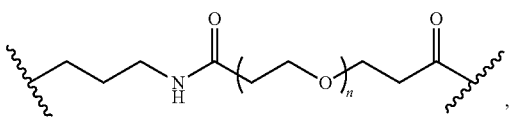

wherein n is 2, 3, 4, 5, 6, 7, 8, 9, 10, 11, 12, 13, 14, or 15. In some embodiments, n is 2, 3, 4, 5, 6, 7, 8, or 9.

In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9.

In some embodiments, L is

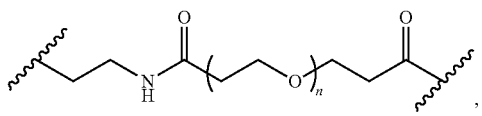

wherein n is 2, 3, 4, 5, 6, 7, 8, 9, 10, 11, 12, 13, 14, or 15. In some embodiments, n is 2, 3, 4, 5, 6, 7, 8, or 9. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9.

In some embodiments, L is

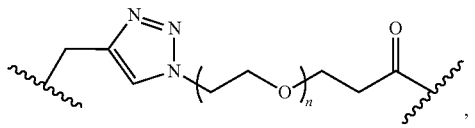

wherein n is 2, 3, 4, 5, 6, 7, 8, 9, 10, 11, 12, 13, 14, or 15. In some embodiments, n is 2, 3, 4, 5, 6, 7, 8, or 9. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9.

In some embodiments, the compound of Formula I, or a pharmaceutically acceptable salt thereof, is selected from the group consisting of

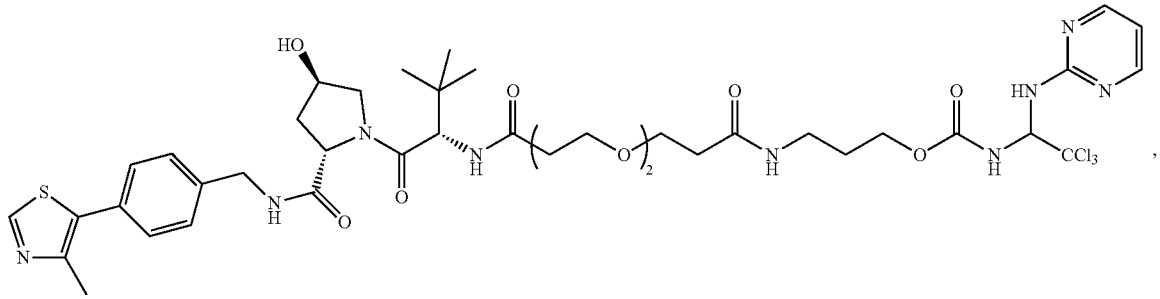

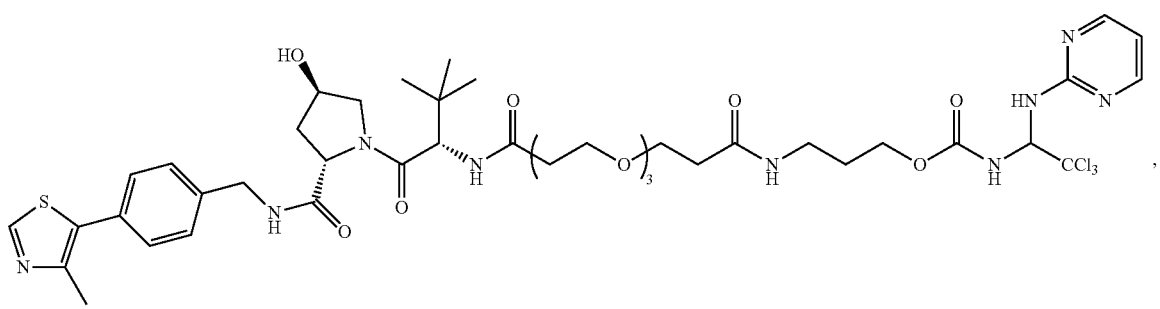

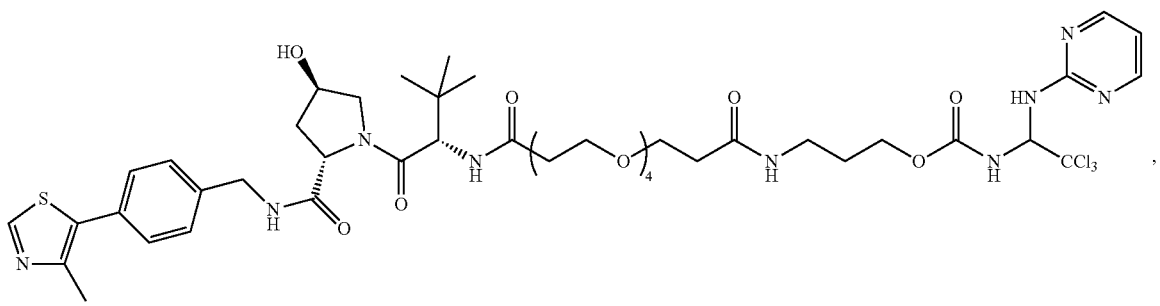
,
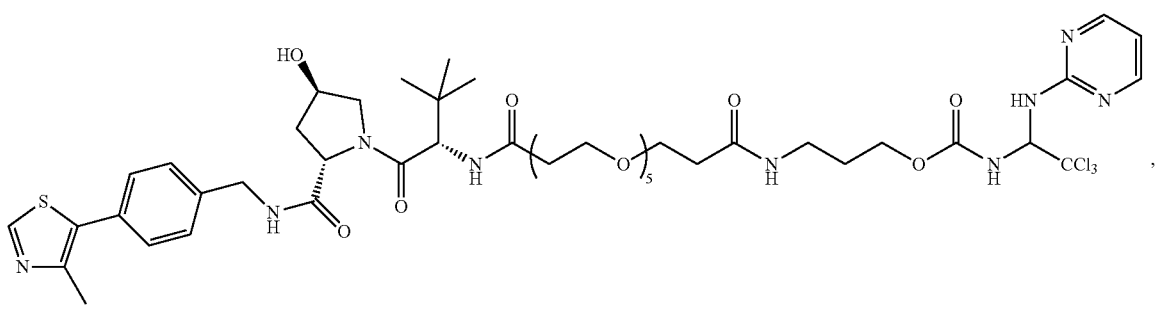
,
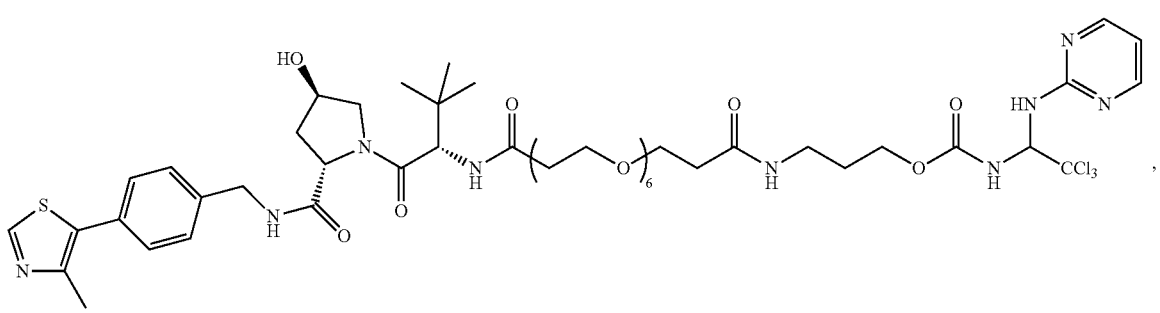
,
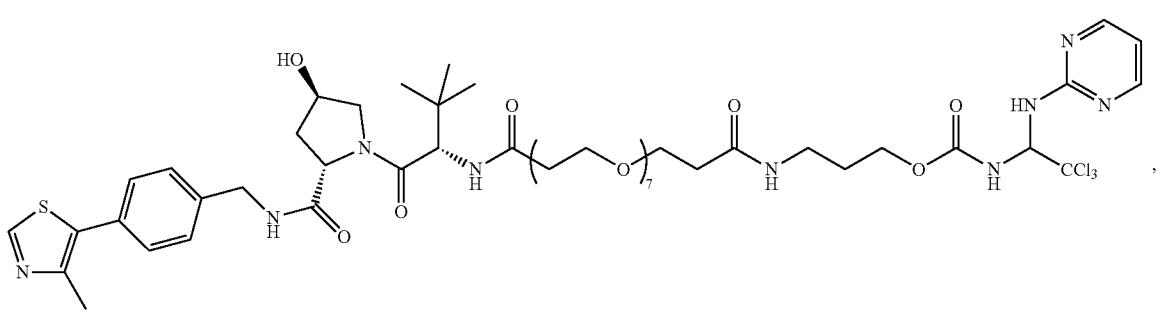
,
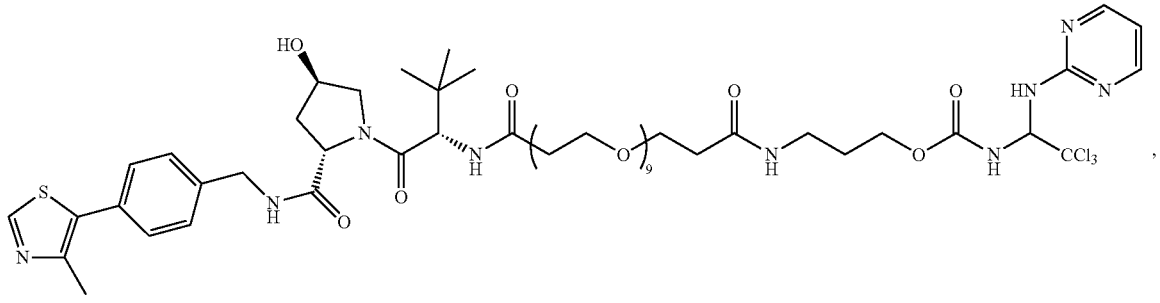
,

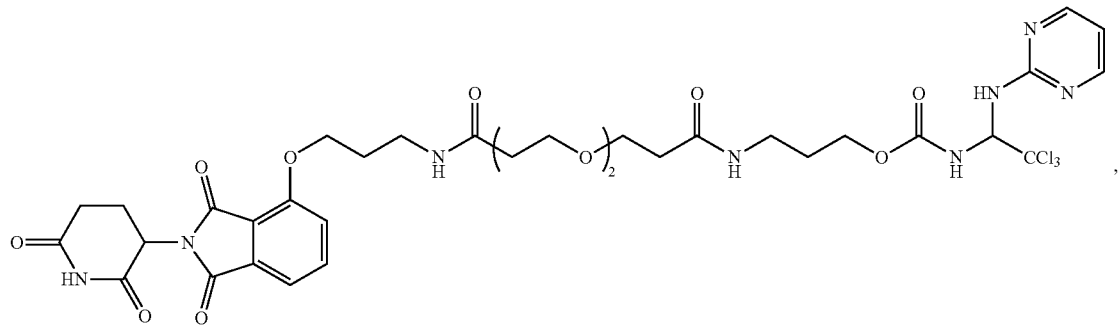
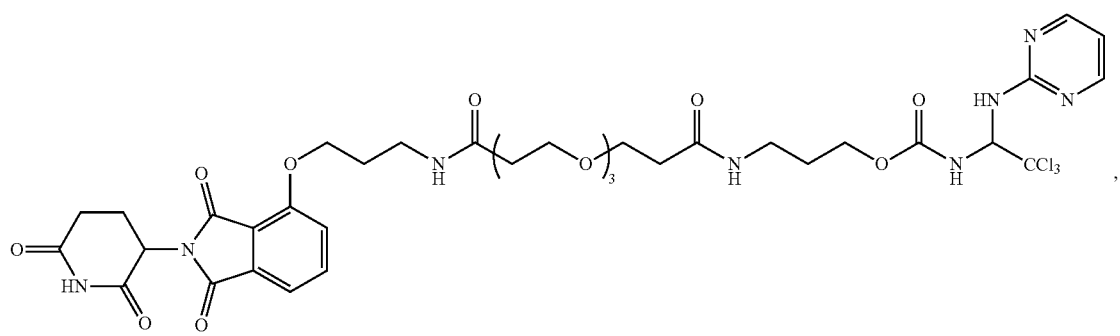
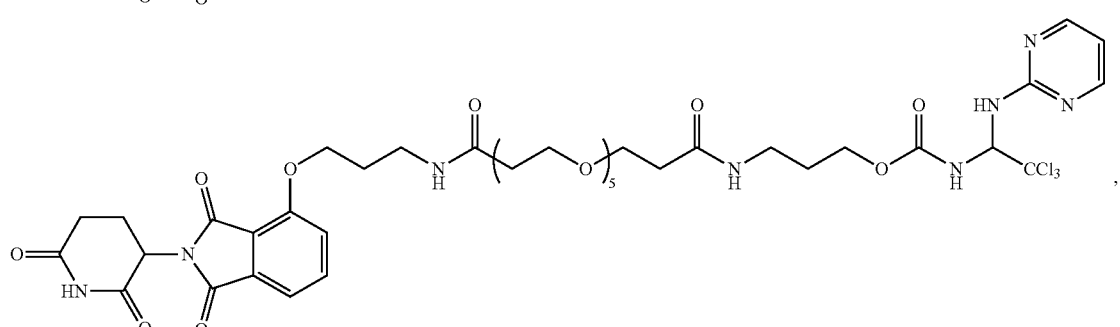
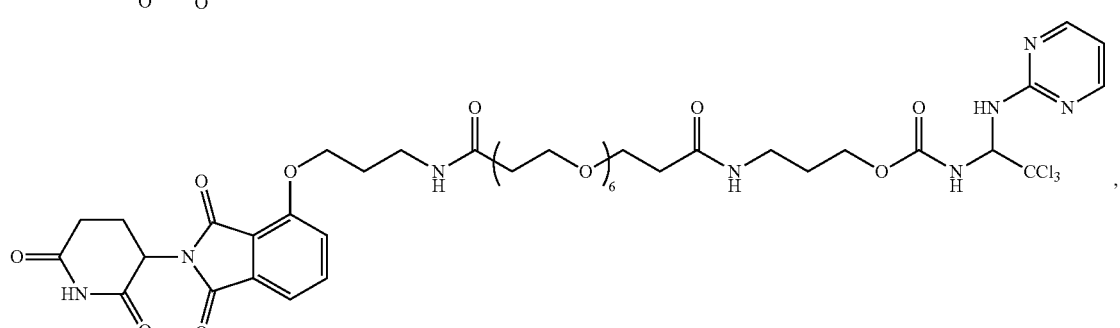
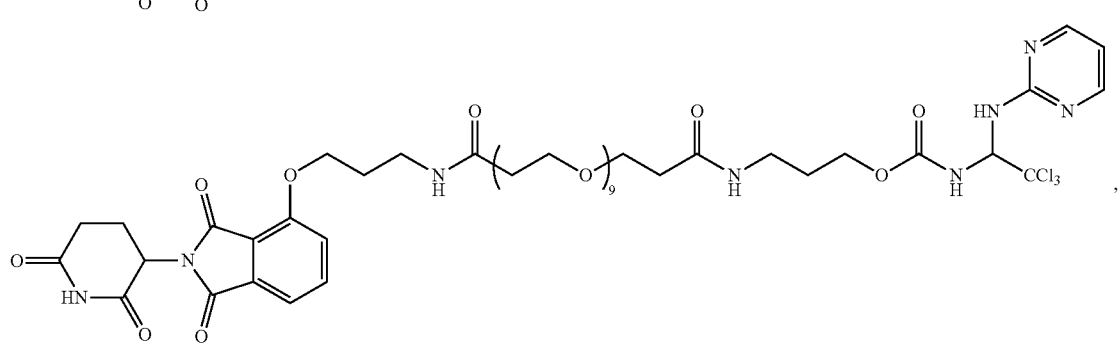

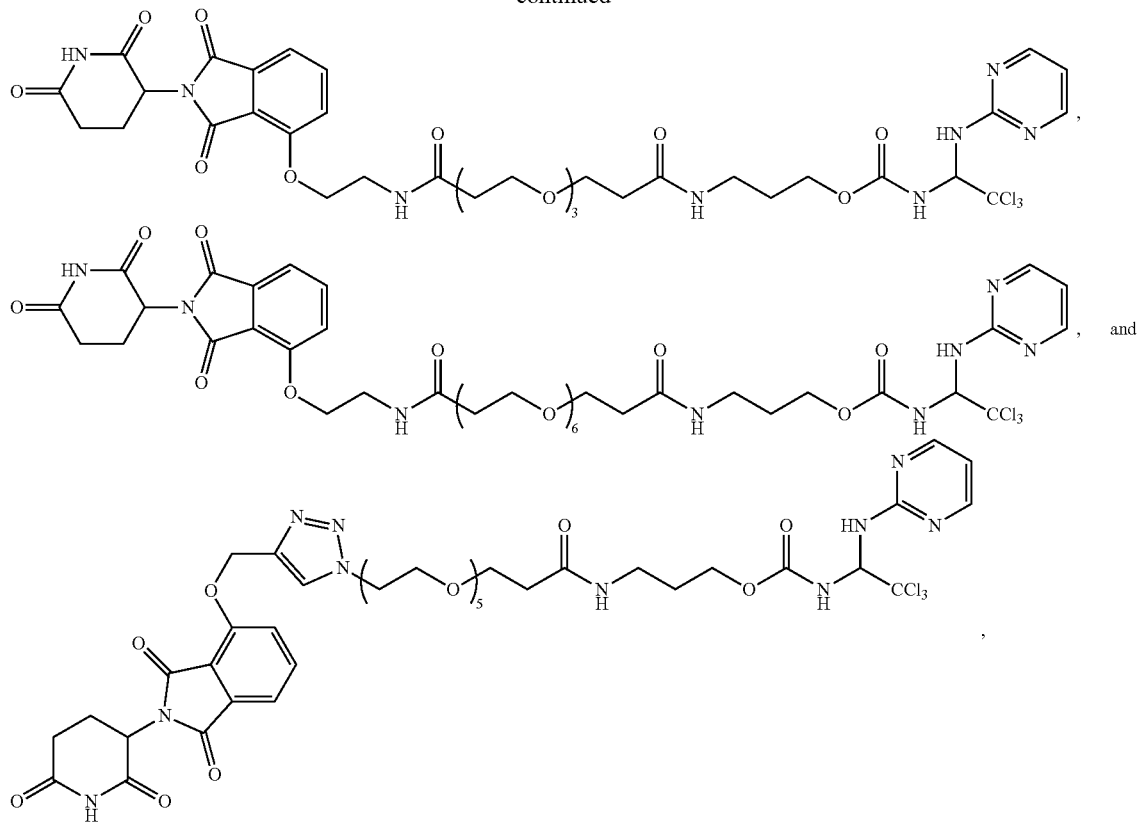

or a pharmaceutically acceptable salt thereof.

Pharmaceutically acceptable salts of the compounds disclosed herein are considered within the scope of the present invention. The compounds disclosed herein have a number of basic nitrogen groups, and as such, pharmaceutically acceptable salts can be formed with inorganic acids (such as hydrochloric acid, hydroboric acid, nitric acid, sulfuric acid, and phosphoric acid), organic acids (e.g. formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). The compounds disclosed herein may have acidic substituent groups, and in such cases, it can form salts with metals, such as alkali and earth alkali metals (e.g., $Na^+$, $Li^+$, $K^+$, $Ca^{2+}$, $Mg^{2+}$, $Zn^{2+}$), organic amines (e.g., ammonia, trimethylamine, triethylamine, pyridine, picoline, ethanolamine, diethanolamine, triethanolamine) or basic amino acids (e.g., arginine, lysine and ornithine).

Compositions

In some embodiments, a compound described herein is formulated as a pharmaceutically acceptable composition when combined with at least one pharmaceutically acceptable carrier and/or excipient. Such pharmaceutically acceptable carrier(s) and/or excipient(s) are non-toxic and do not interfere with the efficacy of active ingredient (e.g., the compound of Formula I). The precise nature of the pharmaceutically acceptable carrier(s) and/or excipient(s) depends on the route of administration. The compositions can be formulated for any pharmaceutically acceptable route of administration, such as for example, by oral, parenteral, pulmonary, topical, rectal, nasal, vaginal administration, or via implanted reservoir. Parenteral or systemic administration includes, but is not limited to, subcutaneous, intravenous, intraperitoneally, intramuscular, intra-articular, intra-synovial, intrasternal, intrathecal, intralesional and intracranial injections. The compositions disclosed herein may be formulated into preparations in solid, semi-solid, liquid or gaseous forms, such as tablets, capsules, powders, granules, ointments, solutions, suppositories, injections, inhalants and aerosols.

In pharmaceutical dosage forms, the compound disclosed herein may be administered in the form of its pharmaceutically acceptable salt, or the compound may also be used alone or in appropriate association, as well as in combination, with other pharmaceutically active compounds. The following methods and excipients are merely exemplary and are in no way limiting.

For oral administration, liquid or solid dose formulations may be used. Some non-limiting examples of oral dosage formulations include tablets, gelatin capsules, pills, troches, elixirs, suspensions, syrups, wafers, chewing gum and the like. The compounds can be mixed with a suitable pharmaceutical carrier (vehicle) or excipient as understood by practitioners in the art. Non-limiting examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intrathecal, topical, intranasal, subcutaneous, or transdermal administration, formulations of the compounds useful in the methods of the present invention may utilize conventional diluents, carriers, or excipients etc., such as are known in the art can be employed to deliver the compounds. For example, the formulations may comprise one or more of the following: a stabilizer, a surfactant (such as a nonionic, ionic, anionic, cationic, or zwitterionic surfactant), and optionally a salt and/or a buffering agent. The compound may be delivered in the form of a solution or in a reconstituted lyophilized form.

In some embodiments, the stabilizer may, for example, be an amino acid, such as for instance, glycine or an oligosaccharide, such as for example, sucrose, tetralose, lactose or a dextran. Alternatively, the stabilizer may be a sugar alcohol, such as for instance, mannitol, sorbitol, xylitol, or a combination thereof. In some embodiments, the stabilizer or combination of stabilizers constitutes from about 0.1% to about 10% by weight of the formulation, or any percentage in between these two values.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) to about 10% (w/v), or any percentage in between these two values.

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5, or any pH in between these two values. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the compounds useful in the methods of the present invention may additionally comprise one or more conventional additives. Some non-limiting examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The amount of any individual excipient in the composition will vary depending on the role of the excipient, the dosage requirements of the active agent components, and particular needs of the composition. Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

One or more additional active agents may be administered with a compound disclosed herein, either sequentially or concomitantly. In some embodiments, the compound disclosed herein and the one or more additional active agents are administered within a single composition. Non-limiting examples of additional active agents include tamoxifen, temozolamide, docetaxel, volasertib, topetecan, gemcitabine, cisplatin, and fluorouracil (5-FU).

In some embodiments, a compound disclosed herein can be administered to a patient in an effective amount ranging from about 0.001 mg/kg to about 100 mg/kg per day. This includes 0.001, 0.0025, 0.005, 0.0075, 0.01, 0.025, 0.05, 0.075, 0.1, 0.25, 0.5, 0.75, 1, 2, 3, 4, 5, 6, 7, 8, 9, 10, 15, 20, 25, 30, 35, 40, 45, 50, 55, 60, 65, 70, 75, 80, 85, 90, 95, or 100 mg/kg.

Generally, a therapeutically effective amount of a compound disclosed herein will range from a total daily dosage of about 0.1 mg/day to 1000 mg/day, about 30-720 mg/day, about 60-600 mg/day, or about 100-480 mg/day, or more. In some embodiments, a therapeutically effective amount of a compound disclosed herein will range from about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, multiple dosages include two, three, or four doses per day.

In some embodiments, the therapeutically effective amount of a compound disclosed herein is at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, at least 725 mg/day, at least 750 mg/day, at least 775 mg/day, at least 800 mg/day, at least 825 mg/day, at least 850 mg/day, at least 875 mg/day, at least 900 mg/day, at least 925 mg/day, at least 950 mg/day, at least 975 mg/day, or at least 1000 mg/day.

Of course, the dosage may be changed according to the patient's age, weight, susceptibility, symptom, or the efficacy of the compound.

The compounds and compositions disclosed herein may be used to prepare formulations and medicaments that prevent or treat cancer.

Methods

In another aspect, provided herein are methods of treating cancer in a subject in need thereof, the method comprising administering to the subject a therapeutically effective amount of a compound or composition disclosed herein. Non-limiting examples of the cancer include breast cancer (such as, but not limited to MDA-MB-231, MDA-MB-435, or MCF-7 breast cancers), gastric cancer, glioma, lung adenocarcinoma, lung squamous cell carcinoma, endometrioid ovarian cancer, prostate cancer, bladder cancer, melanoma, and mantle cell lymphoma.

In some embodiments, provided herein are methods of treating breast cancer in a subject in need thereof, the method comprising, consisting essentially of, or consisting of administering to the subject a therapeutically effective amount of a compound or composition disclosed herein. In some embodiments, provided herein are methods of treating breast cancer in a subject in need thereof, the method comprising, consisting essentially of, or consisting of administering to the subject a therapeutically effective amount of a compound or composition disclosed herein, wherein the breast cancer is MDA-MB-231, MDA-MB-435, or MCF-7 breast cancer.

In some embodiments, provided herein are methods of treating gastric cancer in a subject in need thereof, the method comprising, consisting essentially of, or consisting of administering to the subject a therapeutically effective amount of a compound or composition disclosed herein. In some embodiments, provided herein are methods of treating glioma in a subject in need thereof, the method comprising, consisting essentially of, or consisting of administering to the subject a therapeutically effective amount of a compound or composition disclosed herein. In some embodiments, provided herein are methods of treating lung adenocarcinoma in a subject in need thereof, the method comprising, consisting essentially of, or consisting of administering to the subject a therapeutically effective amount of a compound or composition disclosed herein. In some embodiments, provided herein are methods of treating lung squamous cell carcinoma in a subject in need thereof, the method comprising, consisting essentially of, or consisting of administering to the subject a therapeutically effective amount of a compound or composition disclosed herein. In some embodiments, provided herein are methods of treating endometrioid ovarian cancer in a subject in need thereof, the method comprising, consisting essentially of, or consisting of administering to the subject a therapeutically effective amount of a compound or composition disclosed herein. In some embodiments, provided herein are methods of treating prostate cancer in a subject in need thereof, the method comprising, consisting essentially of, or consisting of administering to the subject a therapeutically effective amount of a compound or composition disclosed herein. In some embodiments, provided herein are methods of treating bladder cancer in a subject in need thereof, the method comprising, consisting essentially of, or consisting of administering to the subject a therapeutically effective amount of a compound or composition disclosed herein. In some embodiments, provided herein are methods of treating melanoma in a subject in need thereof, the method comprising, consisting essentially of, or consisting of administering to the subject a therapeutically effective amount of a compound or composition disclosed herein. In some embodiments, provided herein are methods of treating mantle cell lymphoma in a subject in need thereof, the method comprising, consisting essentially of, or consisting of administering to the subject a therapeutically effective amount of a compound or composition disclosed herein.

In another aspect, provided herein are methods of inducing Cdc20 degradation in a cell, the method comprising, consisting essentially of, or consisting of contacting the cell with an effective amount of a compound or composition disclosed herein.

In another aspect, provided herein are methods of blocking mitotic progression in a subject, the method comprising, consisting essentially of, or consisting of administering to the subject a therapeutically effective amount of a compound or composition disclosed herein.

In another aspect, provided herein are methods of inhibiting tumor proliferation in a subject, the method comprising, consisting essentially of, or consisting of administering to the subject a therapeutically effective amount of a compound or composition disclosed herein.

In another aspect, provided herein are methods of re-sensitizing a subject to cancer treatment with tamoxifen, the method comprising, consisting essentially of, or consisting of administering to the subject a therapeutically effective amount of a compound or composition disclosed herein, wherein the subject is resistant to treatment with tamoxifen prior to administration of the compound or composition disclosed herein.

In another aspect, provided herein are methods of re-sensitizing a subject to cancer treatment with temozolamide (TMZ), the method comprising, consisting essentially of, or consisting of administering to the subject a therapeutically effective amount of a compound or composition disclosed herein, wherein the subject is resistant to treatment with TMZ prior to administration of the compound or composition disclosed herein. In some embodiments the cancer is glioma.

In another aspect, provided herein are methods of re-sensitizing a subject to cancer treatment with docetaxel, the method comprising, consisting essentially of, or consisting of administering to the subject a therapeutically effective amount of a compound or composition disclosed herein, wherein the subject is resistant to treatment with docetaxel prior to administration of the compound or composition disclosed herein. In some embodiments the cancer is castration-resistant prostate cancer.

In another aspect, provided herein are methods of re-sensitizing a subject to cancer treatment with volasertib, the method comprising, consisting essentially of, or consisting of administering to the subject a therapeutically effective amount of a compound or composition disclosed herein, wherein the subject is resistant to treatment with volasertib prior to administration of the compound or composition disclosed herein. In some embodiments the cancer is ovarian cancer.

In another aspect, provided herein are methods of re-sensitizing a subject to cancer treatment with paclitaxel, the method comprising, consisting essentially of, or consisting of administering to the subject a therapeutically effective amount of a compound or composition disclosed herein, wherein the subject is resistant to treatment with paclitaxel prior to administration of the compound or composition disclosed herein. In some embodiments the cancer is breast cancer.

In another aspect, provided herein are methods of sensitizing a subject to cancer treatment with tamoxifen, the method comprising, consisting essentially of, or consisting of administering to the subject a therapeutically effective amount of a compound or composition disclosed herein, wherein the subject is less resistant to treatment with tamoxifen after administration of the compound or composition disclosed herein.

In another aspect, provided herein are methods of sensitizing a subject to cancer treatment with temozolamide (TMZ), the method comprising, consisting essentially of, or consisting of administering to the subject a therapeutically effective amount of a compound or composition disclosed herein, wherein the subject is less resistant to treatment with TMZ after administration of the compound or composition disclosed herein. In some embodiments the cancer is glioma.

In another aspect, provided herein are methods of sensitizing a subject to cancer treatment with docetaxel, the method comprising, consisting essentially of, or consisting of administering to the subject a therapeutically effective amount of a compound or composition disclosed herein, wherein the subject is less resistant to treatment with docetaxel after administration of the compound or composition disclosed herein. In some embodiments the cancer is castration-resistant prostate cancer. In some embodiments the cancer is breast cancer.

In another aspect, provided herein are methods of sensitizing a subject to cancer treatment with volasertib, the method comprising, consisting essentially of, or consisting of administering to the subject a therapeutically effective amount of a compound or composition disclosed herein, wherein the subject is less resistant to treatment with volasertib after administration of the compound or composition disclosed herein. In some embodiments the cancer is ovarian cancer.

In another aspect, provided herein are methods of sensitizing a subject to cancer treatment with paclitaxel, the method comprising, consisting essentially of, or consisting of administering to the subject a therapeutically effective amount of a compound or composition disclosed herein, wherein the subject is less resistant to treatment with paclitaxel after administration of the compound or composition disclosed herein. In some embodiments the cancer is breast cancer.

In another aspect, provided herein are methods of sensitizing a subject to cancer treatment with cisplatin, the method comprising, consisting essentially of, or consisting of administering to the subject a therapeutically effective amount of a compound or composition disclosed herein, wherein the subject is less resistant to treatment with cisplatin after administration of the compound or composition disclosed herein. In some embodiments the cancer is breast cancer.

The present invention, thus generally described, will be understood more readily by reference to the following examples, which are provided by way of illustration and are not intended to be limiting of the present invention.

EXAMPLES

Compound Preparation Examples

Example 1. Preparation of Apcin-A-PEG5-VHL1 [(R)-25-((2S,4R)-4-hydroxy-2-((4-(4-methylthiazol-5-yl)benzyl)carbamoyl) pyrrolidine-1-carbonyl)-26, 26-dimethyl-5,23-dioxo-8,11,14,17,20-pentaoxa-4, 24-diazaheptacosyl (2,2,2-trichloro-1-(pyrimidin-2-ylamino)ethyl)carbamate)]

Step 1.

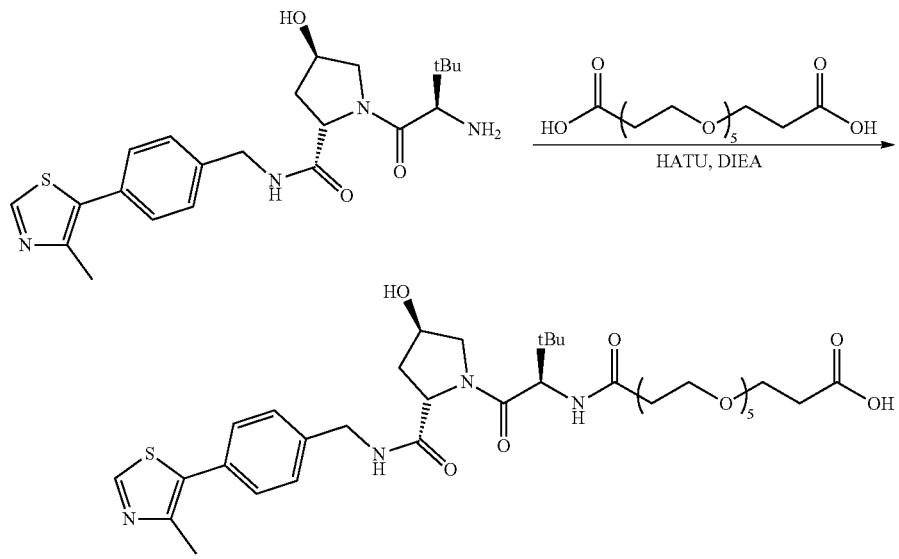

To a 2-ml vial containing 4,7,10,13,16-pentaoxanonadecanedioic acid (629 mg, 2 equiv., 1.86 mmol) was added DMF (3 mL) and the mixture was cooled in an ice/water bath. To the mixture, HATU (353 mg, 1 Eq, 929 µmol) and DIPEA (480 mg, 0.65 mL, 4 equiv., 3.72 mmol) were added. The mixture was stirred in the cold bath for 15 min after which (2S,4R)-1-((R)-2-amino-3,3-dimethylbutanoyl)-4-hydroxy-N-(4-(4-methylthiazol-5-yl)benzyl)pyrrolidine-2-carboxamide (400 mg, 1 equiv., 929 µmol) in DMF (0.2 mL) was added. The reaction mixture was allowed to stir overnight as the ice bath expired for 16 h after which LC/MS indicated formation of product. The mixture was directly purified by RP HPLC, eluting with 5 to 50% acetonitrile in water (0.1% formic acid modifier) to provide (R)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoic acid (440 mg, 63.1%) as a light yellow colored oil. LCMS (ESI) m/z: [M+H]+ 751.48. $^1$H NMR (500 MHz, Methanol-$d_4$) δ 8.90 (s, 1H), 8.65 (t, J=6.1 Hz, 1H), 7.92 (d, J=9.0 Hz, 1H), 7.54-7.36 (m, 5H), 4.68 (d, J=9.0 Hz, 1H), 4.62-4.54 (m, 2H), 4.52 (qd, J=4.9, 4.1, 2.7 Hz, 1H), 4.38 (dd, J=15.4, 5.4 Hz, 1H), 3.91 (dt, J=11.2, 1.7 Hz, 1H), 3.82 (dd, J=11.0, 3.9 Hz, 1H), 3.80-3.70 (m, 4H), 3.68-3.55 (m, 18H), 3.37 (s, 7H), 2.56 (t, J=6.2 Hz, 2H), 2.50 (s, 4H), 2.24 (ddt, J=11.6, 7.6, 2.0 Hz, 1H), 2.10 (ddd, J=13.3, 9.0, 4.5 Hz, 1H), 1.06 (s, 11H). $^{13}$C NMR (126 MHz, CD₃OD) δ 173.94, 173.15, 172.45, 170.74, 151.45, 147.63, 138.91, 132.01, 130.09, 128.96, 127.59, 70.17, 70.14, 70.11, 70.07, 70.02, 70.00, 69.68, 66.89, 66.42, 59.46, 57.61, 56.59, 42.42, 37.52, 36.01, 35.40, 34.44, 25.63, 14.42.
Step 2.

J=11.0, 3.9 Hz, 1H), 3.79-3.68 (m, 5H), 3.68-3.55 (m, 18H), 3.28 (t, J=6.7 Hz, 2H), 2.59 (ddd, J=15.0, 7.5, 5.3 Hz, 1H), 2.54-2.46 (m, 5H), 2.43 (t, J=6.0 Hz, 3H), 2.29-2.21 (m, 1H), 2.10 (ddd, J=13.3, 9.1, 4.4 Hz, 1H), 2.07 (s, 1H), 1.85 (p, J=6.4 Hz, 3H), 1.06 (s, 11H). ¹³C NMR (126 MHz, CD₃OD) δ 173.15, 172.77, 172.68, 172.41, 170.74, 163.30,

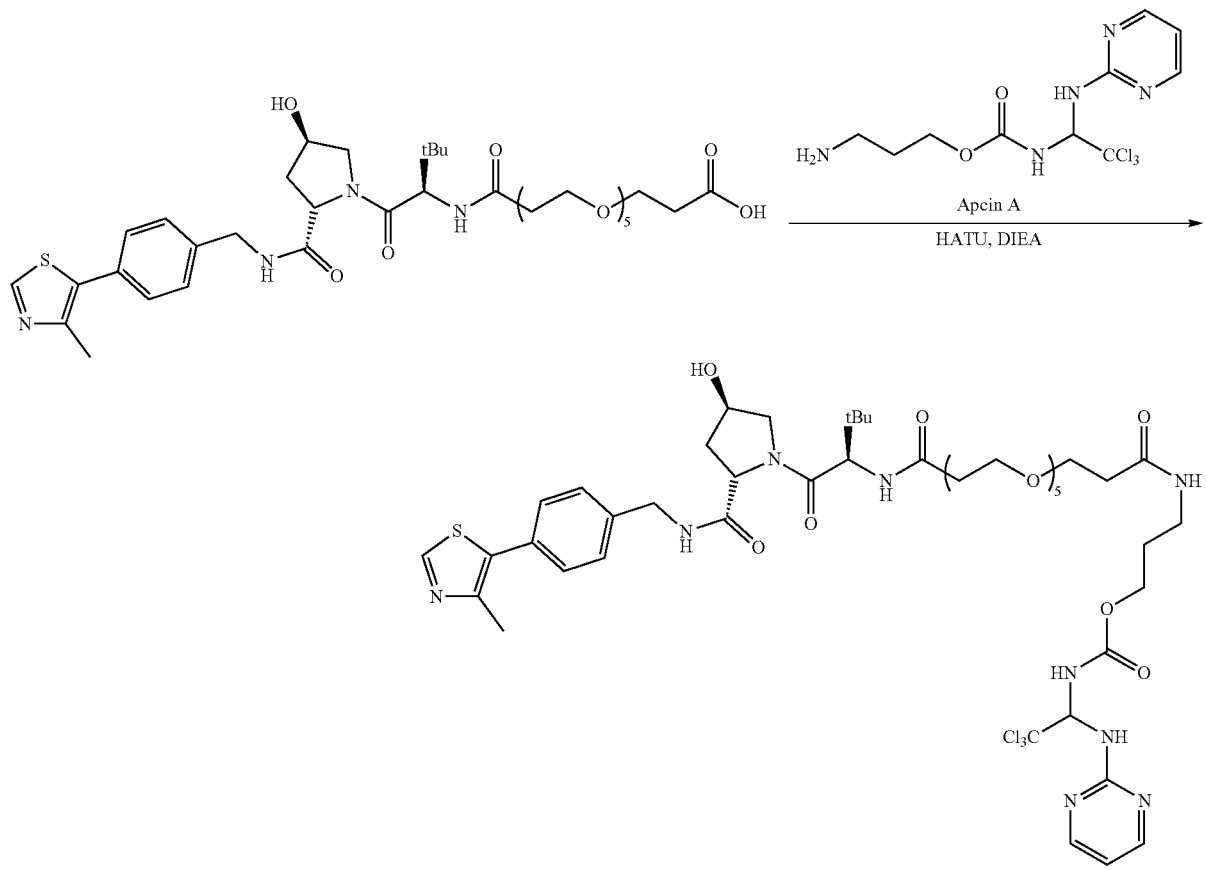

160.74, 158.11, 151.45, 147.63, 138.90, 132.01, 130.10, 128.96, 127.59, 116.74, 112.59, 101.95, 70.18, 70.14, 70.12, 70.04, 70.02, 69.95, 69.68, 66.90, 66.87, 62.81, 59.46, 57.61, 56.60, 42.43, 37.53, 36.38, 36.33, 36.02, 35.83, 35.40, 28.47, 25.65, 14.44.

To a solution of (R)-21-((2S,4R)-4-hydroxy-2-((4-(4-methylthiazol-5-yl)benzyl) carbamoyl)pyrrolidine-1-carbonyl)-22,22-dimethyl-19-oxo-4,7,10,13,16-pentaoxa-20-azatricosanoic acid (200 mg, 1 equiv., 266 μmol) in DMF (2 mL) in an ice/water bath was simultaneously added 3-aminopropyl (2,2,2-trichloro-1-(pyrimidin-2-ylamino)ethyl) carbamate [Apcin A] (183 mg, 2 equiv., 533 μmol) and HATU (253 mg, 2.5 equiv., 666 μmol). Right after addition, DIEA (138 mg, 186 μL, 4 equiv., 1.07 mmol) was added and the reaction mixture was stirred as the ice bath expired for 2 h after which LC/MS indicated product. The mixture was directly purified via RP HPLC, eluting with 10 to 90% acetonitrile in water (0.1% formic acid modifier) to provide (R)-25-((2S,4R)-4-hydroxy-2-((4-(4-methylthiazol-5-yl) benzyl)carbamoyl) pyrrolidine-1-carbonyl)-26,26-dimethyl-5,23-dioxo-8,11,14,17,20-pentaoxa-4,24-diazaheptacosyl (2,2,2-trichloro-1-(pyrimidin-2-ylamino)ethyl)carbamate (214 mg, 74.7%) as a yellow oil. LCMS (ESI) m/z: [M+H]⁺ 539.24 (m/2 observed). ¹H NMR (500 MHz, Methanol-d₄) δ 8.90 (s, 1H), 8.65 (t, J=6.0 Hz, 1H), 8.41 (d, J=4.9 Hz, 2H), 8.12 (s, 1H), 7.98-7.86 (m, 2H), 7.49 (d, J=8.2 Hz, 2H), 7.45-7.41 (m, 2H), 6.89-6.71 (m, 2H), 4.68 (d, J=9.0 Hz, 1H), 4.63-4.48 (m, 4H), 4.38 (dd, J=15.5, 5.2 Hz, 1H), 4.16 (t, J=6.4 Hz, 2H), 3.91 (dt, J=11.3, 1.8 Hz, 1H), 3.82 (dd, Example 2. Preparation of Apcin-A-PEG2-VHL1

This compound was prepared using a similar procedure as described in Example 1. HRMS (ESI⁺) m z 966.2749. ¹H NMR (500 MHz, Methanol-d₄) δ 8.89 (s, 1H), 8.40 (dd, J=4.8, 2.2 Hz, 3H), 7.48 (d, J=8.0 Hz, 3H), 7.43 (dd, J=8.3, 2.5 Hz, 2H), 6.85-6.77 (m, 2H), 4.68 (s, 1H), 4.63-4.49 (m, 4H), 4.38 (d, J=15.5 Hz, 1H), 4.15 (t, J=6.5 Hz, 2H), 3.91 (dd, J=11.1, 2.1 Hz, 1H), 3.82 (ddd, J=11.0, 3.9, 1.7 Hz, 1H), 3.72 (dt, J=12.1, 5.9 Hz, 5H), 3.67-3.61 (m, 1H), 3.60 (s, 4H), 3.28 (d, J=7.2 Hz, 2H), 2.61-2.46 (m, 6H), 2.42 (td, J=6.1, 2.8 Hz, 2H), 2.28-2.21 (m, 1H), 2.17-2.06 (m, 1H), 1.87-1.80 (m, 2H), 1.06 (s, 9H).

Example 3. Preparation of Apcin-A-PEG3-VHL1

This compound was prepared using a similar procedure as described in Example 1. HRMS (ESI⁺) m z 1010.3002. ¹H NMR (500 MHz, Methanol-d$_4$) δ 8.89 (s, 1H), 8.40 (d, J=4.8 Hz, 4H), 7.91 (d, J=8.9 Hz, 1H), 7.49 (d, J=8.0 Hz, 3H), 7.43 (d, J=8.0 Hz, 3H), 6.85-6.78 (m, 4H), 4.70-4.65 (m, 1H), 4.62-4.50 (m, 5H), 4.38 (d, J=15.4 Hz, 1H), 4.15 (t, J=6.3 Hz, 3H), 3.91 (d, J=11.0 Hz, 1H), 3.82 (dd, J=11.0, 3.9 Hz, 1H), 3.75 (dd, J=5.3, 2.4 Hz, 1H), 3.72 (dt, J=12.3, 5.7 Hz, 5H), 3.67-3.56 (m, 13H), 3.29 (d, J=8.1 Hz, 4H), 2.67-2.54 (m, 1H), 2.49 (s, 6H), 2.43 (t, J=6.0 Hz, 3H), 2.28-2.18 (m, 1H), 2.10 (ddd, J=13.3, 9.1, 4.5 Hz, 1H), 1.87-1.80 (m, 4H), 1.06 (s, 9H).

Example 4. Preparation of Apcin-A-PEG4-VHL1

This compound was prepared using a similar procedure as described in Example 1. LCMS (ESI$^+$) 518.19. $^1$H NMR (500 MHz, Methanol-d$_4$) δ 8.90 (s, 1H), 8.40 (d, J=4.8 Hz, 2H), 7.55-7.33 (m, 4H), 6.92-6.72 (m, 2H), 4.85 (s, 6H), 4.68 (d, J=9.1 Hz, 1H), 4.59-4.50 (m, 2H), 4.42-4.36 (m, 1H), 4.20-4.12 (m, 2H), 3.90 (s, 1H), 3.83 (d, J=3.9 Hz, 1H), 3.78-3.68 (m, 3H), 3.67-3.58 (m, 12H), 2.46 (d, J=31.7 Hz, 5H), 1.84 (t, J=6.5 Hz, 2H), 1.06 (s, 9H).

Example 5. Preparation of Apcin-A-PEG6-VHL1

This compound was prepared using a similar procedure as described in Example 1. LC/MS (ESI$^+$) 560.74. $^1$H NMR (500 MHz, Methanol-d$_4$) δ 8.90 (s, 1H), 8.41 (d, J=4.8 Hz, 2H), 7.49 (d, J=8.3 Hz, 2H), 7.47-7.41 (m, 3H), 6.86-6.79 (m, 2H), 4.67 (s, 1H), 4.63-4.48 (m, 4H), 4.38 (d, J=15.5 Hz, 1H), 4.16 (t, J=6.5 Hz, 2H), 3.91 (dt, J=11.2, 1.8 Hz, 1H), 3.82 (dd, J=11.0, 3.9 Hz, 1H), 3.79-3.69 (m, 5H), 3.62 (h, J=4.2, 3.6 Hz, 27H), 3.32-3.26 (m, 8H), 2.60 (ddd, J=14.9, 7.4, 5.2 Hz, 1H), 2.54-2.46 (m, 5H), 2.43 (t, J=6.0 Hz, 3H), 1.85 (p, J=6.4 Hz, 2H), 1.06 (s, 9H).

Example 6. Preparation of Apcin-A-PEG7-VHL1

This compound was prepared using a similar procedure as described in Example 1. HRMS (ESI$^+$) m/z 1164.4204. $^1$H NMR (500 MHz, Chloroform-d) δ 8.65 (s, 1H), 8.33 (d, J=5.3 Hz, 2H), 7.37-7.29 (m, 4H), 6.70-6.60 (m, 2H), 4.51 (d, J=9.0 Hz, 1H), 4.48 (s, 1H), 4.20-4.13 (m, 2H), 4.10 (d, J=12.8 Hz, 1H), 3.75-3.63 (m, 6H), 3.59 (t, J=4.5 Hz, 25H), 3.57 (s, 3H), 3.29 (dq, J=17.7, 6.7 Hz, 2H), 2.51-2.37 (m, 9H), 2.19 (dd, J=13.5, 8.0 Hz, 1H), 1.00 (s, 9H).

Example 7. Preparation of Apcin-A-PEG9-VHL1

This compound was prepared using a similar procedure as described in Example 1. LCMS HRMS (ESI$^+$) m/z 1252.4722. $^1$H NMR (500 MHz, Chloroform-d) δ 8.34 (t, J=5.3 Hz, 2H), 7.37-7.30 (m, 5H), 6.68 (t, J=4.8 Hz, 1H), 4.50 (t, J=8.3 Hz, 3H), 4.19-4.13 (m, 2H), 4.10 (d, J=11.6 Hz, 1H), 3.73-3.64 (m, 6H), 3.60 (dt, J=6.0, 2.8 Hz, 33H), 3.57 (s, 5H), 3.33-3.24 (m, 2H), 2.53-2.38 (m, 9H), 1.81 (s, 2H), 0.95 (s, 9H).

Example 8. Preparation of Apcin-A-PEG5-VHL1*(Negative Control)

This compound was prepared using a similar procedure as described in Example 1. $^1$H NMR (500 MHz, Methanol-d$_4$) δ 8.90 (s, 1H), 8.65 (t, J=6.0 Hz, 1H), 8.41 (d, J=4.9 Hz, 2H), 8.12 (s, 1H), 7.98-7.86 (m, 2H), 7.49 (d, J=8.2 Hz, 2H), 7.45-7.41 (m, 2H), 6.89-6.71 (m, 2H), 4.68 (d, J=9.0 Hz, 1H), 4.63-4.48 (m, 4H), 4.38 (dd, J=15.5, 5.2 Hz, 1H), 4.16 (t, J=6.4 Hz, 2H), 3.91 (dt, J=11.3, 1.8 Hz, 1H), 3.82 (dd, J=11.0, 3.9 Hz, 1H), 3.79-3.68 (m, 5H), 3.68-3.55 (m, 18H), 3.28 (t, J=6.7 Hz, 2H), 2.59 (ddd, J=15.0, 7.5, 5.3 Hz, 1H), 2.54-2.46 (m, 5H), 2.43 (t, J=6.0 Hz, 3H), 2.29-2.21 (m, 1H), 2.10 (ddd, J=13.3, 9.1, 4.4 Hz, 1H), 2.07 (s, 1H), 1.85 (p, J=6.4 Hz, 3H), 1.06 (s, 11H). $^{13}$C NMR (126 MHz, CD$_3$OD) δ 173.15, 172.77, 172.68, 172.41, 170.74, 163.30, 160.74, 158.11, 151.45, 147.63, 138.90, 132.01, 130.10, 128.96, 127.59, 116.74, 112.59, 101.95, 70.18, 70.14, 70.12, 70.04, 70.02, 69.95, 69.68, 66.90, 66.87, 62.81, 59.46, 57.61, 56.60, 42.43, 37.53, 36.38, 36.33, 36.02, 35.83, 35.40, 28.47, 25.65, 14.44. LC/MS (ESI$^+$) 539.24.

Example 9. Preparation of Apcin-A-PEG3-C3-Phthalimide

Step 1

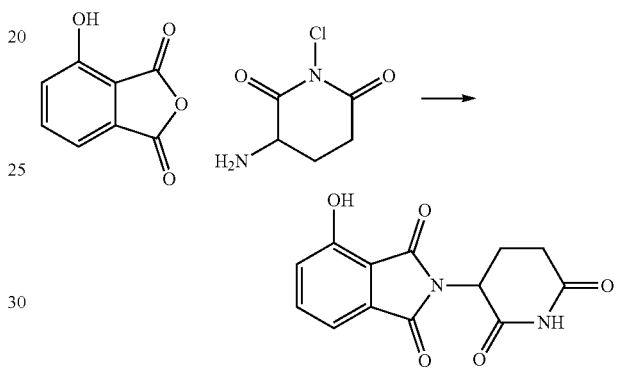

In an 8-mL vial, 4-hydroxyisobenzofuran-1,3-dione (725 mg, 1 equiv., 4.42 mmol) and 3-amino-1-chloropiperidine-2,6-dione (718 mg, 1 equiv., 4.42 mmol) were suspended in pyridine and heated at 110° C. overnight (16 h). Pyridine was removed with nitrogen and the crude material was partitioned in water and EtOAc. Layers were separated, and the aqueous one was extracted EtOAc (2×) and dichloromethane (2×). Combined organic layers were dried over Na$_2$SO$_4$, filtrated and concentrated to obtain 145 mg (12% yield) of product. Material was used in the next step without further purification.

Step 2

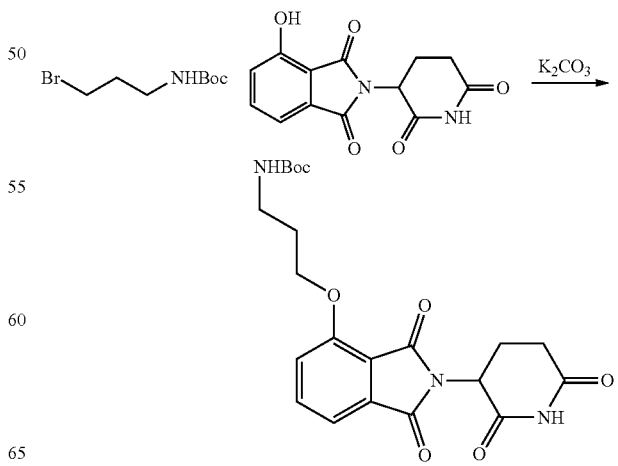

31

In an 8-ml vial, 2-(2,6-dioxopiperidin-3-yl)-4-hydroxyisoindoline-1,3-dione (209 mg, 1.1 equiv., 762 µmol) and potassium carbonate (76.6 mg, 0.8 equiv., 550 µmol) were added to a solution of tert-butyl (3-bromopropyl)carbamate (165 mg, 1 equiv., 693 µmol) in DMF (3.5 mL). The resulting green suspension was stirred at RT and monitored by LCMS. After 24 h, the reaction mixture was quenched by adding water (4 mL) and extracted with EtOAc (3×), washed with brine, dried over $Na_2SO_4$, filtered, and concentrated. Purification by preparative HPLC afforded 160 mg (54%) yield. LCMS (ESI$^+$) 432.42.

Step 3

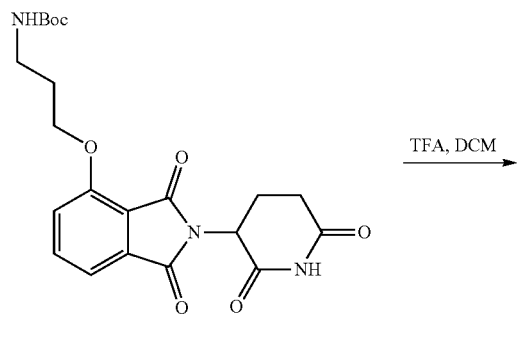

32

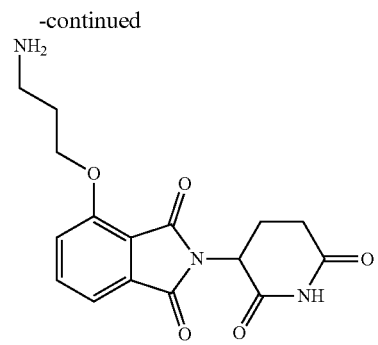

A solution of 2-(2,6-dioxopiperidin-3-yl)-4-hydroxyisoindoline-1,3-dione (209 mg, 1.1 equiv., 762 µmol) in dichloromethane (0.5 mL) and TFA (50 µL) was stirred at RT for 16 h. The mixture was concentrated with N2 and used in the next step.

Step 4

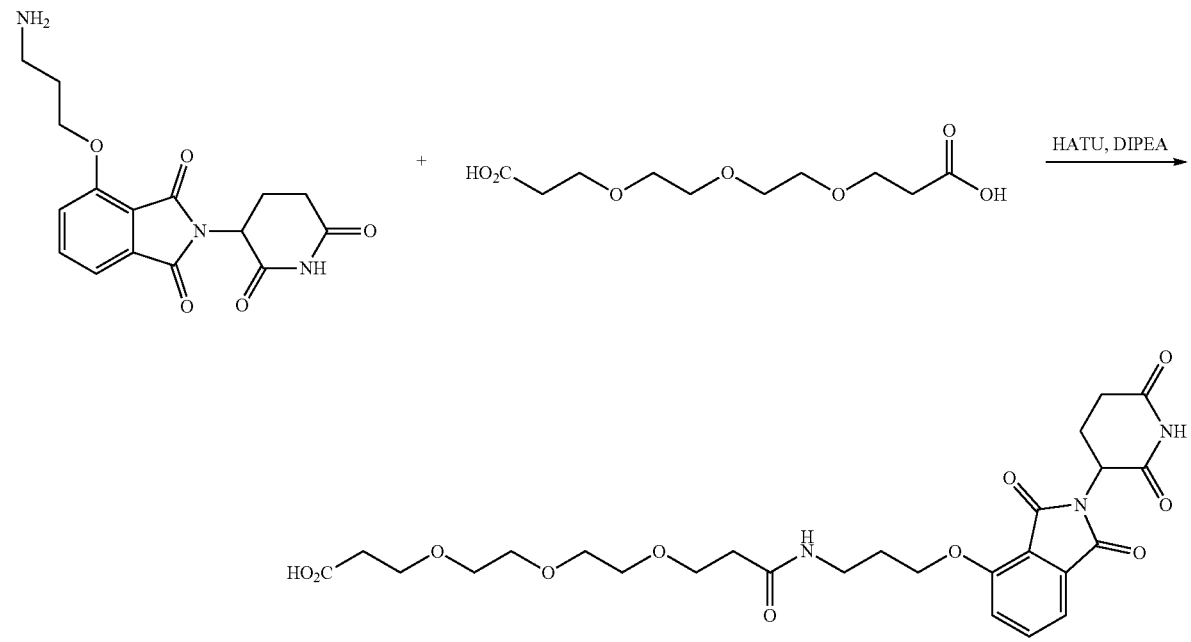

To a 2-mL vial with an ice-cold solution of 3,3'-((oxybis(ethane-2,1-diyl))bis(oxy))dipropionic acid (30.4 mg, 2 equiv., 121 µmol) and HATU (25.4 mg, 1.1 equiv., 66.8 µmol) in DMF (0.25 mL), was added DIPEA (31.4 mg, 42 µL, 4 equiv., 243 µmol), and the resultant solution was stirred for 15 min. Then, 4-(3-aminopropoxy)-2-(2,6-dioxopiperidin-3-yl)isoindoline-1,3-dione (20.1 mg, 1 equiv., 60.7 µmol) dissolved in DMF (0.25 mL) was added and the reaction mixture was stirred from 0° C. to RT for 16 h. LCMS showed product and di-amide compound. The crude material was directly purified by reverse phase preparative HPLC, and used in the next step.

Step 5

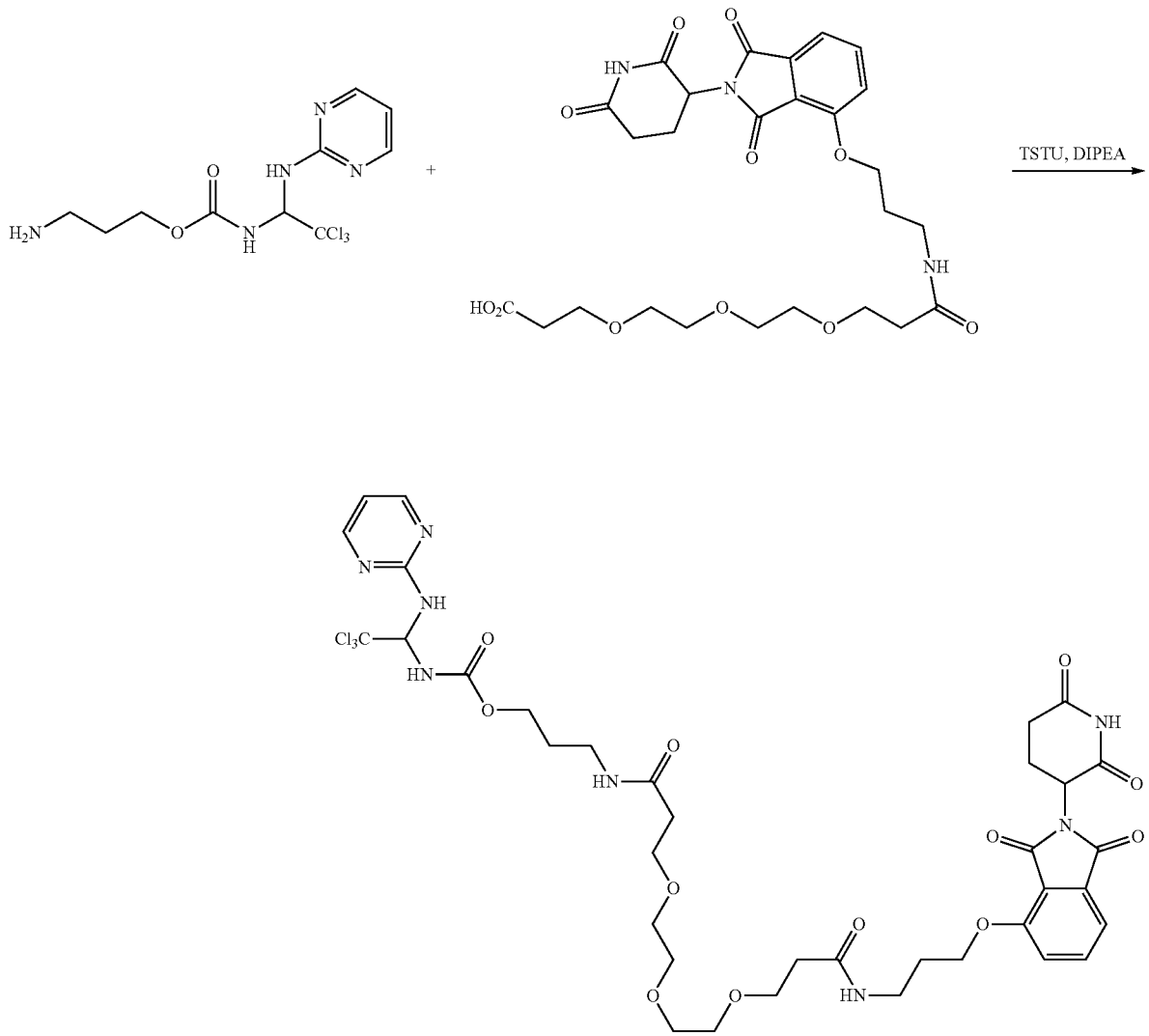

To a 4-mL vial with an ice-cold solution of 17-((2-(2,6-dioxopiperidin-3-yl)-1,3-dioxoisoindolin-4-yl)oxy)-13-oxo-4,7,10-trioxa-14-azaheptadecanoic acid (9 mg, 1 equiv., 20 μmol) in DMF (0.25 mL), TSTU (7 mg, 1.5 equiv., 30 μmol) was added followed by DIPEA (8 mg, 10 μL, 4 equiv., 60 μmol). The reaction mixture was stirred for 15 min and 3-aminopropyl (2,2,2-trichloro-1-(pyrimidin-2-ylamino)ethyl)carbamate (7 mg, 1.25 equiv., 20 μmol) dissolved in DMF (0.25 mL) was added to the mixture. The resultant mixture was stirred for 16 h from 0° C. to RT. LCMS of the mixture indicated presence of product. The crude material was directly purified by reverse phase preparative HPLC to give the final compound (3.4 mg, 24%). HRMS (ESI$^+$) 889.2287. $^1$H NMR (500 MHz, Chloroform-d) δ 8.36 (dd, J=12.3, 4.8 Hz, 3H), 7.70 (t, J=7.9 Hz, 1H), 7.55 (s, 1H), 7.53-7.44 (m, 1H), 7.19 (dd, J=8.5, 1.9 Hz, 1H), 6.92-6.87 (m, 1H), 6.83 (s, 1H), 6.71-6.63 (m, 2H), 4.98-4.90 (m, 1H), 4.28 (dt, J=10.2, 5.3 Hz, 1H), 4.24-4.18 (m, 2H), 4.16 (s, 2H), 3.77 (t, J=6.9 Hz, 1H), 3.74-3.68 (m, 3H), 3.68-3.64 (m, 3H), 3.58 (dtd, J=12.6, 8.1, 8.1, 4.3 Hz, 12H), 3.54-3.50 (m, 3H), 3.37 (t, J=5.5 Hz, 1H), 3.28 (dhept, J=13.3, 6.8 Hz, 3H), 2.88-2.69 (m, 3H), 2.60 (dt, J=11.7, 6.9 Hz, 3H), 2.41 (dq, J=16.8, 5.7 Hz, 3H), 2.18-2.03 (m, 4H), 1.81 (p, J=6.8 Hz, 6H), 1.61 (q, J=6.2 Hz, 2H), 1.57-1.46 (m, 2H).

Example 10. Preparation of Apcin-A-PEG2-C3-Phthalimide

This compound was prepared using a similar procedure as described in Example 9. HRMS (ESI$^+$) 845.2016. $^1$H NMR (500 MHz, Chloroform-d) δ 8.36 (dd, J=11.0, 4.8 Hz, 3H), 7.71 (ddd, J=8.5, 7.3, 1.2 Hz, 1H), 7.56-7.51 (m, 1H), 7.48 (dd, J=7.3, 2.9 Hz, 1H), 7.19 (dd, J=8.5, 3.1 Hz, 1H), 6.88-6.79 (m, 2H), 6.72-6.65 (m, 3H), 4.93 (ddt, J=8.3, 5.6, 2.5 Hz, 1H), 4.32-4.13 (m, 5H), 3.81-3.63 (m, 6H), 3.63-3.41 (m, 9H), 3.41-3.35 (m, 1H), 3.34-3.21 (m, 3H), 2.89-

2.79 (m, 1H), 2.79-2.73 (m, 1H), 2.73-2.67 (m, 1H), 2.60 (dt, J=23.1, 7.0 Hz, 3H), 2.46-2.41 (m, 1H), 2.41-2.34 (m, 2H), 2.20-2.10 (m, 2H), 2.06 (dp, J=6.6, 3.6 Hz, 3H), 1.81 (dp, J=12.4, 6.2 Hz, 4H), 1.62 (p, J=6.0 Hz, 1H), 1.57-1.46 (m, 2H).

Example 11. Preparation of Apcin-A-PEG5-C3-Phthalimide

This compound was prepared using a similar procedure as described in Example 9. HRMS (ESI$^+$) 999.2637. $^1$H NMR (500 MHz, Chloroform-d) δ 8.37 (d, J=4.9 Hz, 1H), 7.69 (s, 1H), 7.47 (d, J=7.3 Hz, 1H), 7.19 (d, J=8.4 Hz, 1H), 6.68 (s, 1H), 4.94 (s, 1H), 4.32-4.11 (m, 2H), 3.81-3.66 (m, 3H), 3.53-3.24 (m, 2H), 2.89-2.70 (m, 1H), 2.66-2.52 (m, 1H), 2.46-2.35 (m, 1H), 2.17-2.02 (m, 1H), 1.80 (p, J=6.4 Hz, 1H), 1.60 (q, J=6.2 Hz, 1H), 1.52 (tt, J=12.2, 4.9 Hz, 1H).

Example 12. Preparation of Apcin-A-PEG3-C2-Phthalimide

This compound was prepared using a similar procedure as described in Example 9. HRMS (ESI$^+$) 875.2118. $^1$H NMR (500 MHz, Chloroform-d) δ 10.54 (s, 1H), 8.42-8.33 (m, 4H), 7.69 (ddd, J=8.6, 7.3, 1.4 Hz, 2H), 7.48 (d, J=7.2 Hz, 2H), 7.31-7.23 (m, 11H), 6.90-6.83 (m, 4H), 6.72-6.68 (m, 2H), 6.59 (d, J=9.2 Hz, 1H), 4.95 (ddd, J=11.9, 5.3, 3.7 Hz, 2H), 4.29-4.13 (m, 8H), 3.74-3.62 (m, 12H), 3.55 (d, J=5.7 Hz, 11H), 3.28 (tq, J=6.9, 4.5, 3.7 Hz, 5H), 2.91-2.82 (m, 2H), 2.82-2.70 (m, 4H), 2.48 (t, J=6.0 Hz, 4H), 2.44-2.36 (m, 5H), 2.13 (ddd, J=7.8, 5.7, 2.8 Hz, 3H), 1.80 (p, J=6.3, 5.8 Hz, 5H).

Example 13. Preparation of Apcin-A-PEG6-C2-Phthalimide

This compound was prepared using a similar procedure as described in Example 9. HRMS (ESI$^+$) 1007.2913. $^1$H NMR (500 MHz, Chloroform-d) δ 8.38 (s, 1H), 7.68 (s, 1H), 7.47 (d, J=7.3 Hz, 1H), 7.28 (s, 1H), 6.70 (s, 2H), 4.94 (ddd, J=12.1, 5.4, 1.9 Hz, 1H), 4.34-4.10 (m, 5H), 3.69 (ddq, J=13.4, 5.9, 3.8, 3.3 Hz, 6H), 3.29 (qd, J=6.5, 2.5 Hz, 3H), 2.90-2.68 (m, 3H), 2.45 (dt, J=35.5, 5.8 Hz, 5H), 2.12 (ddd, J=7.9, 6.4, 3.8 Hz, 1H), 1.91 (s, 13H), 1.81 (q, J=6.5, 5.8 Hz, 3H), 1.41-1.14 (m, 4H), 0.90-0.77 (m, 2H), 0.16 (d, J=10.8 Hz, 1H).

Example 14. Preparation of Apcin-A-PEG6-C3-Phthalimide

This compound was prepared using a similar procedure as described in Example 9. HRMS (ESI$^+$) 1021.3066. $^1$H NMR (500 MHz, Chloroform-d) δ 8.37 (d, J=4.9 Hz, 1H), 7.47 (d, J=7.3 Hz, 1H), 7.20 (s, 1H), 6.93 (s, 1H), 6.82 (d, J=9.5 Hz, 1H), 6.69 (t, J=4.9 Hz, 1H), 6.53 (s, 1H), 6.40 (s, 1H), 4.94 (ddt, J=8.5, 5.6, 2.5 Hz, 1H), 4.32-4.13 (m, 3H), 3.79-3.66 (m, 2H), 3.48-3.42 (m, 1H), 3.34-3.23 (m, 1H), 2.85 (dd, J=12.3, 2.8 Hz, 1H), 2.73 (dd, J=12.6, 8.3 Hz, 1H), 2.60 (dt, J=12.2, 7.1 Hz, 1H), 2.46-2.38 (m, 1H), 2.14 (dd, J=5.4, 2.2 Hz, 1H), 2.06 (q, J=5.5 Hz, 1H), 1.81 (p, J=6.1 Hz, 1H).

Example 15. Preparation of Apcin-A-PEG9-C3-Phthalimide

This compound was prepared using a similar procedure as described in Example 9. HRMS (ESI$^+$) 1175.3664. $^1$H NMR (500 MHz, Chloroform-d) δ 8.36 (d, J=4.7 Hz, 1H), 7.69 (t, J=7.9 Hz, 1H), 7.46 (d, J=7.2 Hz, 1H), 7.19 (d, J=8.4 Hz, 1H), 6.83 (dd, J=28.1, 16.9 Hz, 1H), 6.69 (t, J=4.8 Hz, 1H), 6.35 (d, J=9.9 Hz, 1H), 4.97-4.88 (m, 1H), 4.32-4.12 (m, 2H), 3.81-3.64 (m, 2H), 3.54-3.23 (m, 2H), 2.78-2.70 (m, 1H), 2.62 (ddp, J=21.4, 14.7, 7.5, 6.8 Hz, 1H), 2.42 (t, J=5.6 Hz, 1H), 2.16-2.01 (m, 1H), 1.60 (q, J=6.1 Hz, 1H), 1.51 (dt, J=11.8, 6.0 Hz, 2H).

Example 16. Preparation of Apcin-A-PEG3-C3-Click-Phthalimide

Step 1

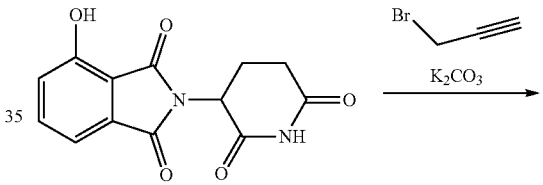

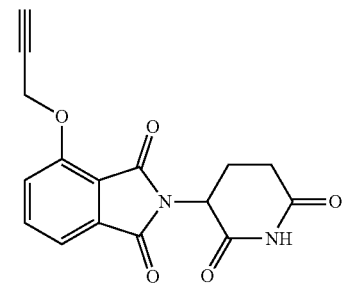

To an ice-cold mixture of 2-(2,6-dioxopiperidin-3-yl)-4-hydroxyisoindoline-1,3-dione (100 mg, 1 equiv., 365 μmol) and K$_2$CO$_3$ (101 mg, 2 equiv., 729 μmol) in MeCN (3 mL), was slowly added 3-bromoprop-1-yne (60 mg, 45 μL, 1.1 equiv., 401 μmol) dissolved in MeCN (1 mL). The resultant solution was stirred overnight warming to RT, then at 50° C. for 24 h. The reaction mixture was quenched by adding water, extracted with EtOAc, dried over Na$_2$SO$_4$, filtered and concentrated. Crude material was purified by preparative HPLC. LC/MS (ESI$^+$) 313.15.

Step 2

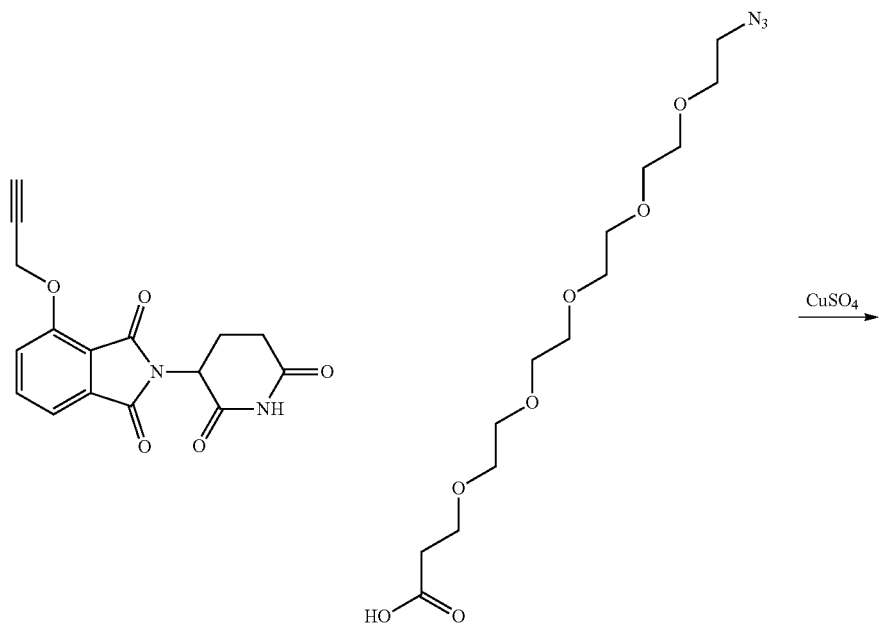

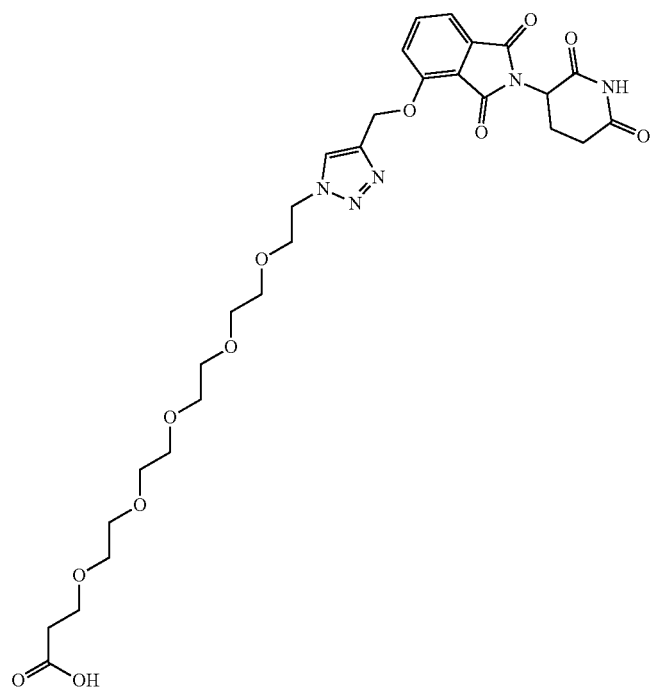

A mixture of 2-(2,6-dioxopiperidin-3-yl)-4-(prop-2-yn-1-yloxy)isoindoline-1,3-dione (13.00 mg, 1 equiv., 41.63 μmol), 1-azido-3,6,9,12,15-pentaoxaoctadecan-18-oic acid (13.96 mg, 1 equiv., 41.63 μmol), sodium (R)-2-((S)-1,2-dihydroxyethyl)-4-hydroxy-5-oxo-2,5-dihydrofuran-3-olate (4.124 mg, 0.5 equiv., 20.81 μmol) and copper(II) sulfate pentahydrate (2.599 mg, 0.25 equiv., 10.41 μmol) in EtOH, i-PrOH and water was stirred in a 4-mL vial at RT for 16 h. The crude material was purified by preparative HPLC and used as-is.

Step 3

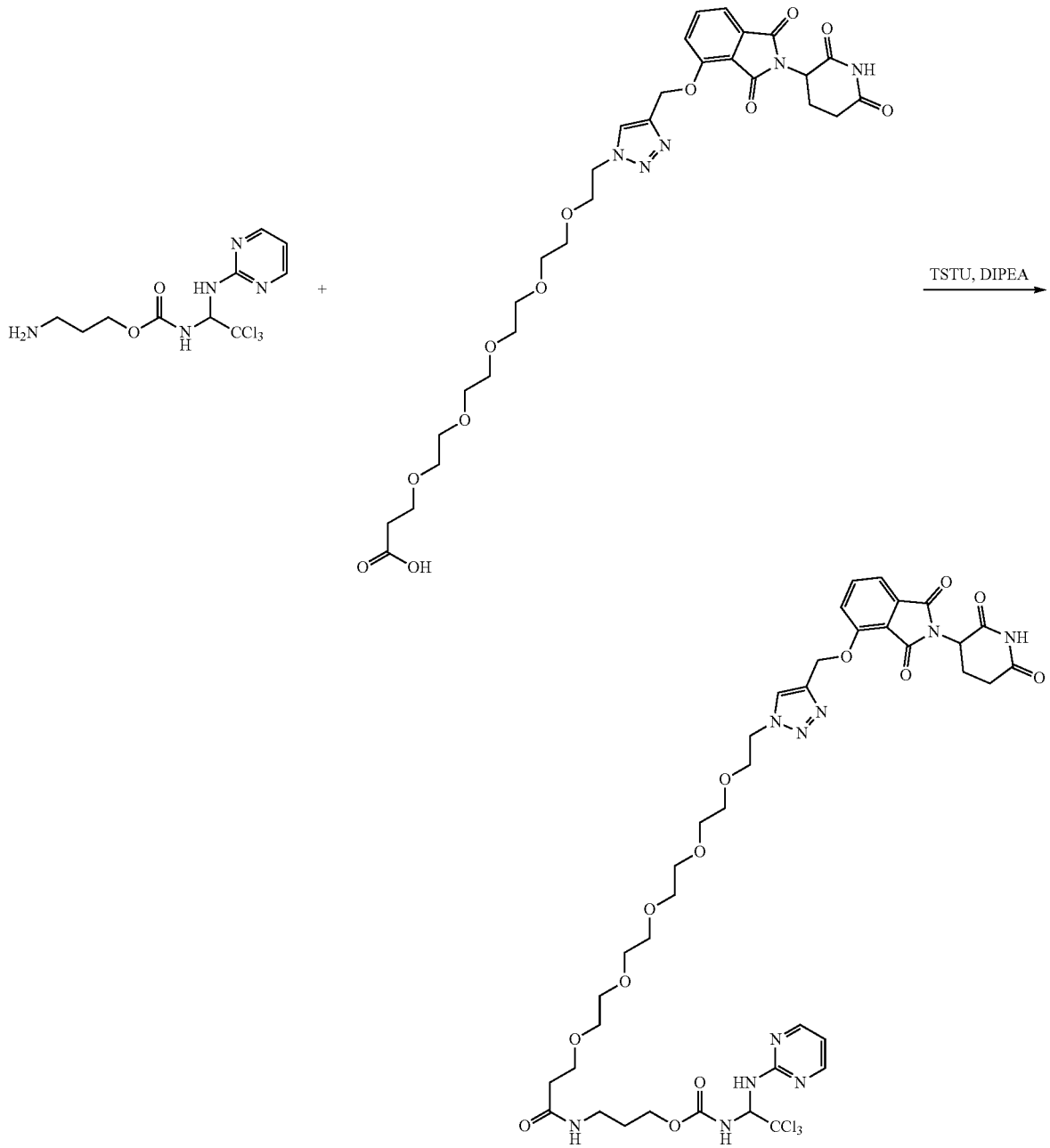

To a 4 mL vial with an ice cold solution of 1-(4-(((2-(2,6-dioxopiperidin-3-yl)-1,3-dioxoisoindolin-4-yl)oxy)methyl)-1H-1,2,3-triazol-1-yl)-3,6,9,12,15-pentaoxaoctadecan-18-oic acid (18 mg, 1 equiv., 27 μmol) in DMF (0.5 mL), was added TSTU (12 mg, 1.5 equiv., 41 μmol) followed by DIPEA (11 mg, 14 μL, 3 equiv., 82 μmol). The reaction mixture was stirred for 15 min, and 3-aminopropyl (2,2,2-trichloro-1-(pyrimidin-2-ylamino)ethyl)carbamate (15 mg, 1.6 equiv., 44 μmol) dissolved in DMF (0.5 mL) was added. The resultant mixture was stirred for 16 h from 0° C. to RT. The crude material was directly purified by preparative HPLC, providing 8 mg of desired product (30%). HRMS (ESI+) 971.2623. $^1$H NMR (500 MHz, Methanol-$d_4$) δ 8.40 (d, J=4.9 Hz, 3H), 8.23 (s, 1H), 7.91 (s, 1H), 7.81 (dd, J=8.5, 7.3 Hz, 1H), 7.64 (dd, J=7.9, 6.1 Hz, 1H), 7.50 (d, J=7.3 Hz, 1H), 7.38 (d, J=7.2 Hz, 1H), 7.21 (d, J=8.4 Hz, 1H), 6.83 (s, 1H), 6.80 (t, J=4.9 Hz, 1H), 5.47 (s, 2H), 5.15-5.09 (m, 1H), 4.66-4.59 (m, 2H), 4.15 (t, J=6.2 Hz, 3H), 3.95-3.83 (m, 3H), 3.74-3.63 (m, 3H), 2.97-2.84 (m, 1H), 2.80-2.66 (m, 2H), 2.42 (dd, J=7.5, 4.6 Hz, 3H), 2.20-2.07 (m, 1H), 1.84 (t, J=6.5 Hz, 3H).

Biological Examples

Cell lines, antibodies, and reagents. MCF-7 and MDA-MB-231 cells were purchased from ATCC. The MDA-MB-435 cells were provided by Dr. Dinghua Yu at the University of Texas, TX. The Flag-Cdc20 MDA-MB-231 stable cells were prepared by Dr. Cindy Mandy Wavelet. MCF-7, MDA-MB-231 cells were cultured in DMEM medium supplemented with 10% fetal bovine serum (FBS) and 1% penicillin-streptomycin. Flag-Cdc20 MDA-MB-231 cells were cultured in complete DMEM media introduced before with 1 µg/ml Tamoxifen. The Cdc20, cyclin-B and actin antibodies were purchased from Sigma. The actin antibodies were diluted 1:5000. The Cdc20, Cyclin-B and ubiquitin antibodies were diluted 1:1000. The agarose beads were purchased from Cell Signaling Technology.

Western blotting. Cells were lysed in RIPA buffer (50 mM Tris (pH 7.5), 150 mM NaCl, 1% NP-40, 0.5% sodium deoxycholate, 0.1% SDS) supplemented with protease (11697498001, Roche) and phosphatase inhibitors (10 mM sodium fluoride, 10 mM β-glycerophosphate, 2 mM sodium orthovanadate and 10 mM sodium pyrophosphate) for 10 min and heated at 95° C. for 5 min. The lysates were analyzed by SDS/PAGE. Western blotting was performed by transferring samples onto a nitrocellulose membrane, incubating in 5% milk in TBST (Tris-buffered Saline with Tween 20) at room temperature for 1 h and probing with indicated antibody overnight at 4° C. Membranes were visualized using the ECL prime western blotting detection reagent (GE Healthcare, RPN2232).

Flag-Cdc20 pull-down assay. The Flag-Cdc20 MDA-MB-231 stable cells were treated with 5 µM of DMSO, Apcin or CP5V with 10 µM of proteasome inhibitor MG-132 for 8 h at 37° C. Cells were then lysed on ice in 50 mM Tris-HCl (pH 7.5), 150 mM NaCl, 1 mM EDTA, 1% NP-40, 10% glycerol, supplemented with protease (11697498001, Roche), phosphatase, (10 mM sodium fluoride, 2 mM sodium orthovanadate, and 10 mM β-glycerophosphate) and deubiquitinase inhibitors (10 mM N-ethylmaleimide, 20 µM PR-619) for 10 min. The cells were collected by scratch with a scraper and then centrifuged at 15,000 RPM for 10 min. Equal amounts of supernatants were then incubated with 50 µL pre-washed Anti-Flag agarose beads at 4° C. for 2 h. Beads were then collected by centrifugation (5000 RPM for 1 min), washed and re-suspended in 2×SDS buffer. Beads were then boiled for 5 min and analyzed by SDS/PAGE. Western blotting was performed according to standard protocols.

Cell proliferation assays. Cells were seeded in 96-well plates at the concentration of 3000 cells per well in 180 µL of media and incubated at 37° C. for 3 days. MDA-MB-231, MDA-MB-435 and MDA-MB-435 eb cells were seeded in phenol red free DMEM+10% charcoal-stripped FBS (Omega). After over-night incubation, cells were treated with 20 µl of 10× concentrated compound to yield indicated concentrations for each experiment. Treated cells were incubated at 37° C. for 3 days after which reagents were added to plates. After 3 days, the media with treatments were dumped and 100 µl of phenol red free DMEM with 10% CCK8 were added in each well and incubated for 1 h. The absorbance of light with the wavelength of 450 nm was measured with 800TS Absorbance Reader from the Biotech. The reading was normalized to the DMSO-treated cells, and the $IC_{50}$ values were calculated by nonlinear regression analysis using GraphPad Prism 6 software.

Flow cytometry analysis. MDA-MB-231 and MDA-MB-435 cells were plated in a 6-cm dish and double-synchronized for 18 h and then 15 h with a 9-hour release with fresh medium between them. The cells were released and treated with DMSO, Apcin and CP5V at indicated concentrations for 24 h. After treatment, the cells were collected and stained with propidium iodide (PI) staining buffer and analyzed by flow cytometry.

Figure 2A:
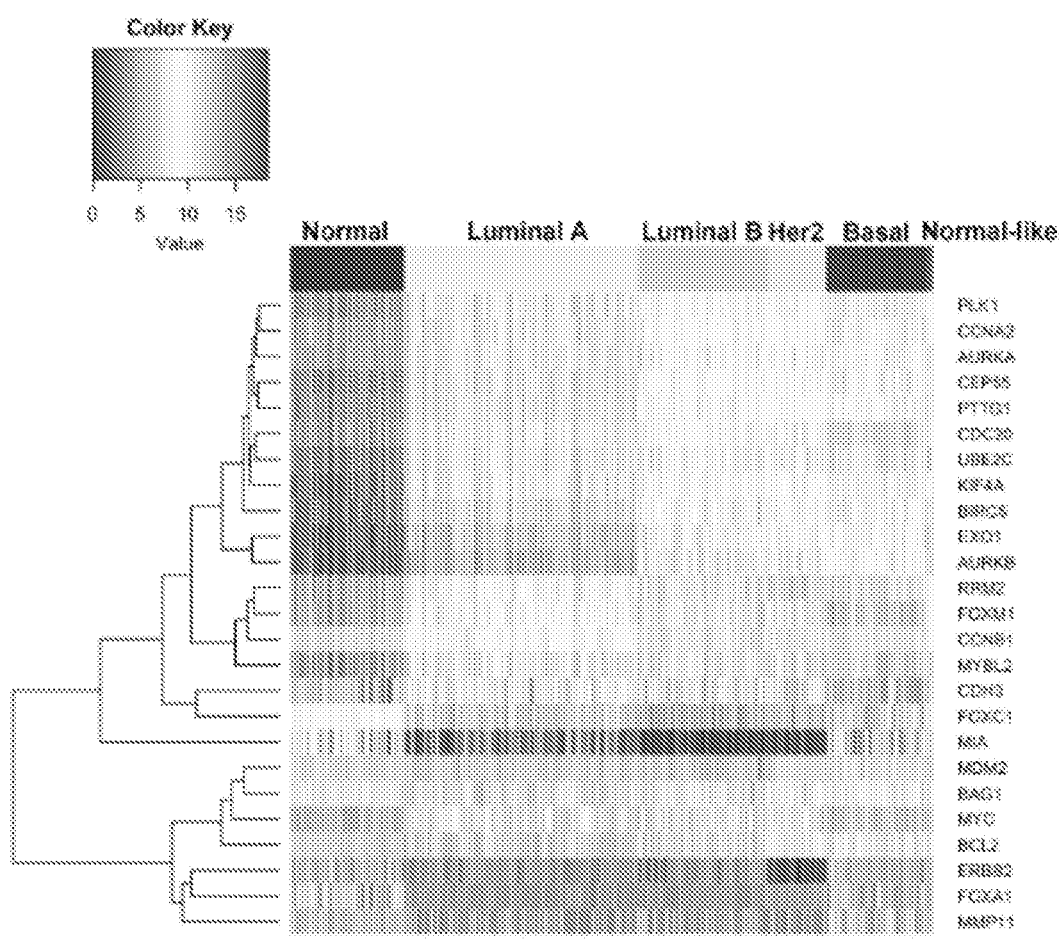
FIG. 2A shows a non-limiting example of a heatmap of the expression profile of Cdc20, Cdc20-APC/C pathway related genes, and other classic breast cancer genes. The data from TCGA was analyzed by hierarchical clustering, and red and blue colors represent higher and lower expression levels, respectively. The expression level of Cdc20 and its related genes and other critical breast cancer factors were compared between normal samples and the five PAM50 BRCA subtypes. Cdc20 expression is much higher in breast cancer compared to the normal tissue samples.
Figure 2B:
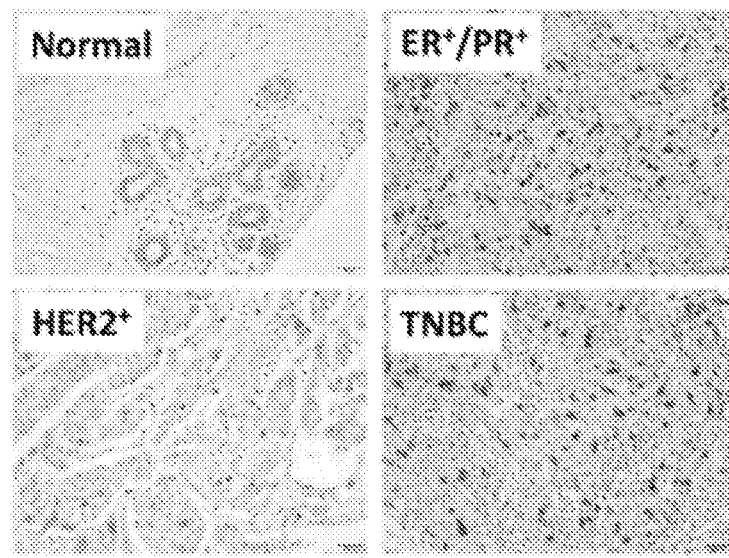
FIG. 2B shows representative Cdc20 staining in human breast cancer (ER+/PR+, estrogen receptor or progestin receptor positive breast cancer tissues; HER2+, HER2 positive breast cancer tissues; TNBC, triple-negative breast cancer tissues) and adjacent normal tissues.
Figure 2C:
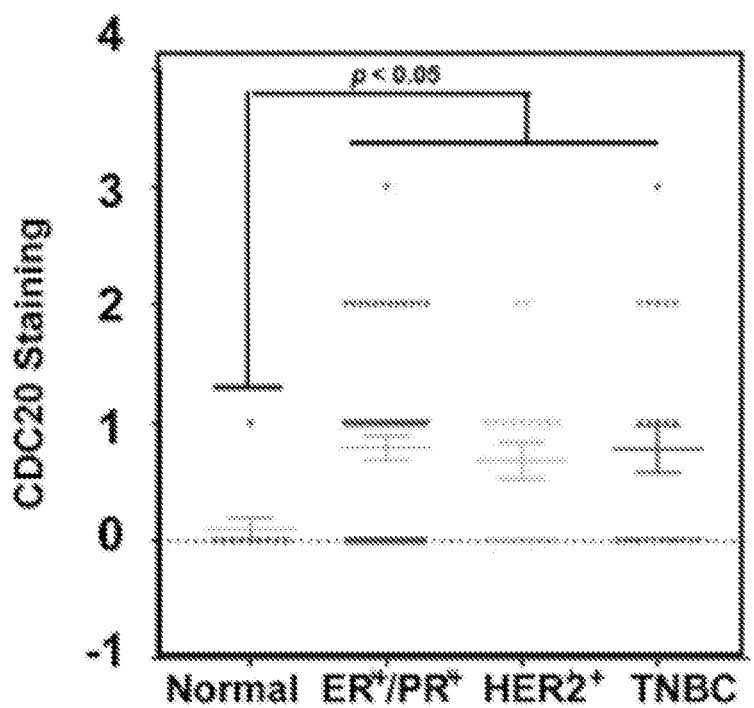
FIG. 2C shows non-limiting example of statistical analysis of the average score of Cdc20 staining among ER+/PR+, HER2+ and TNBC breast cancer tissues and corresponding non-tumor tissues, $P<0.05$ (one-way ANOVA).

Example 17. Examination of Correlation of Cdc20 Expression with Prognosis of Breast Cancer To study the clinical impact of Cdc20-APC/C in various subtypes of breast cancer, a comparison was made of the expression levels of Cdc20, Cdc20-APC/C pathway-related genes, and other classic breast cancer genes between normal tissue and various molecular subtypes of breast cancers, using expression data from TCGA database. Hierarchical clustering on the genes was applied to see if functional-related genes were clustered together. The heatmap in FIG. 2A indicates that the expression of Cdc20 in breast cancers is significantly higher compared to that in the normal tissue (t-test p-value<2.2e−16). The comparison among five subtypes of breast cancer (FIG. 2A) further reveals the subtype-dependent expression pattern of Cdc20. The basal-like breast cancer, the most aggressive and metastatic subtype, has the highest average expression level of Cdc20 (10.75), while the luminal A subtype has the lowest average expression level (8.20). As further confirmation of the importance of Cdc20 in breast cancer, immunohistochemical analyses of Cdc20 with human breast specimen were performed and severe Cdc20 protein accumulation in luminal A/B, Her2 and triple negative breast cancer (TNBC) were observed in comparison with the adjacent normal tissues (FIGS. 2B & 2C).

Figure 2D:
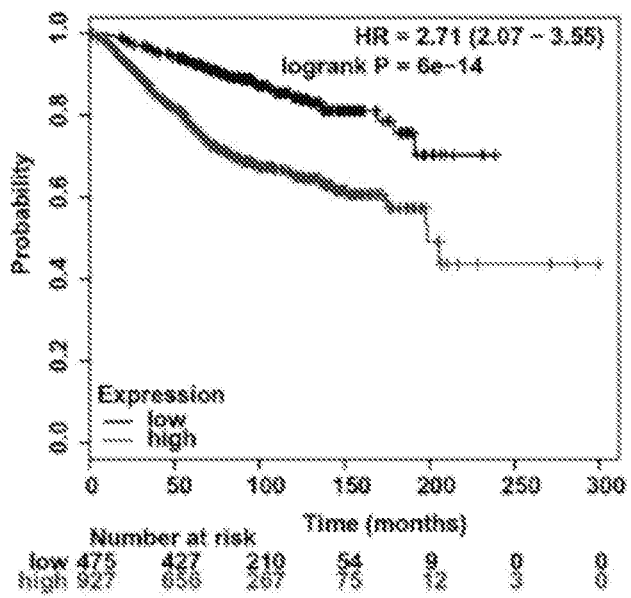
FIG. 2D and FIG. 2E show non-limiting examples of survival graphs of breast cancer based on Cdc20 expression. Relapse-free survival curves in overall breast cancer patients, patients with chemotherapy and patients with TNBC were analyzed by Cdc20 expression. HR (hazard ratio) and Log-rank P-values were calculated in KMplot database.
Figure 2E:
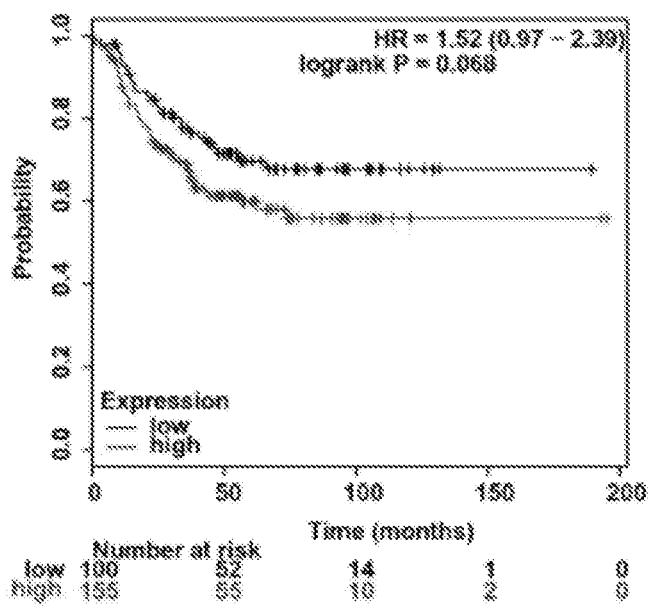

While the prognosis and survival outcomes show significant variation among different clinical subtypes, a Cox Regression model was trained to investigate the correlation between Cdc20 expression and clinical outcomes, using the expression data and survival data from a study by the Molecular Taxonomy of Breast Cancer International Consortium (METABRIC). The METABRIC dataset was used instead of the TCGA data as the former provides relatively complete survival data of close to 2,000 breast cancer patients. When Cdc20 was included as the only covariate, the coefficient of the expression level of Cdc20 in the resulting Cox model is 0.32354. This significant positive coefficient (Wald test p-value<0.001) demonstrates the positive correlation of Cdc20 expression levels with the poor prognosis. Moreover, the results from the Kaplan-Meier analyses indicate that patients with high expression of Cdc20 show significant short distant metastasis-free survival time in comparison with patients with lower Cdc20 expression (FIGS. 2D & 2E). Results from pathological studies demonstrate a strong connection between aberrant Cdc20 expression with poor prognosis of breast cancer and further suggest that targeting Cdc20 can be a good strategy for anti-mitotic therapy.

Example 18. Studies in Breast Cancer Cells

Figure 3A:
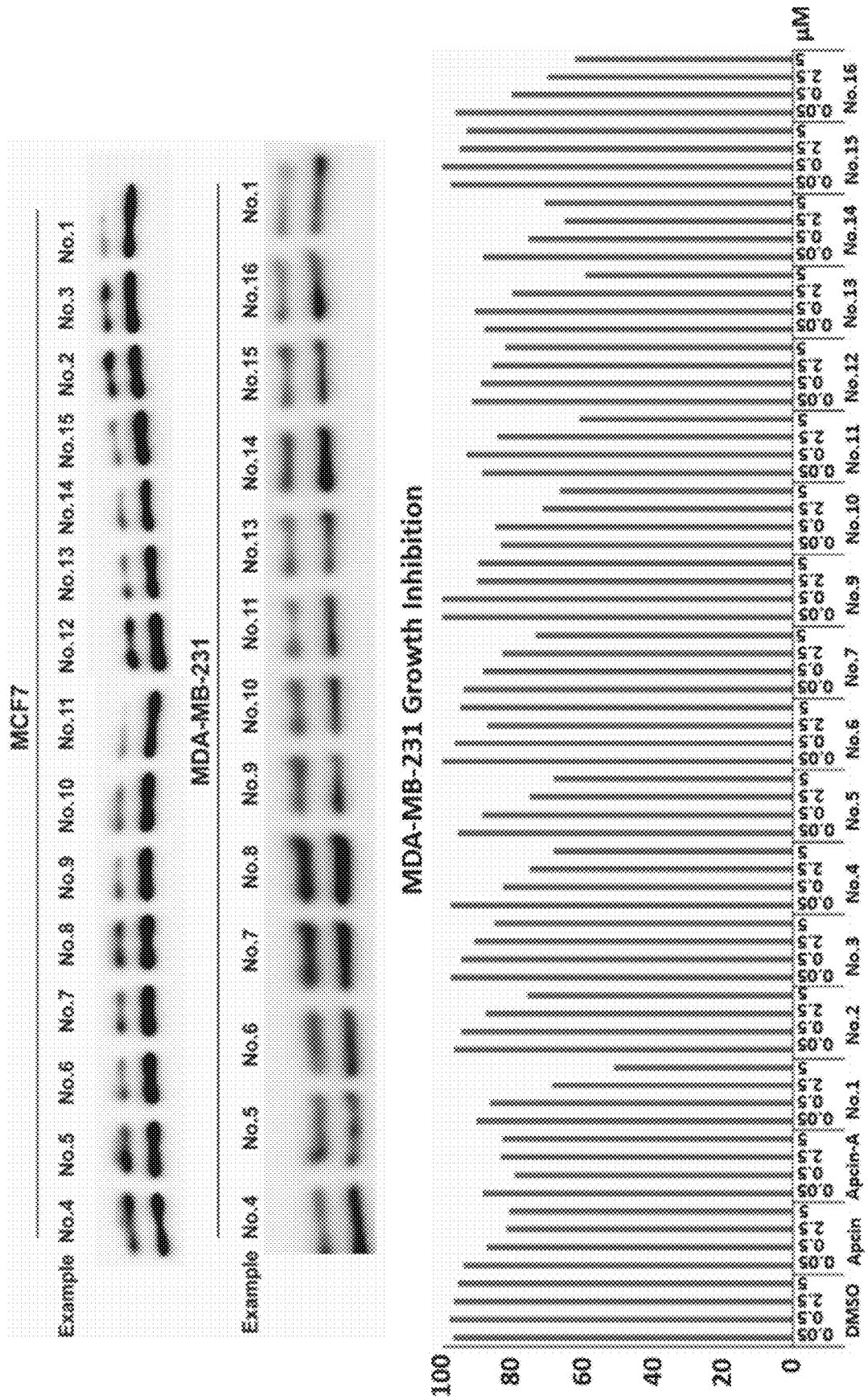
FIG. 3A shows non-limiting examples of dosage and growth inhibition analyses for 16 compounds in MCF-7 and MDA-MB-231 breast cancer cells.

The dose-dependent Cdc20 degradation effect of the compounds of Examples 1-16 in various breast cancer cells, including MCF7 and MDA-MB-231 cells, was assessed. The results (FIG. 3A) indicate that Apcin-A-PEG5-VHL1 (also referred to as CP5V) was the most potent compound in degrading Cdc20 and suppressing cancer cell growth.

Figure 3B:
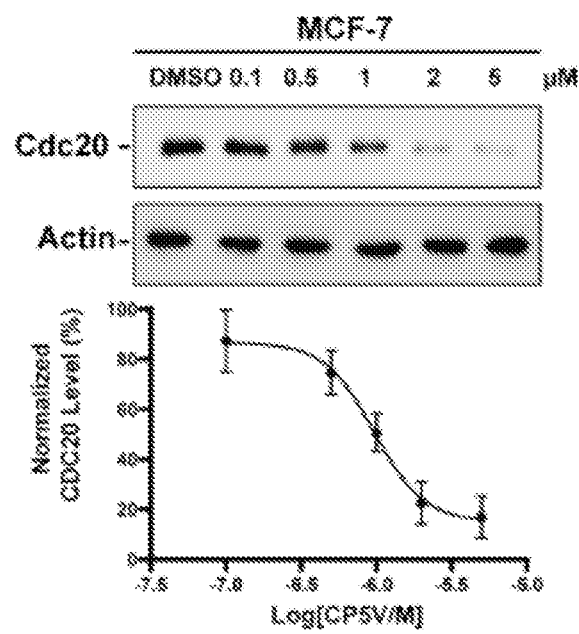
FIG. 3B shows non-limiting examples of dosage analyses for CP5V in MCF-7 breast cancer cells.
Figure 3C:
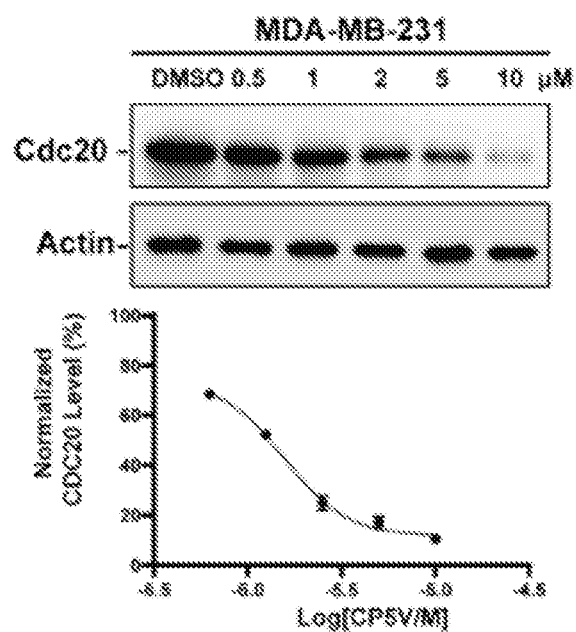
FIG. 3C shows non-limiting examples of dosage analyses for CP5V in MDA-MB-231 breast cancer cells.

To assess the effect of CP5V dosage, both MCF-7 and MDA-MB-231 cells with CP5V for 10 hours at indicated concentration (FIGS. 3B & 3C) and then cells were harvested to measure Cdc20 abundance. The results demonstrate that CP5V degrades Cdc20 in both MCF7 and MDA-MB-231 cells with a $DC_{50}$ (50% of maximum degradation) value of approximately 1.6 µM.

Figure 3D:
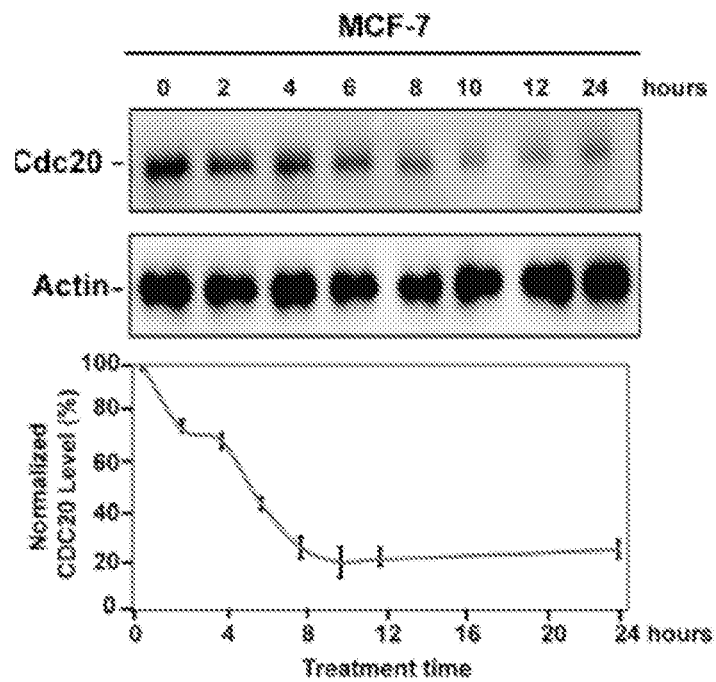
FIG. 3D shows a non-limiting example of time course measurement for CP5V-induced Cdc20 degradation in MCF-7 cells.
Figure 3E:
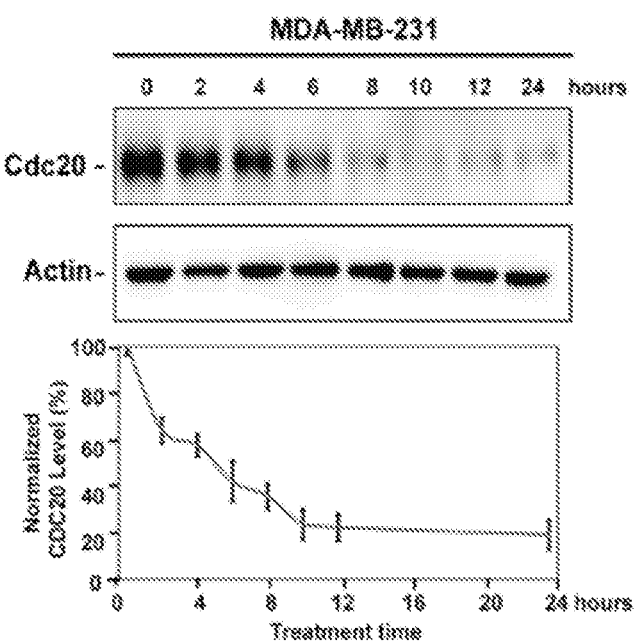
FIG. 3E shows a non-limiting example of time course measurement for CP5V-induced Cdc20 degradation in MDA-MB-231 cells.

The time course for CP5V-induced Cdc20 degradation was also measured in both cell lines. As shown in FIGS. 3D & 3E, the half-life for Cdc20 in the presence of CP5V is approximately 4 hours in both MCF-7 and MDA-MB231 cells. Apparent recovery of suppressed Cdc20 protein levels was not observed until 24 hours later (FIGS. 3D & 3E).

Figure 3F:
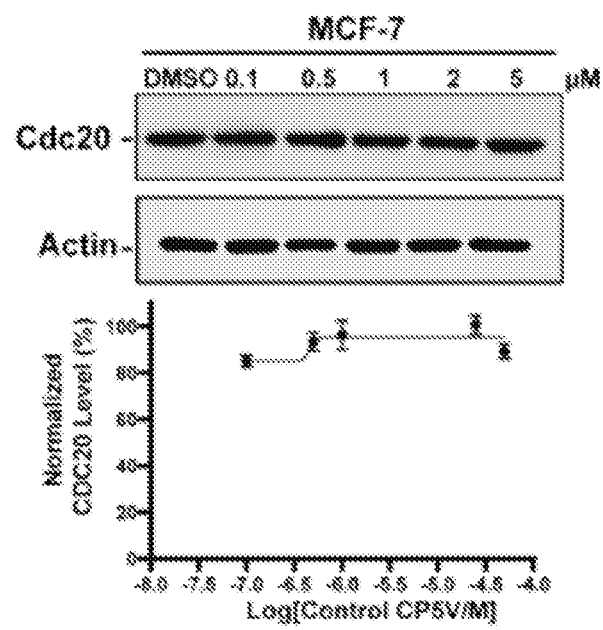
FIG. 3F shows a non-limiting example of Cdc20 protein level measurement by Western blotting of MCF-7 cells after treatment with negative control compound.
Figure 3G:
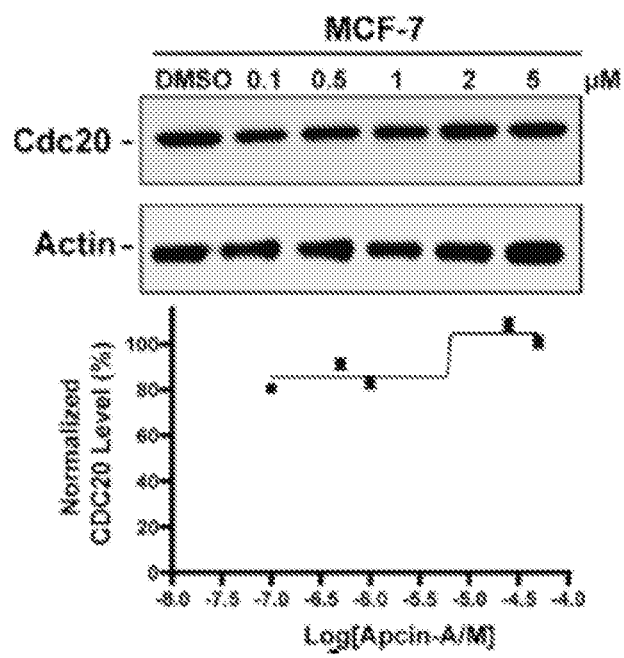
FIG. 3G shows a non-limiting example of Cdc20 protein level measurement by Western blotting of MCF-7 cells after treatment with Apcin-A. Treatment with the negative control compound or Apcin-A showed no degradation of Cdc20 at various dosages.

After determination for the potency of CP5V in Cdc20 degradation, the observed CP5V-induced Cdc20 degradation was examined for facilitation by VHL-mediated ubiquitin. To confirm that the CP5V-induced degradation of Cdc20 relies on the VHL E3 ligase, a negative control compound was designed by replacing the VHL ligand 1 with its diastereomer (Apcin-A-PEGA-VHL* of Example 8), which deactivated its interaction with VHL (Raina, Lu et al. 2016). As shown in FIGS. 3F & 3G, no effect of Cdc20 protein change in the presence of negative control compound was observed, suggesting that VHL plays an important role in the CP5V-induced Cdc20 degradation.

Figure 3H:
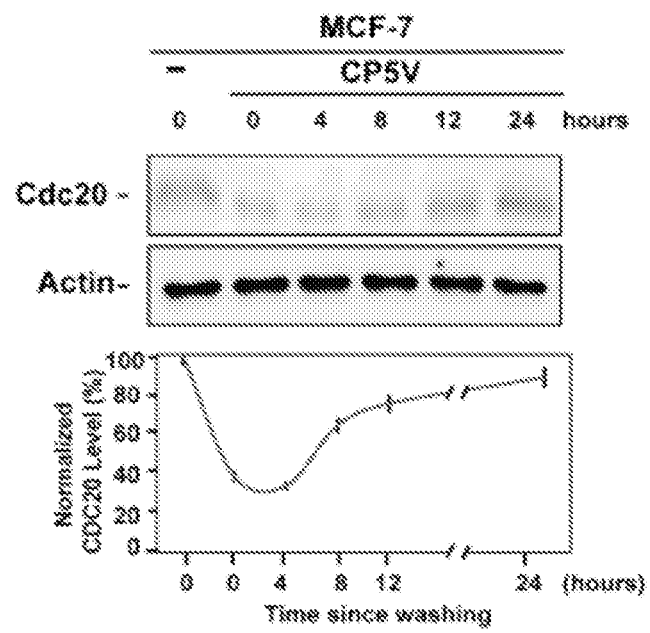
FIG. 3H shows a non-limiting example of Cdc20 protein level measurement by Western blotting of MCF-7 cells after treatment with CP5V.
Figure 3I:
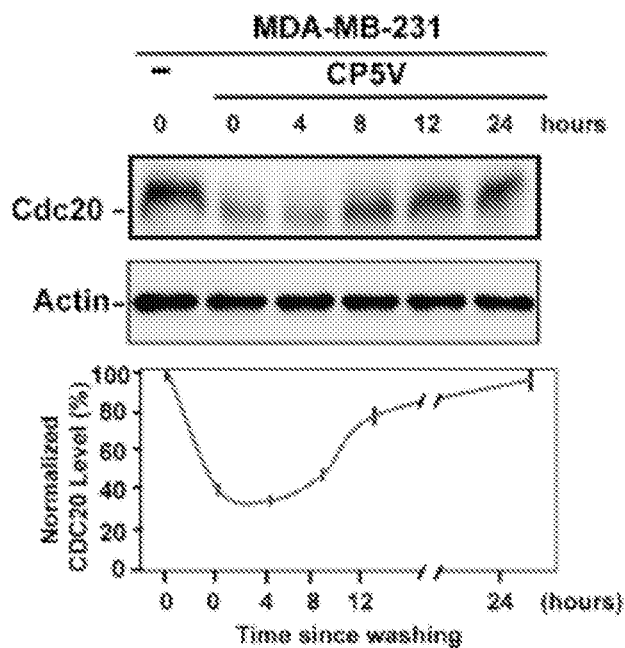
FIG. 3I shows a non-limiting example of Cdc20 protein level measurement by Western blotting of MDA-MB-231 cells after treatment with CP5V. The MCF-7 and MDA-MB-231 cells were treated with CP5V at 2 µM for 8 hours followed by release in fresh medium. Cells were collected at different time points (0, 4, 8, 12, 24 hours) for measuring Cdc20 protein levels by Western blotting.

To test how the abundance of Cdc20 would change after removing CP5V from the medium, the breast cancer cells were treated with CP5V and then CP5V was removed followed by replacement with fresh medium. FIGS. 3H & 3I show the fluctuation of Cdc20 protein level recovery in 24 h after withdrawing CP5V.

Figure 3J:
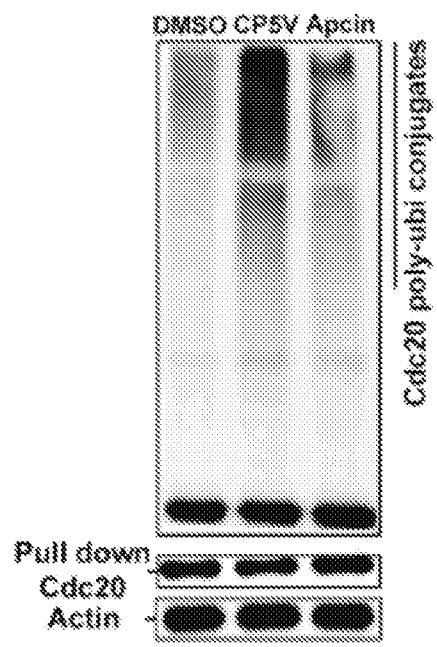
FIG. 3J shows a non-limiting example of CP5V targeting Cdc20 for degradation through ubiquitylation. MDA-MB-231 cells were treated with 2 µM CP5V for 6 hours in the presence of 5 µM MG-132. Cdc20 were immunoprecipated by antibody against Cdc20 followed by immunoblotting using anti-ubiquitin antibody.

To confirm the CP5V-induced degradation of Cdc20 is mediated through the ubiquitin-proteasome pathway, the Cdc20 ubiquitylation in the absence and presence of CP5V as well as Apcin-A was measured. MDA-MB-231 cells were treated with either 2 µM CP5V or 2 µM Apcin-A and added MG-132 at the same time. As shown in FIG. 3J, CP5V enhances Cdc20 ubiquitylation, while no obvious effect was observed in response to Apcin-A.

Figure 8:
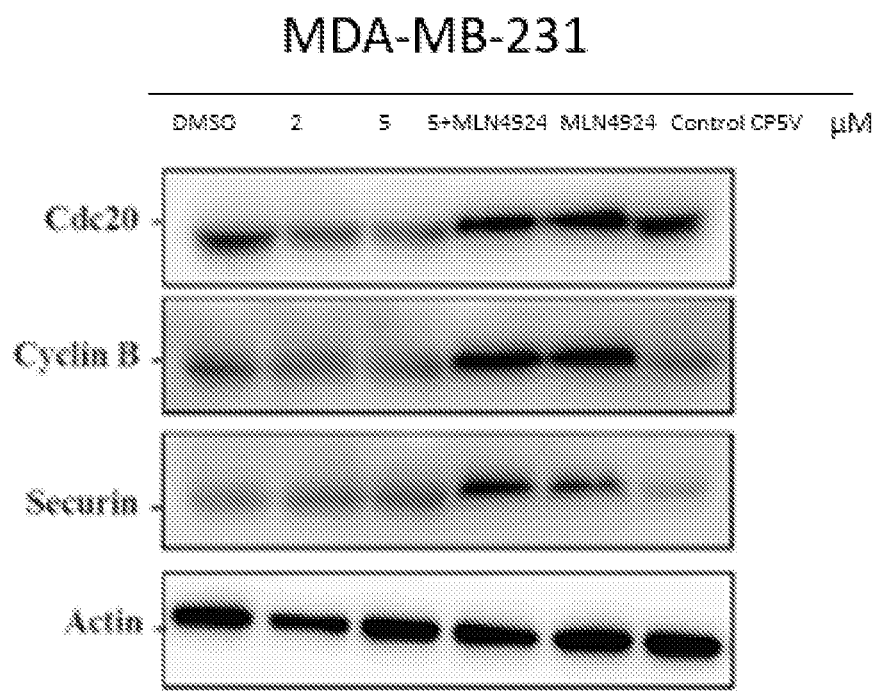
FIG. 8 shows the inhibition of CP5V-mediated Cdc20 degradation with MLN4924. MDA-MB-231 cells were treated with CP5V or CP5V and MLN4924 (5 μM) at the indicated dose for 10 hours. Cdc20, cyclin B, securin, and actin levels were determined by Western blotting.

VHL complex (EloB/EloC-Cul2/5-RBX1-VHL) belongs to Cullin-RING-ligase (CRL) family target HIF-α and other substrate protein for ubiquitylation. Given that activation of Cullin E3 ligase is often involved in neddylation, it was examined if CP5V-induced Cdc20 degradation is sensitive to neddylation inhibitor MLN4924. MDA-MB-231 cells were treated with MLN4924, which can inactivate CRLs by inhibiting cullin neddylation. As shown in FIG. 8, the treatment of MLN4924 inhibited the degradation of Cdc20 caused by CP5V.

Figure 9:
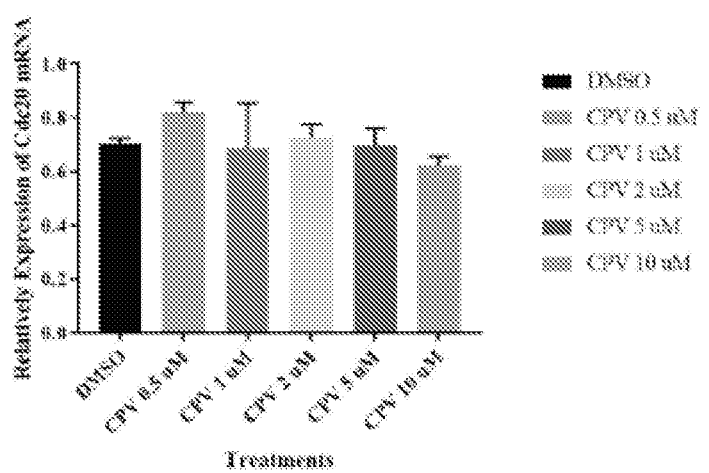
FIG. 9 shows relative RNA expression in MDA-MB-231 cells treated with CP5V. MDA-MB-231 cells treated with CP5V at indicated dosages for 10 hours were harvested for RNA extraction, reverse-transcription, and further qRT-PCR.

To further confirm the conclusion that the CP5V-medicated degradation is depending on the ubiquitin-proteasome system, RT-PCR was conducted to measure the alteration of Cdc20 RNA levels in response to CP5V treatment. As shown in FIG. 9, no significant change of Cdc20 mRNA level was observed, confirming that the CP5V-induced Cdc20 protein level drop off is achieved through the post-translational modifications.

Figure 10:
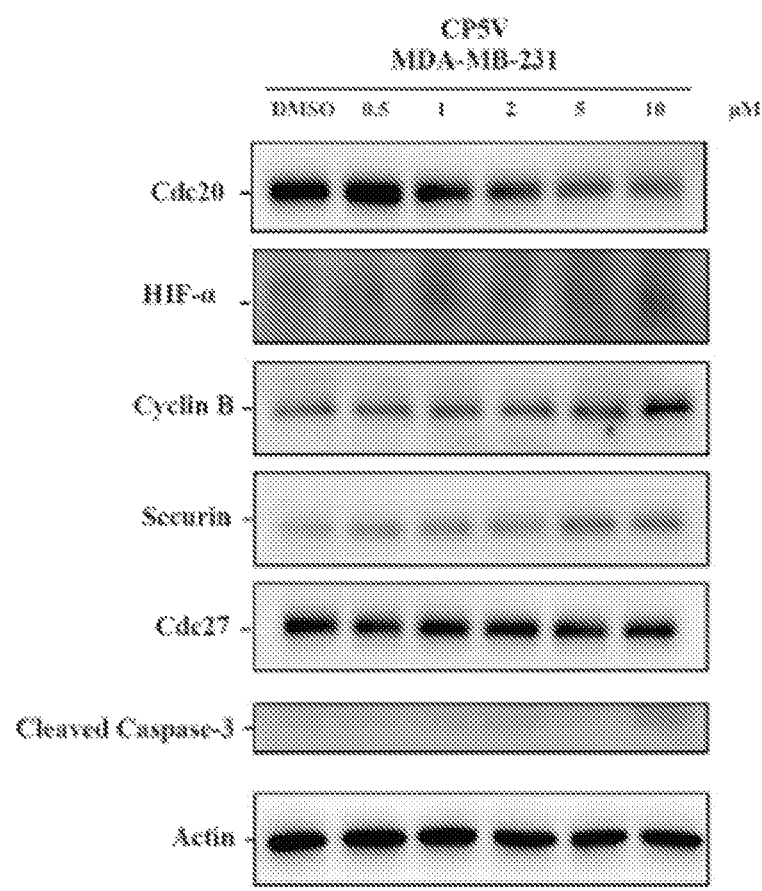
FIG. 10 shows selective degradation of Cdc20 by CP5V without causing an apparent accumulation of HIF-α in MDA-MB-231 cells. MDA-MB-231 cells treated with CP5V at indicated dosages for 10 hours were harvested for Western Blot.

To test the specificity for CP5V in targeting Cdc20, the dosage experiment based on MDA-MB-231 cells was repeated and the alteration of protein levels for Cdc20 and Cdc27, another core subunit of anaphase-promoting complex, was measured. As shown in FIG. 10, while CP5V causes a decrease of Cdc20, no Cdc27 protein level change was observed, suggesting that CP5V selectively induces Cdc20 degradation.

Taken together, the above characterization demonstrates that CP5V explicitly induces Cdc20 for degradation through the VHL-mediated ubiquitylation and proteasomal pathway.

Example 19. Study of Changes in Protein Levels of Securin and Cyclin B1

Figure 4A:
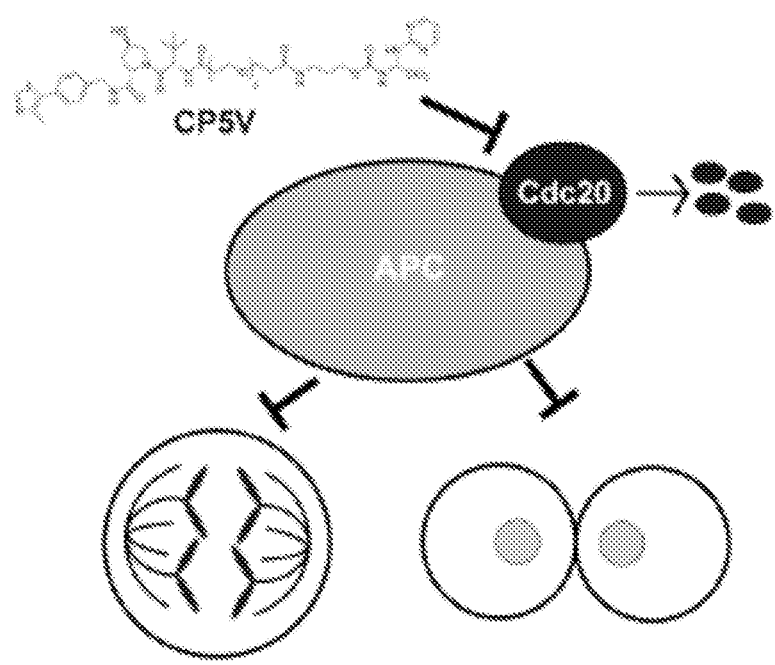
FIG. 4A shows a schematic diagram of targeting Cdc20 for degradation by CP5V leading to inhibition of chromatid separation and the exit of mitosis.
Figure 4B:
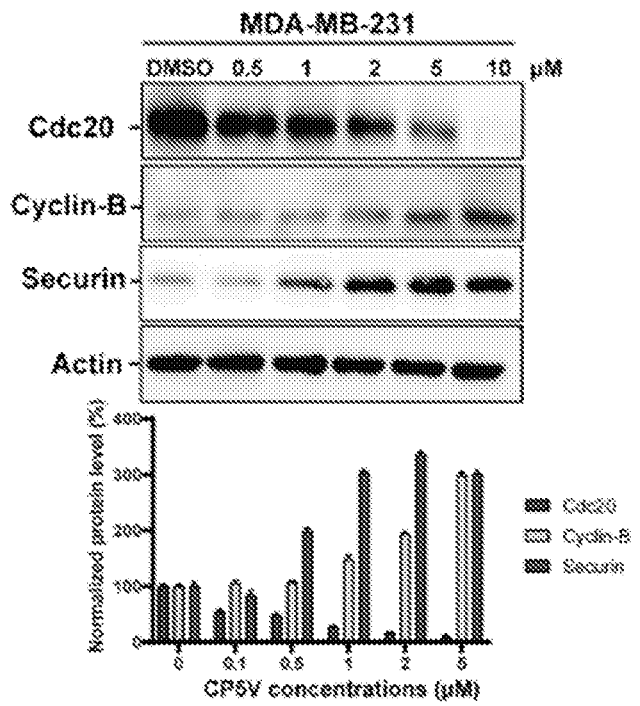
FIG. 4B shows a non-limiting example of CP5V-mediated Cdc20 degradation resulting in accumulation of cyclin B. MDA-MB-231 cells were treated with CP5V at the indicated dose for 10 hours. Cdc20 and cyclin-B levels were then determined by Western blotting.
Figure 4C:
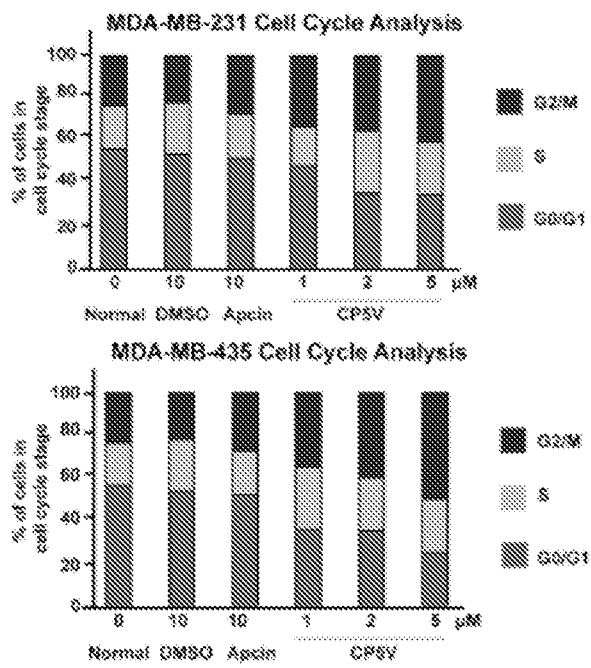
FIG. 4C shows a non-limiting example of CP5V inducing mitotic arrest. In this example, cell cycle analysis of MDA-MB-231 cells was performed after CP5V treatment. The MDA-MB-231 cells were initially synchronized by double-thymidine followed by treatment with CP5V for 16 hours. Cell cycle profile was then measured by flow cytometry.
Figure 4D:
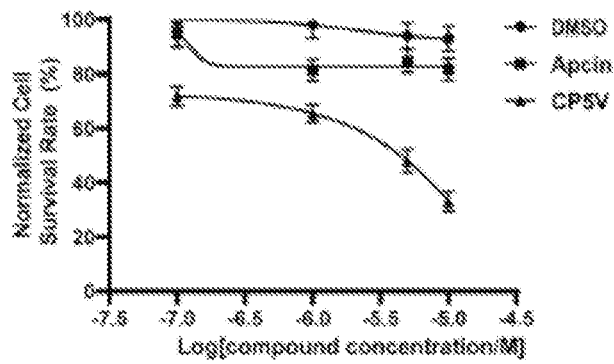
FIG. 4D shows a non-limiting example of CP5V causing inhibition of cell growth in MDA-MB-231 and MDA-MB-435 cells. In this example, MDA-MB-231 cells were plated in 96-well plates at the concentration of 3000 cells/well and treated with DMSO, Apcin and CP5V for 72 h and the cell survival activity was measured by CCK8 assay.
Figure 4D:
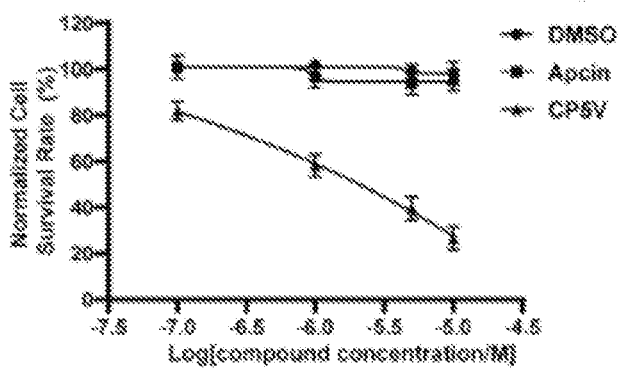
Figure 4D:
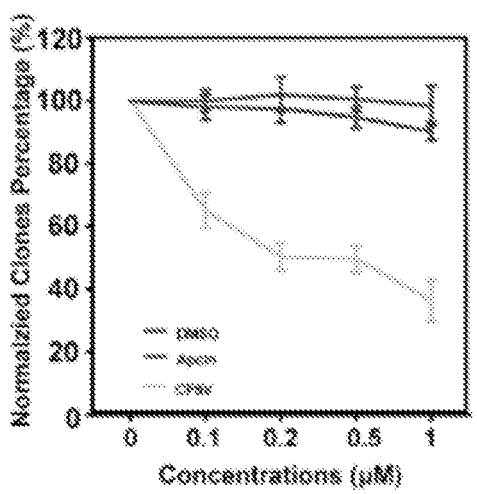

Given that Cdc20-APC/C regulates mitotic progression through proteolysis of securin and cyclin B1, CP5V-mediated degradation of Cdc20 was examined for resultant changes of the protein level of securin and cyclin B1. It was observed that, as Cdc20 underwent degradation, the cyclin B1 largely accumulated in cells (FIG. 4B). Moreover, flow cytometry analysis to measure the cell cycle distribution of breast cancer cells after the treatment with CP5V indicated that CP5V induces mitotic arrest in MDA-MD-231 and MDA-MB-435 cells, while there was no effect with Apcin alone (FIG. 4C). With 2 µM of CP5V, over 40% of the MDA-MB-231 cells and 50% of MDA-MB-435 cells were arrested in the G2/M phase. The fraction of cells in the G0/G1 phase were much lower compared to control cells, which indicates that the mitotic exit is restricted. Furthermore, CP5V inhibits cell growth in various triple negative breast cancer cell lines (FIG. 4D) with $IC_{50}$ 2.6 µM for MDA-MB-231 cells and 1.99 µM for MDA-MB-435 cells.

Example 20. Study of CP5V in Clonogenic Assay

Figure 4E:
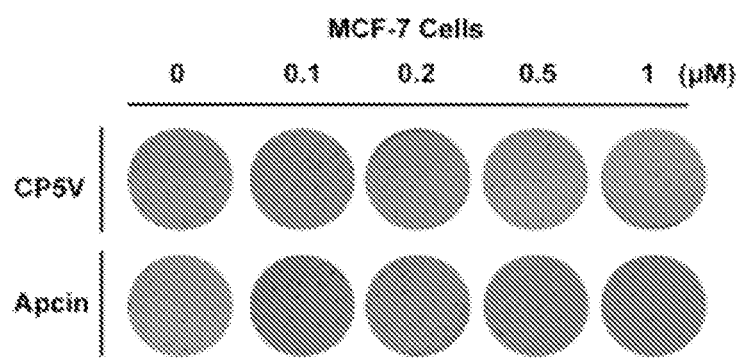
FIG. 4E shows a non-limiting example of a clonogenic assay demonstrating the effect of CP5V on MCF7 cells. 200 MCF7 cells were plated in 6-well plate and treated with CP5V at gradient concentrations (0.1, 0.2, 0.5, 1 µM) for 24 hours following culture for 2 weeks. To quantify the colony formation, the cells were stained with crystal violet and the numbers of colonies were counted and quantified by Image J. Left panel shows the representative clones. Right panel shows the statistical results. Data are presented as the mean±standard error of the mean (S.E.) of three independent samples (**$p<0.01$).

The efficacy of CP5V in killing breast cancer cells was examined by using a clonogenic assay (Franken, Rodermond et al. 2006). MCF7 cells were plated in a 6-well plate at the concentration of 200 cells per well and treated with CP5V at gradient concentrations (0.1, 0.2, 0.5, 1 µM) for 24 hours followed by culturing them for 2 weeks. To quantify the colony formation, the cells were stained with crystal violet and the number of colonies was quantified by ImageJ. CP5V demonstrated its potent efficacy in killing breast cancer cells at 1 µM (FIG. 4E).

Figure 11:
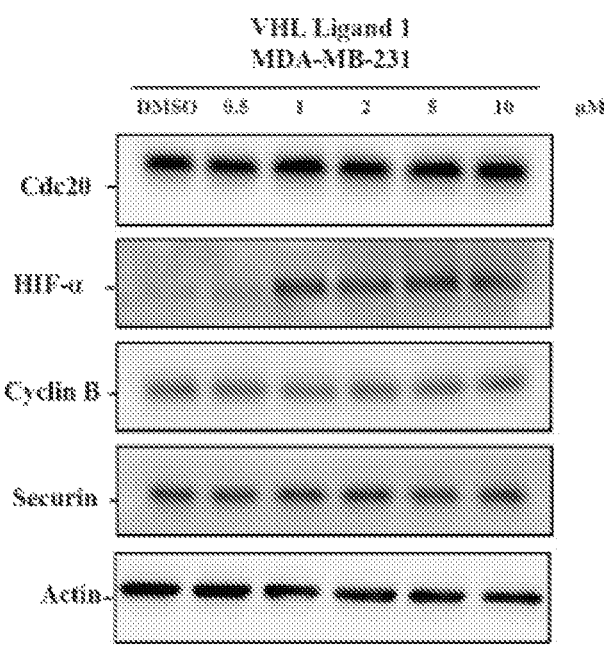
FIG. 11 shows VHL Ligand 1 induced HIF-α accumulation with a concentration higher equal or than 1 μM in MDA-MB-231 cells. MDA-MB-231 cells treated with VHL Ligand 1 at indicated dosages for 10 hours and collected for WB.
Figure 12A:
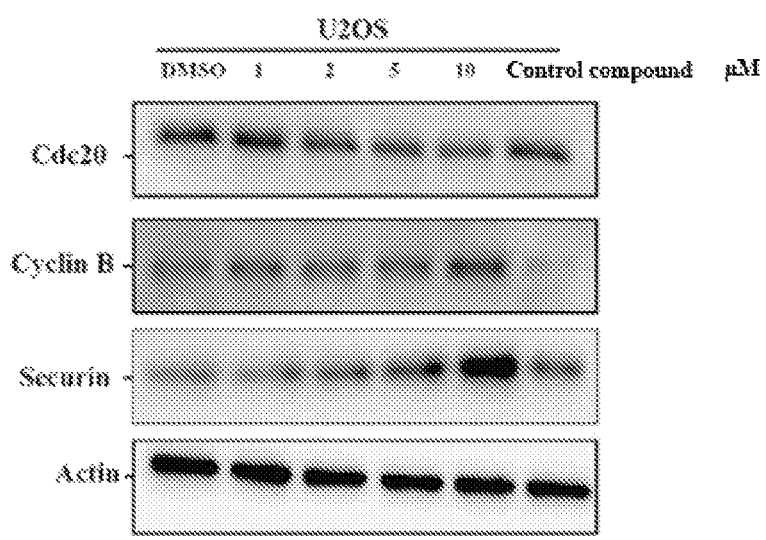
FIG. 12A shows dosage dependency of CP5V action in U2OS (Osteosarcoma cell line). The cancer cells were treated with CP5V with indicated dosages for 10 hours and collected for WB. The control compound is the negative control compound of Example 8.
Figure 12B:
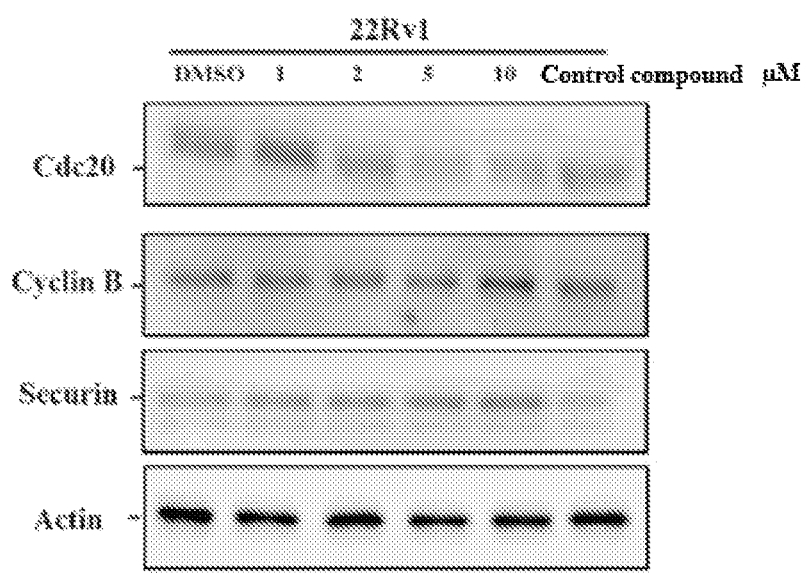
FIG. 12B shows dosage dependency of CP5V action in 22Rv1. The cancer cells were treated with CP5V with indicated dosages for 10 hours and collected for WB. The control compound is the negative control compound of Example 8.
Figure 12C:
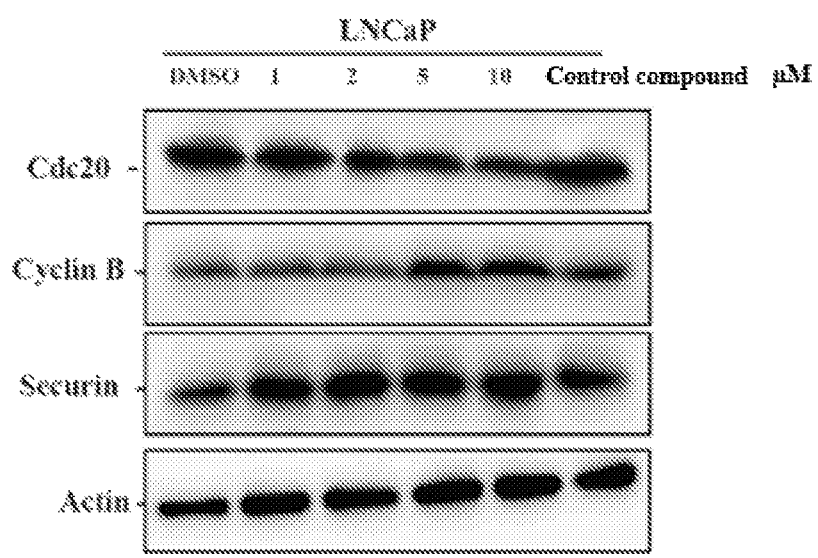
FIG. 12C shows dosage dependency of CP5V action in LNCaP cells (Prostate cancer cell lines). The cancer cells were treated with CP5V with indicated dosages for 10 hours and collected for WB. The control compound is the negative control compound of Example 8.
Figure 12D:
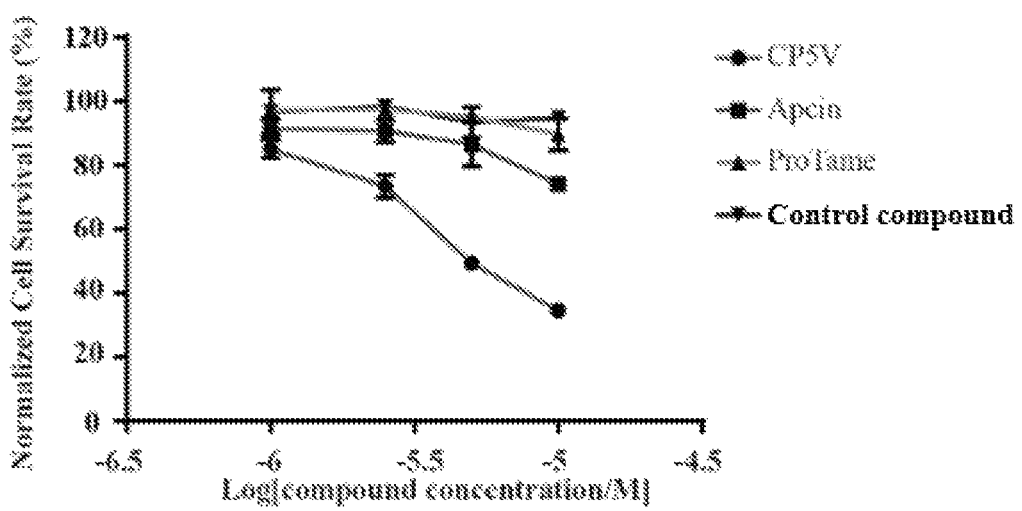
FIG. 12D shows that CP5V causes significant inhibition of cell growth in U2OS cells. The cancer cells were plated in 96-well plates at the concentration of 3000 cells/well and treated with DMSO, apcin, ProTame, and CP5V for 72 hours and the cell survival activity was measured by CCK8 assay. The test was performed in triplicate (n=3). Data are mean±SEM. The control compound is the negative control compound of Example 8.
Figure 12E:
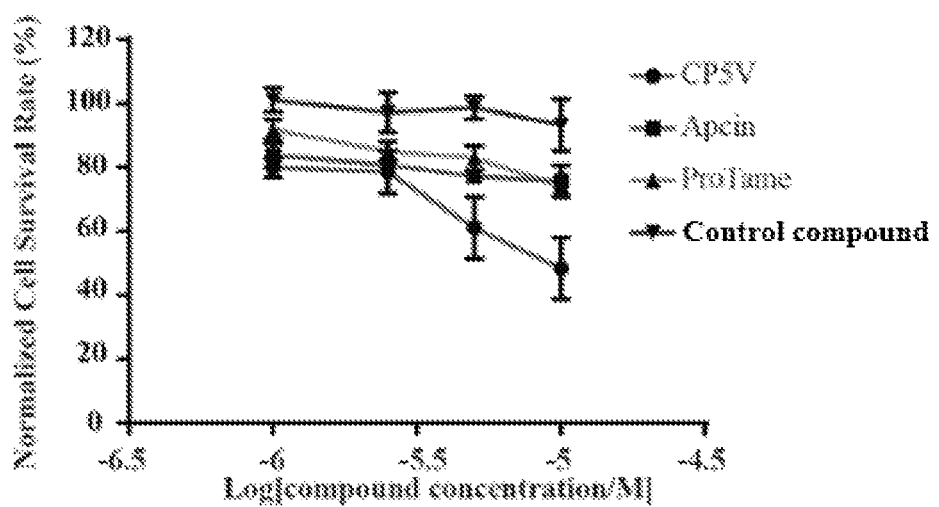
FIG. 12E shows that CP5V causes significant inhibition of cell growth in 22Rv1 cells. The cancer cells were plated in 96-well plates at the concentration of 3000 cells/well and treated with DMSO, apcin, ProTame, and CP5V for 72 hours and the cell survival activity was measured by CCK8 assay. The test was performed in triplicate (n=3). Data are mean±SEM. The control compound is the negative control compound of Example 8.
Figure 12F:
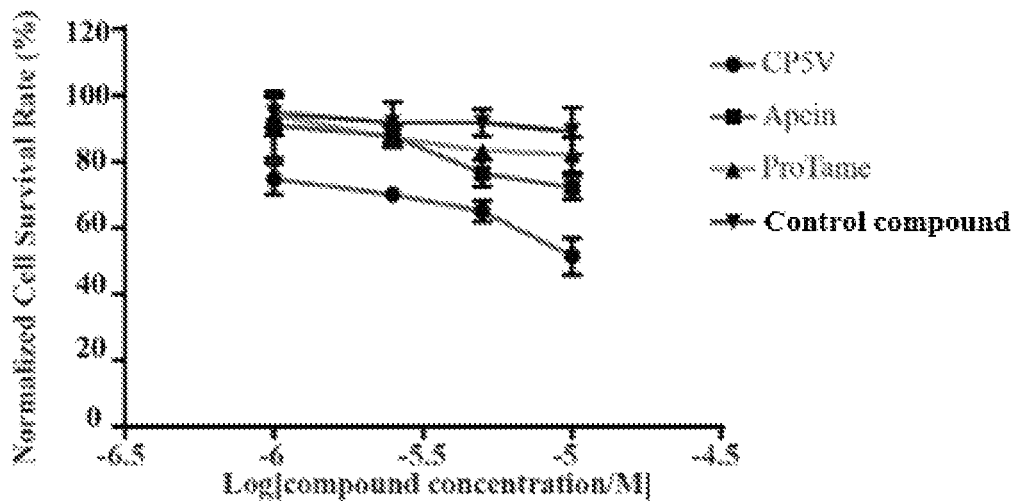
FIG. 12F shows that CP5V causes significant inhibition of cell growth in LNCaP cells. The cancer cells were plated in 96-well plates at the concentration of 3000 cells/well and treated with DMSO, apcin, ProTame, and CP5V for 72 hours and the cell survival activity was measured by CCK8 assay. The test was performed in triplicate (n=3). Data are mean±SEM. The control compound is the negative control compound of Example 8.
Figure 13A:
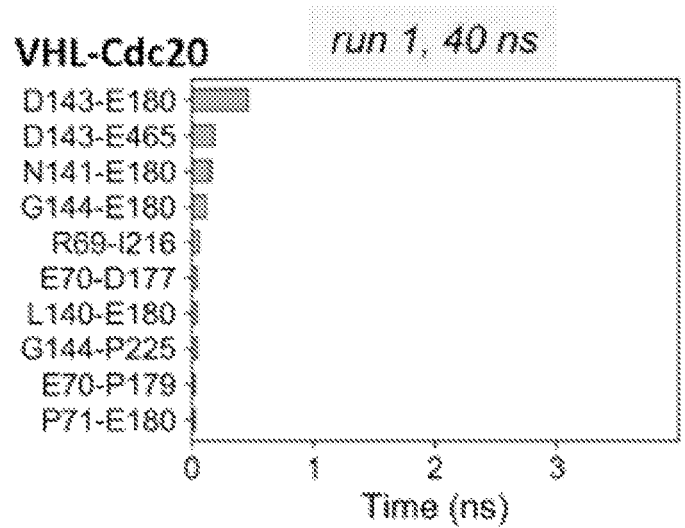
FIGS. 13A, 13B, 13C, 13D, 13E, 13F, 13G, 13H, and 13I show intermolecular residue-residue interactions between VHL and Cdc20 observed in six independent molecular dynamics (MD) simulations. Simulations were performed for the pair of proteins VHL-Cdc20 linked by CP5V, starting from different initial orientations. The plots display the total time during which the residue pairs indicated along the ordinate made intermolecular contacts. Contacts are defined when residue pairs (left for VHL and right for Cdc20) have any two heavy atoms separated by less than 4.0 Å. Results are displayed for runs (FIG. 13A) 1, (FIG. 13B) 2, (FIG. 13C) 3 and (FIG. 13D) 6, each of 40 ns. We also performed a long run of 200 ns (run 5) displayed in five panels.
Figure 13B:
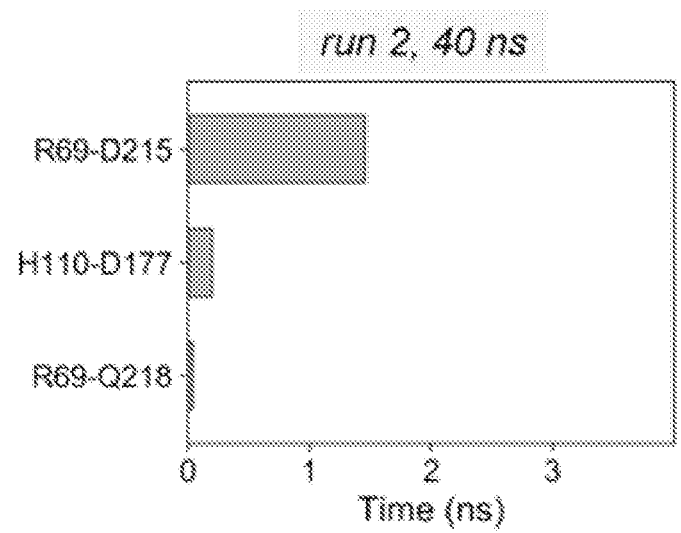
Figure 13C:
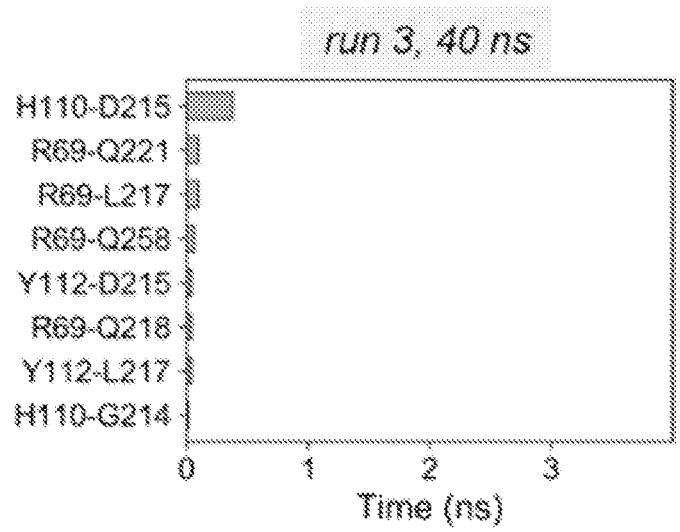
Figure 13D:
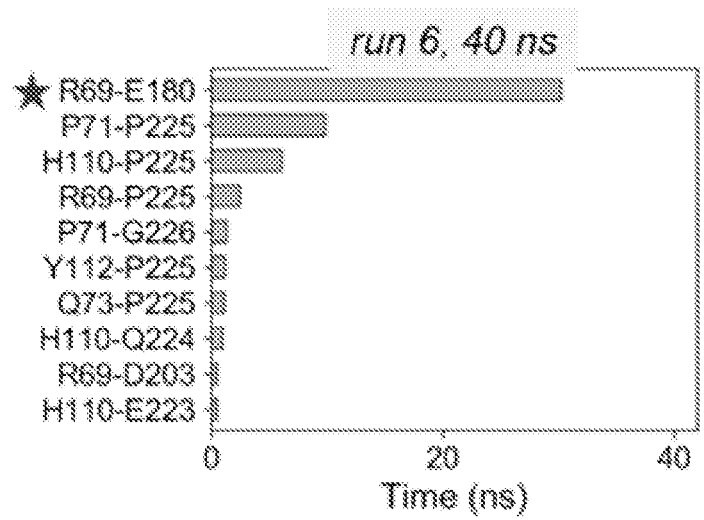
Figure 13E:
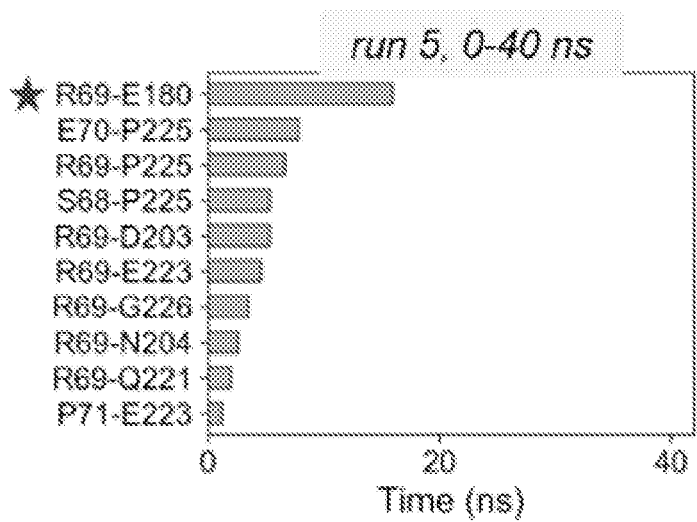
Figure 13F:
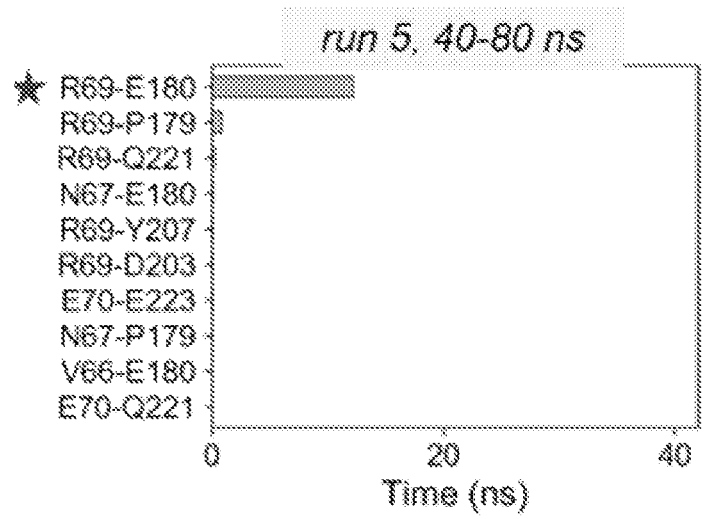
Figure 13G:
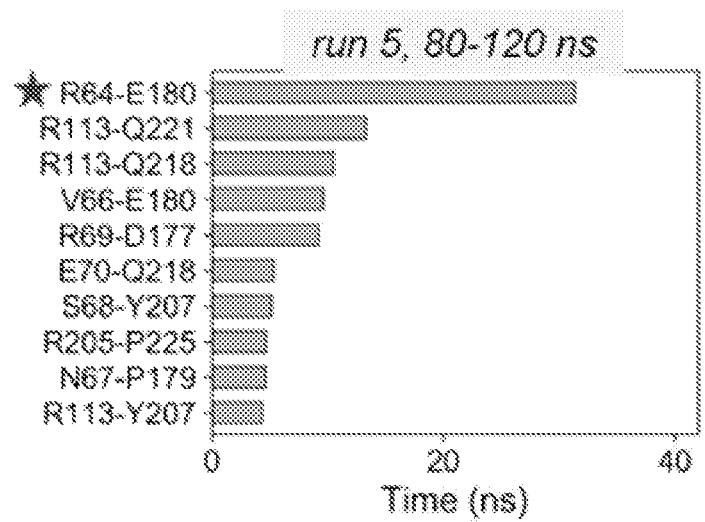
Figure 13H:
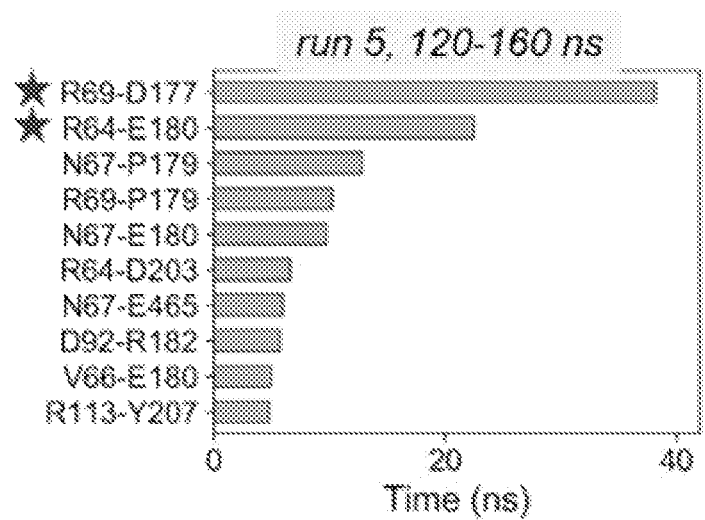
Figure 13I:
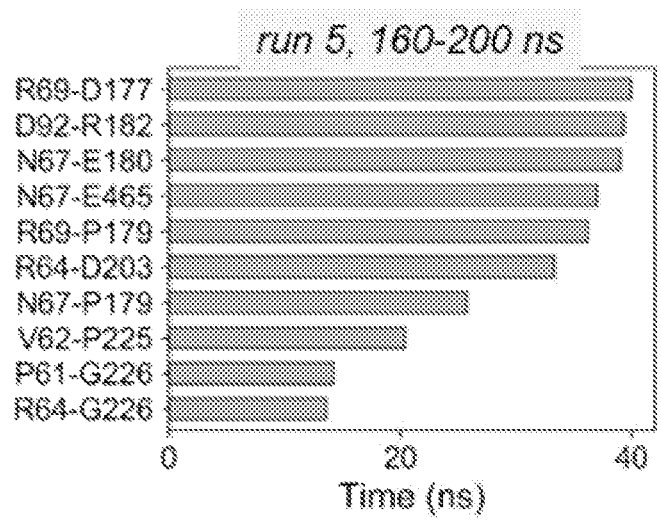

Relatively high potential dosage of VHL ligand 1 (VHL1), the VHL-binding moiety offered by CP5V, causes concern if it affects HIF1α, the substrate of VHL. To test the possible change of HIF1α caused by the VHL ligand 1 itself and CP5V, MDA-MB-231 cells were treated with either the VHL ligand 1 or CP5V. As shown in FIGS. 10 & 11, while significant HIF1α is accumulated in response to the VHL ligand 1, no obvious alteration of HIF1α is observed in response to CP5V treatment.

The effect of CP5V was tested in three different cancer cell lines including U2OS (osteosarcoma cell), 22Rv1 (prostate carcinoma cell) and LNCaP (prostate carcinoma cell). As shown in FIGS. 12A-12F, CP5V demonstrated its ability to induce Cdc20 degradation and growth inhibition in all tested cancer cell lines, suggesting a broad effect of CP5V in various cancer type cells.

Collectively, these validation experiments demonstrate that CP5V inhibits mitotic progression and induces cancer cell growth inhibition and death.

Example 21. Examination of CP5V and Taxane-Resistance

Figure 4F:
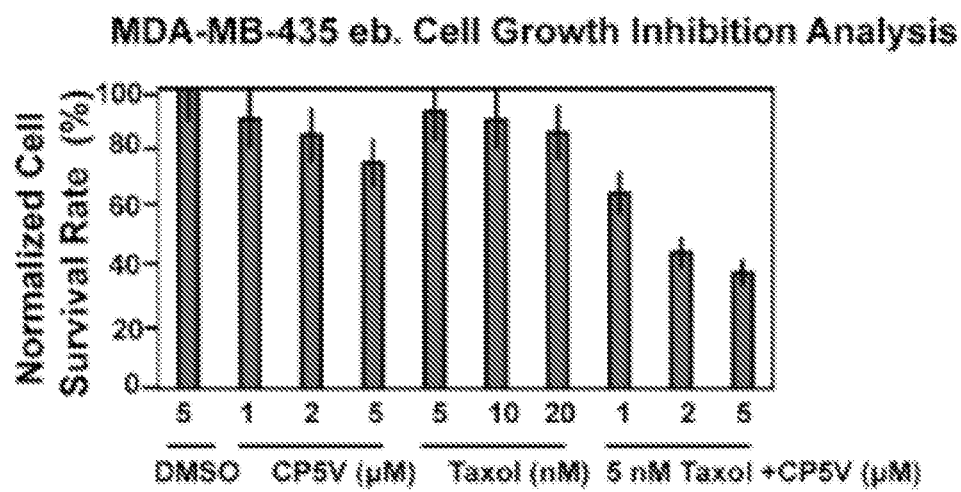
FIG. 4F shows a non-limiting example of CP5V restoring the Taxol-induced cytotoxic response for the Taxol-resistant cells.
Figure 4G:
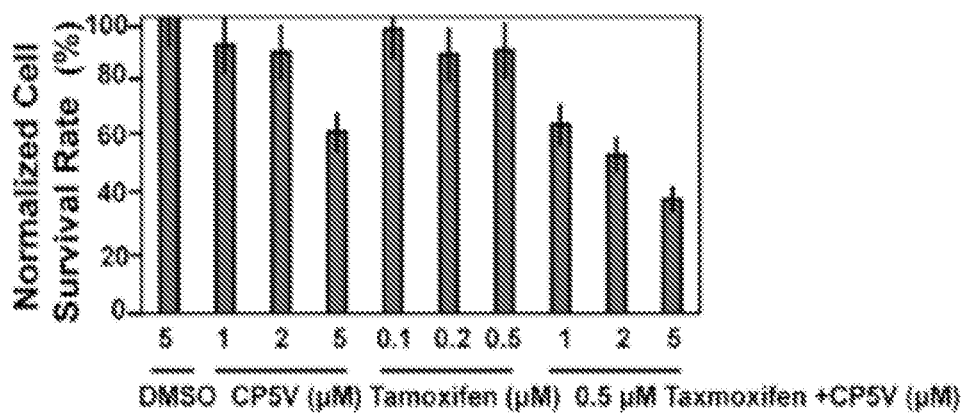
FIG. 4G shows a non-limiting example of CP5V rescuing the endocrine response for Tamoxifen-resistant cancer cells.

To examine whether CP5V can overcome taxane resistance and facilitate taxane-induced cell death, the combinational effect of CP5V and paclitaxel against Taxol-resistant cell line MDA-MB-435 eb, whose tolerance against paclitaxel is up to 20 nM, was examined. FIG. 4F shows that about 92% of MDA-MB-435 eb cells survived in the presence of 5 nM paclitaxel, but CP5V significantly restored their Taxol-cytotoxic response. The synergistic effect of 5 µM of CP5V and 5 nM of paclitaxel caused more than 50% of the growth inhibition of MDA-MB-435 eb cells, compared to less than 10% inhibition with 5 nM of paclitaxel alone. CP5V also re-sensitizes Tamoxifen-resistant breast cancer cells to Tamoxifen treatment (FIG. 4G).

Example 22. Molecular Modeling

Figure 5A:
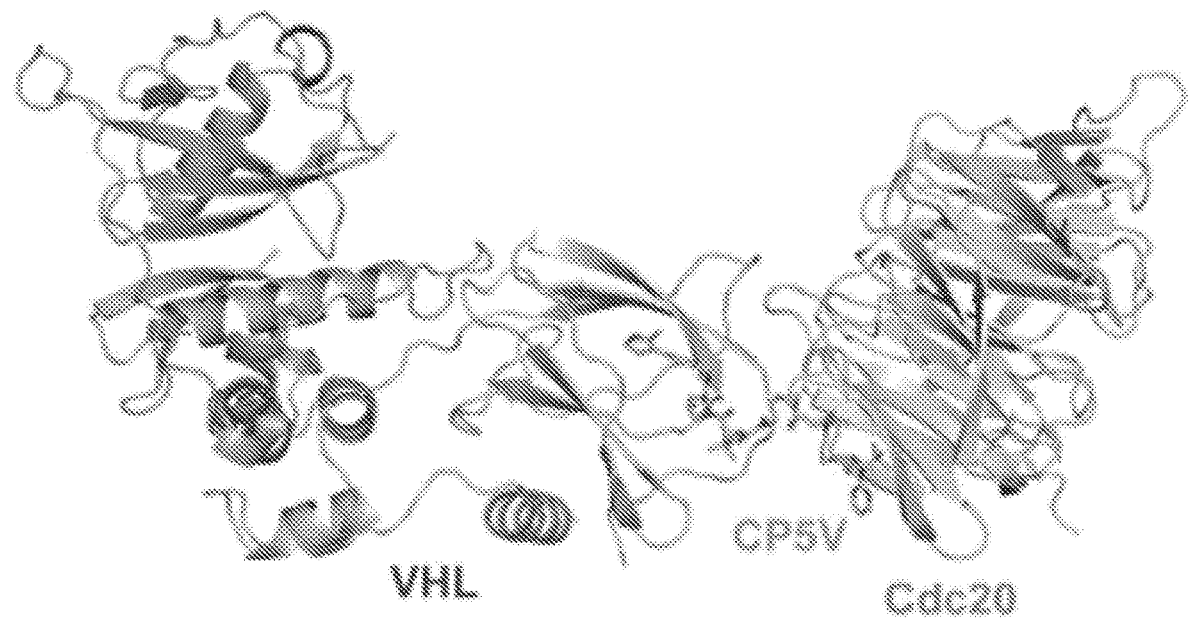
FIG. 5A shows a non-limiting example of a modeled structure of CP5V-ElonginC-ElonginB complex. The structure of Cdc20 and docking pose of the Apcin-A portion of CP5V are taken from PDB 4N14. The Apcin-A portion binds to the D-box binding site of Cdc20. The structures of VHL-ElonginC-ElonginB and docking pose of the VHL ligand part of the CP5V are taken from PDB 5T35.
Figure 5B:
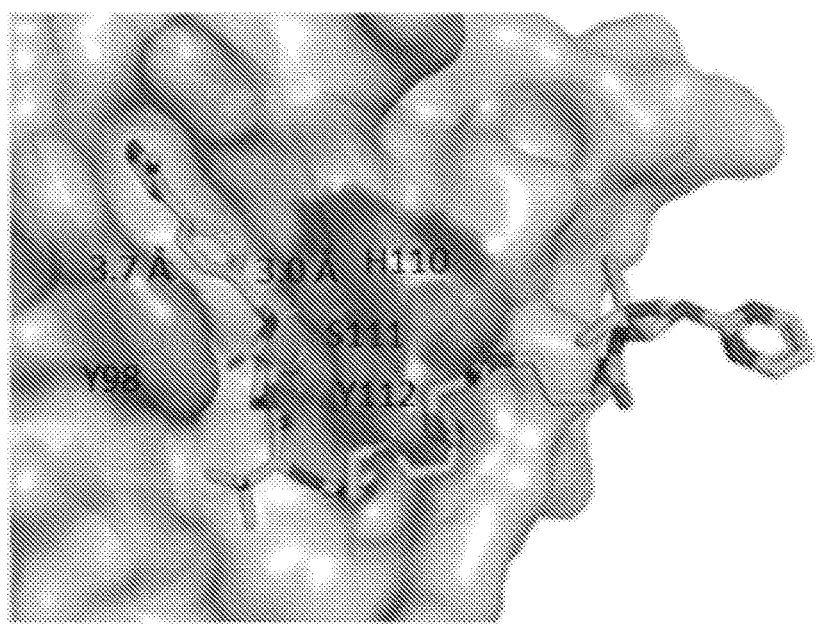
FIG. 5B shows a non-limiting example of the interaction between CP5V and VHL according to the model shown in FIG. 5A.
Figure 5C:
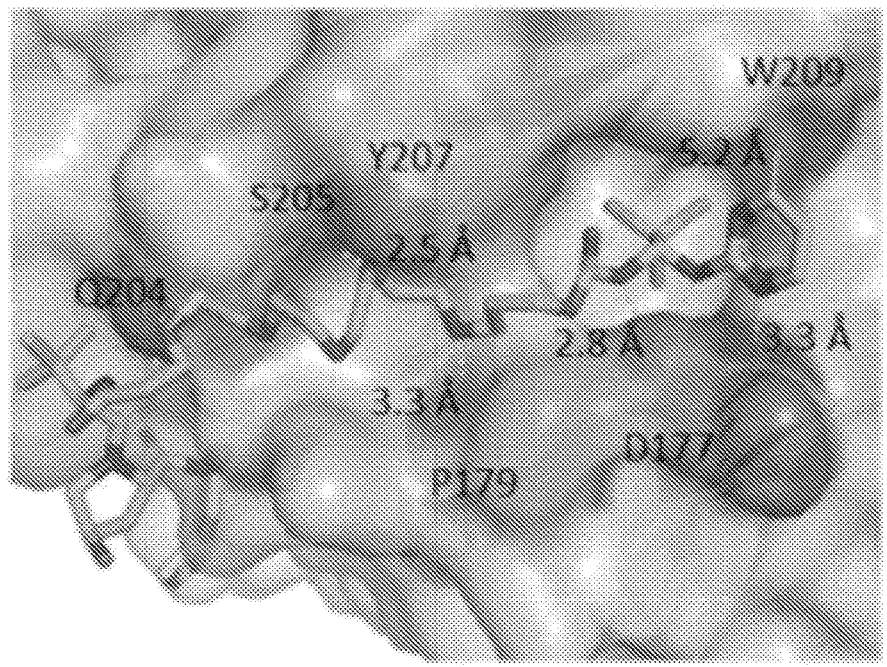
FIG. 5C shows a non-limiting example of the interaction between CP5V and Cdc20 according to the model shown in FIG. 5A. H-bonding and 7L-7L interactions between ligand and proteins have been displayed with yellow dash lines.
Figure 5D:
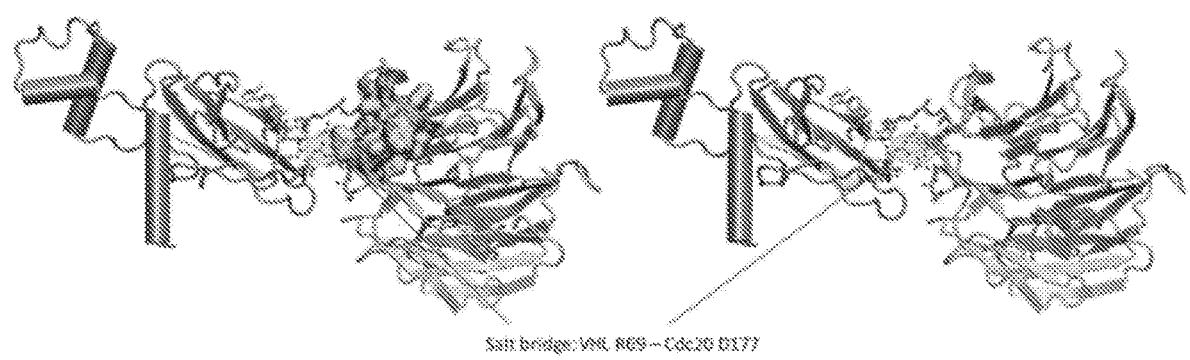
FIG. 5D shows a non-limiting example of the salt bridge between VHL R69 and C20 D177, which appears to be important to this conformation of complex. (Sackton, Dimova et al. 2014; Ve, Vajjhala et al. 2017).

To address the mechanism underlying CP5V-mediated inhibition of cancer cells growth, a molecular modeling analysis was performed to explore how CP5V forms a stable ternary complex with Cdc20 and VHL (FIG. 5A). To elucidate the 3D structure of the ternary complex, CP5V was docked to both VHL and Cdc20 through previously reported binding sites using the structures and docking poses in PDB 5T35 (Ve, Vajjhala et al. 2017) and PDB 4N14 (Sackton, Dimova et al. 2014), respectively (FIGS. 5B & 5C). The results demonstrated, at one end, the benzyl ring of CP5V forms 7L-7L interactions with Tyr98 of VHL, and the neighboring hydroxyproline (Hyp) group forms several hydrogen bonds with Tyr98, His110, Ser111 and His115 (FIG. 5B). At the opposite end with Apcin-A, the hydrophobic trichloromethyl group inserts into a hydrophobic pocket and occupies the D-box-binding pocket on the side face of the WD40-domain (Sackton, Dimova et al. 2014) (FIG. 5C). The Apcin-A portion forms a π-π interaction with Trp209 of Cdc20, and forms hydrogen bonds with Asp177 and Pro179 (FIG. 5C). The ternary complex was observed to be stably maintained in five out of six molecular dynamics (MD) simulations, including one extended to 200 ns (FIGS. 13A-13I). The PEG linker also forms several hydrogen bonds with residues of both VHL and Cdc20 (FIGS. 5B & 5C), which further strengthens the attachment to each of the proteins. Also noted were the formation of interprotein salt bridges, VHL-Cdc20 Arg69-Glu180, Arg64-Glu180 and Arg69-Asp177 (FIG. 13H) which assisted in the association of the two proteins.

Example 23. Mouse 4T1 Xenograft Model Studies

The impact of CP5V in mouse 4T1 xenograft model was examined. In this model, 5×105 cells 4T1 cells in PBS were injected into the Balb/C mice mammary fat pad. When tumors were palpable, tumor growth was measured for 3 weeks and calculated as 0.52xLXWxW (L=Length, W=Width). Ten days after 4T1 injection, 100 mg/kg CP5V (dissolved in 30% N, N-Dimethylacetamide+Saline) or placebo (30% N, N-Dimethylacetamide+saline) were intraperitoneally administrated twice per week to the mice. The mice were sacrificed at the end of treatment, and the xenograft tumor was collected, formalin fixed, paraffin embedded, sectioned. Immunohistochemistry (IHC) was conducted with xenograft tumor and liver tissues to detect Cdc20, Ki67, Activate and Caspase-3.

Figure 6A:
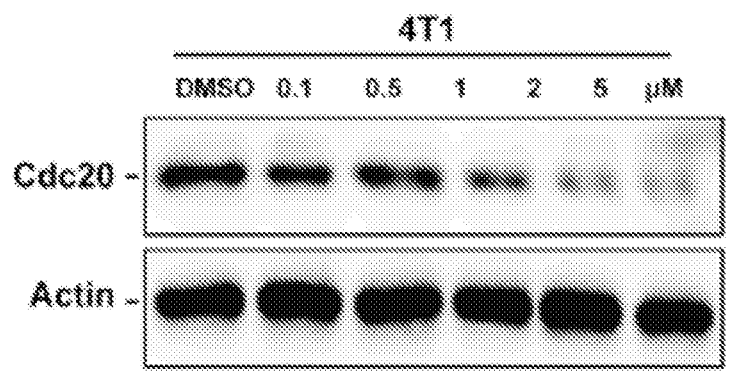
FIG. 6A shows a non-limiting example of CP5V causing degradation of Cdc20 in 4T1 cells lines in vitro.
Figure 6B:
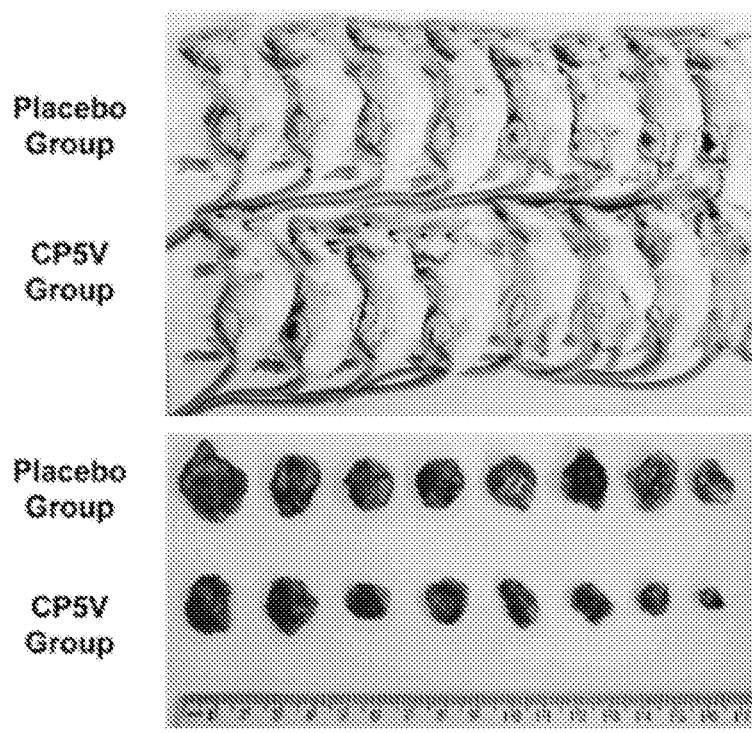
FIG. 6B shows an image of 4T1 xenograft tumors harvested after 21 days from a mouse 4T1 xenograft model.
Figure 6C:
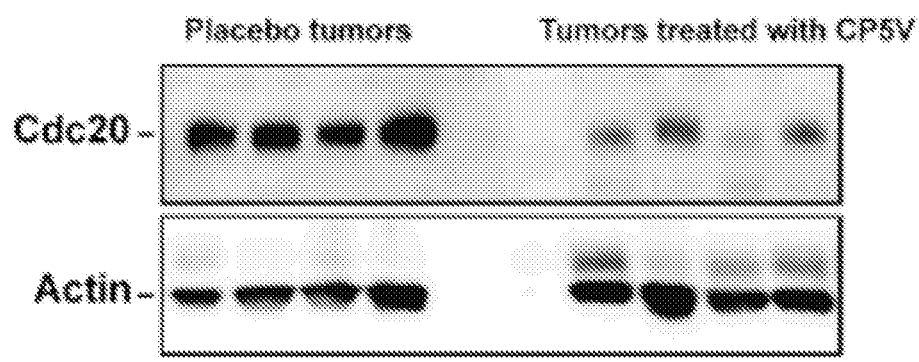
FIG. 6C shows Western blotting assay results for the expression of Cdc20 in 4T1 xenograft tumor from the mice in FIG. 6B.
Figure 6D:
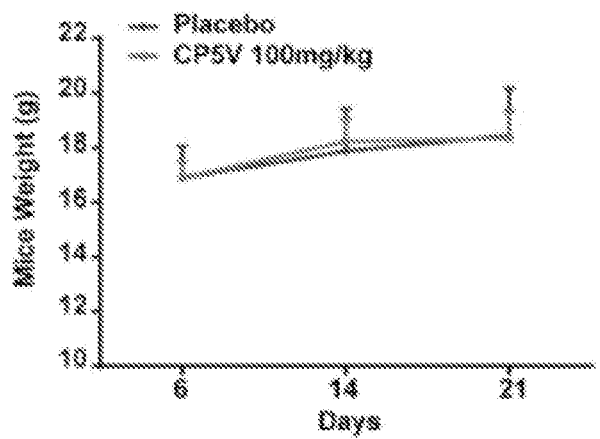
FIG. 6D shows the mouse body weight curve of mice in FIG. 6B.
Figure 6E:
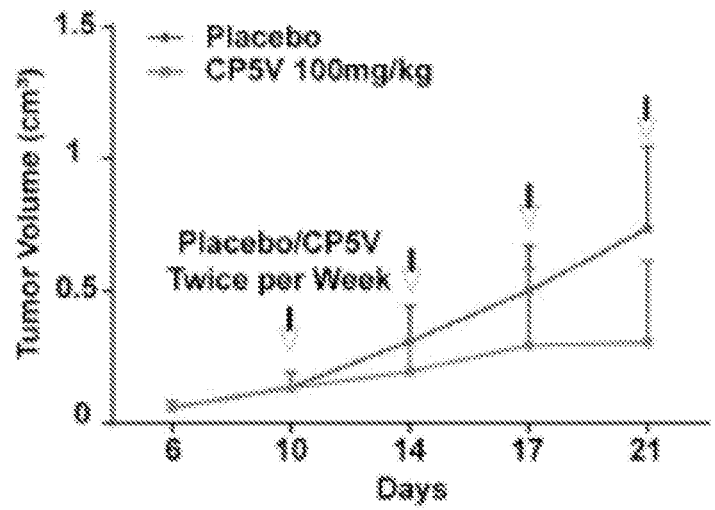
FIG. 6E shows the tumor growth curve of tumors from mice in FIG. 6B. Tumor volume was measured twice per week. The asterisk represents the significant difference (p<0.05) between group Placebo and group CP5V.
Figure 6F:
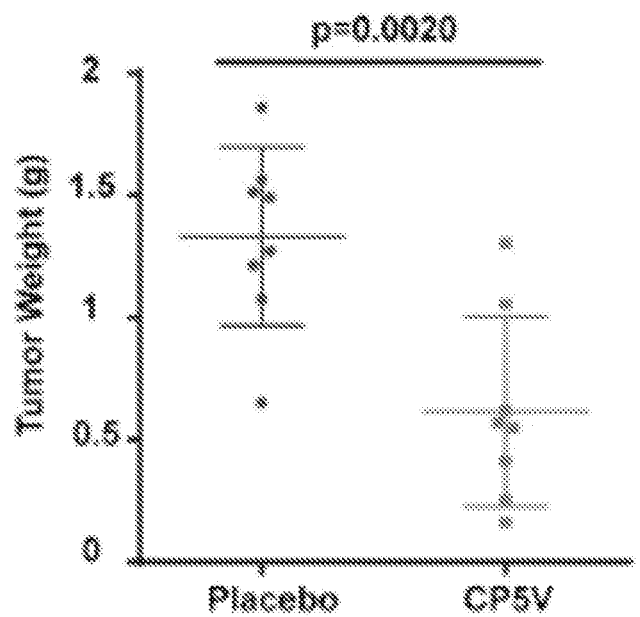
FIG. 6F shows the tumor weight curve of tumors from mice in FIG. 6B.
Figure 6G:
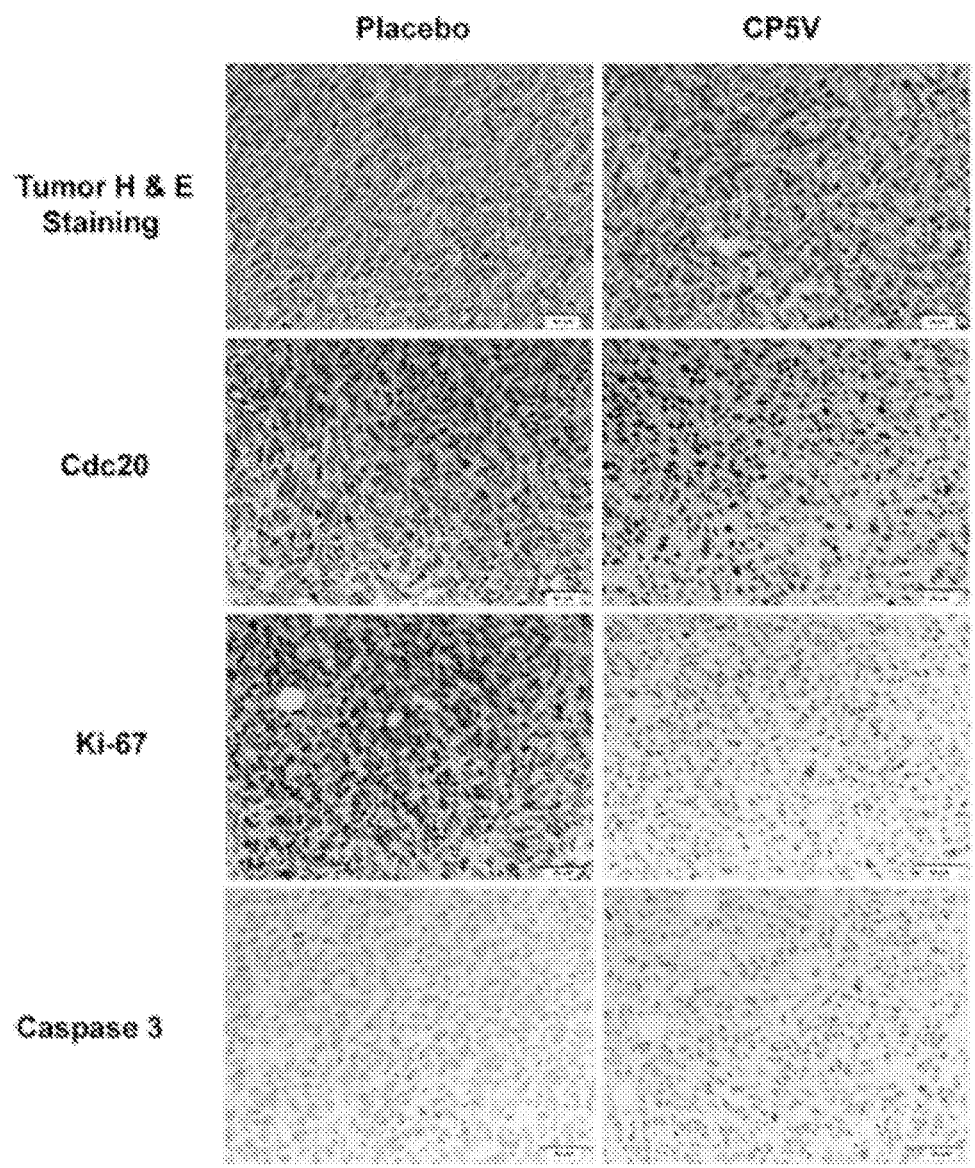
FIG. 6G shows the immunohistochemistry staining of H & E, Cdc20, Ki67, and activated caspase 3 in 4T1 xenograft tumors from mice in FIG. 6B.
Figure 6H:
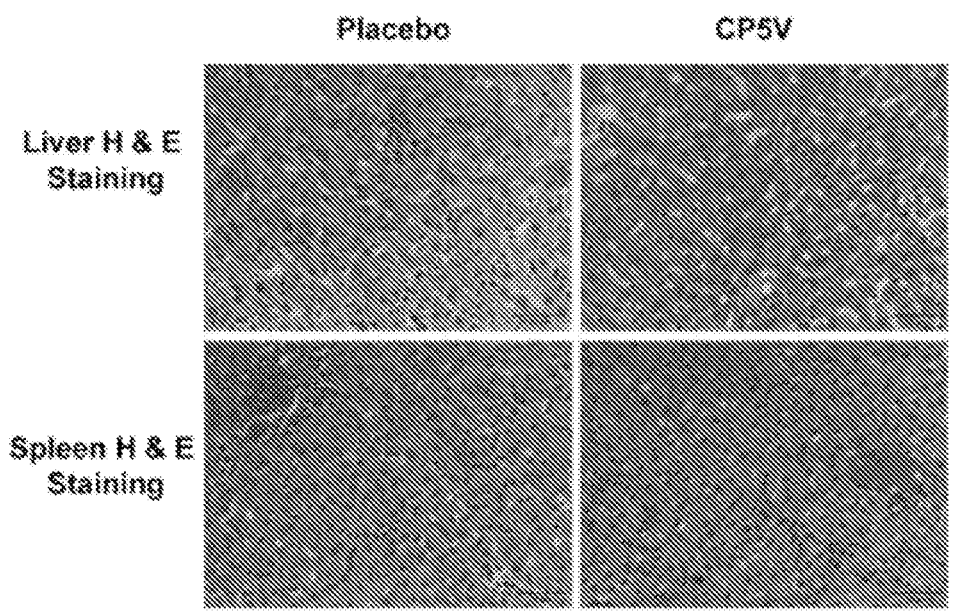
FIG. 6H shows the H & E staining of tumor and liver of mice from both Placebo and CP5V group of the mice in FIG. 6B.
Figure 6I:
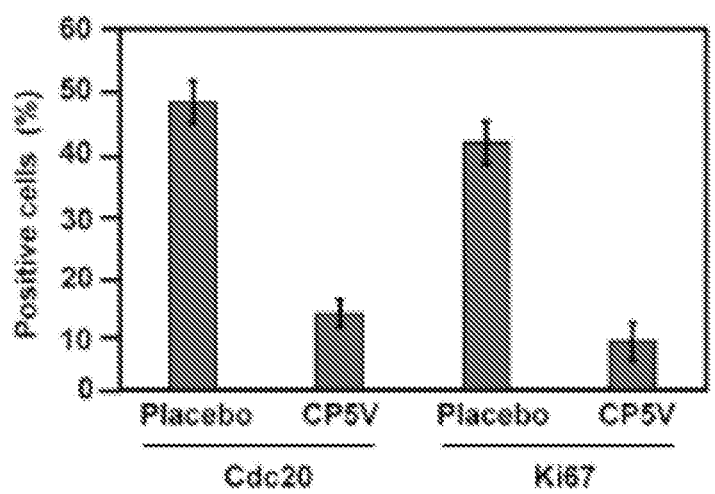
FIG. 6I shows the quantification of Ki67 and activated caspase 3 positive cells in 4T1 xenograft tumors from mice in FIG. 6B.
Figure 7:
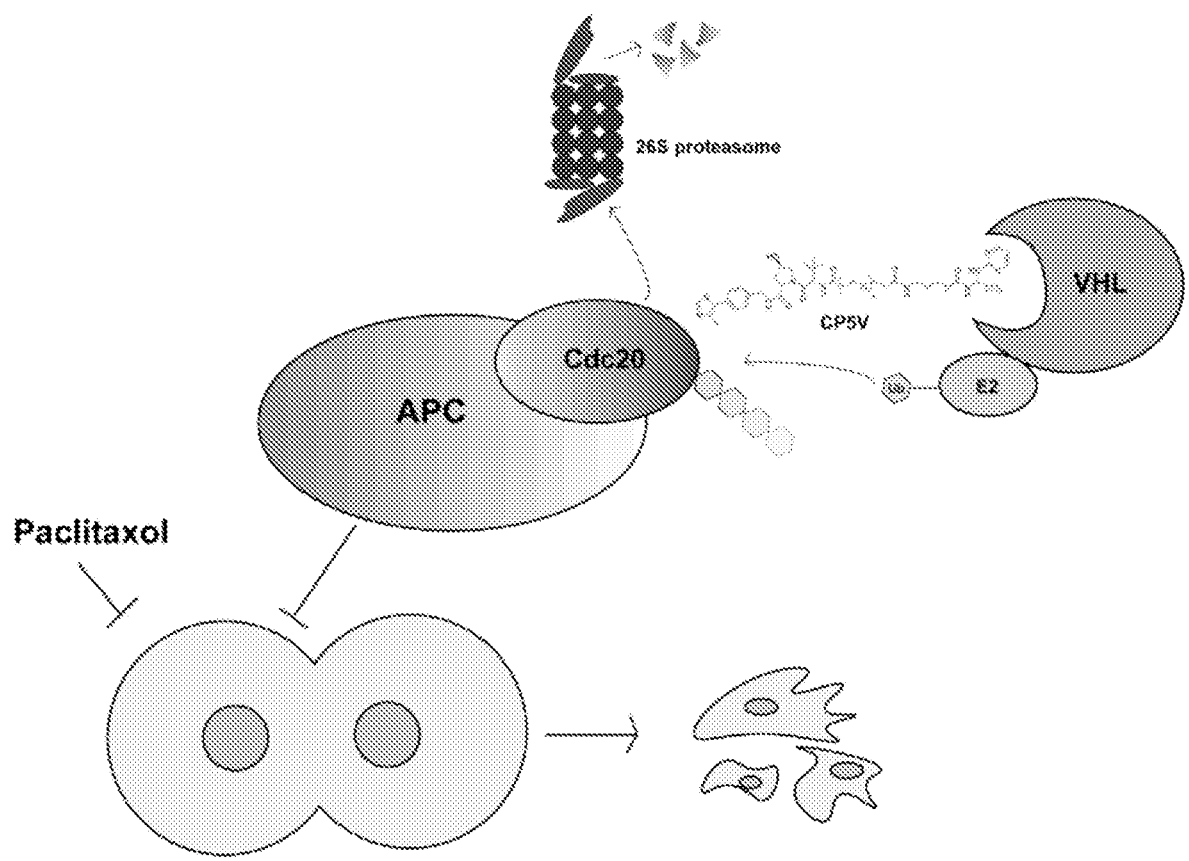
FIG. 7 shows a hypothetical working model of CP5V causing specific degradation of Cdc20 by the ubiquitin-proteasome system (UPS), which induces mitotic arrest of cancer cells and restores the Taxol-induced cytotoxic response for the Taxol-resistant cells.

As shown in FIG. 6A, CP5V induced dose-dependent Cdc20 degradation in 4T1 cells. More specifically, the results demonstrated that the administration of CP5V reduced approximately 70% of the size and weight of the 4T1 xenograft tumor compared to the placebo, while no significant effect on mice body weight and liver toxicity was observed (FIGS. 6B-6F). The result of immunohistochemistry (IHC) analysis showed that CP5V decreased Cdc20 expression in the 4T1 xenograft tumor (FIGS. 6G & 6I). The expression levels of Cdc20, Ki67 and caspase-3 in the isolated grafted tumors were measured using IHC analysis, and the results confirmed CP5V reduced tumor growth by decreasing the Ki67 index in the tumor (FIGS. 6I-6J). The expression of caspase-3 did not change dramatically.

REFERENCES

Agarwal, S. and D. Varma (2017). "Targeting mitotic pathways for endocrine-related cancer therapeutics." *Endocr Relat Cancer* 24(9): T65-T82.

Brito, D. A. and C. L. Rieder (2006). "Mitotic checkpoint slippage in humans occurs via cyclin B destruction in the presence of an active checkpoint." *Curr Biol* 16(12): 1194-1200.

Buckley, D. L., I. Van Molle, et al. (2012). "Targeting the von Hippel-Lindau E3 ubiquitin ligase using small molecules to disrupt the VHL/HIF-1alpha interaction." *J Am Chem Soc* 134(10): 4465-4468.

Chamberlain, P. P., A. Lopez-Girona, et al. (2014). "Structure of the human Cereblon-DDB1-lenalidomide complex reveals basis for responsiveness to thalidomide analogs." *Nat Struct Mol Biol* 21(9): 803-809.

Ding, Z. Y., H. R. Wu, et al. (2014). "Expression characteristics of $CDCl_20$ in gastric cancer and its correlation with poor prognosis." *Int J Clin Exp Pathol* 7(2): 722-727.

Franken, N. A., H. M. Rodermond, et al. (2006). "Clonogenic assay of cells in vitro." *Nat Protoc* 1(5): 2315-2319.

Galdeano, C., M. S. Gadd, et al. (2014). "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities." *J Med Chem* 57(20): 8657-8663.

Gascoigne, K. E. and S. S. Taylor (2008). "Cancer cells display profound intra- and interline variation following prolonged exposure to antimitotic drugs." *Cancer Cell* 14(2): 111-122.

Harley, M. E., L. A. Allan, et al. (2010). "Phosphorylation of Mcl-1 by CDK1-cyclin B1 initiates its Cdc20-dependent destruction during mitotic arrest." *EMBO J* 29(14): 2407-2420.

Huang, H. C., J. Shi, et al. (2009). "Evidence that mitotic exit is a better cancer therapeutic target than spindle assembly." *Cancer Cell* 16(4): 347-358.

Jackson, J. R., D. R. Patrick, et al. (2007). "Targeted anti-mitotic therapies: can we improve on tubulin agents?" *Nat Rev Cancer* 7(2): 107-117.

Jordan, M. A. and L. Wilson (2004). "Microtubules as a target for anticancer drugs." *Nat Rev Cancer* 4(4): 253-265.

Kapanidou, M., N. L. Curtis, et al. (2017). "Cdc20: At the Crossroads between Chromosome Segregation and Mitotic Exit." *Trends Biochem Sci* 42(3): 193-205.

Karra, H., H. Repo, et al. (2014). "Cdc20 and securin overexpression predict short-term breast cancer survival." *Br J Cancer* 110(12): 2905-2913.

Kato, T., Y. Daigo, et al. (2012). "Overexpression of $CDCl_20$ predicts poor prognosis in primary non-small cell lung cancer patients." *J Surg Oncol* 106(4): 423-430.

Lai, A. C. and C. M. Crews (2017). "Induced protein degradation: an emerging drug discovery paradigm." *Nat Rev Drug Discov* 16(2): 101-114.

Manchado, E., M. Guillamot, et al. (2012). "Killing cells by targeting mitosis." *Cell Death Differ* 19(3): 369-377.

Neklesa, T. K., J. D. Winkler, et al. (2017). "Targeted protein degradation by PROTACs." *Pharmacol Ther* 174: 138-144.

Raina, K., J. Lu, et al. (2016). "PROTAC-induced BET protein degradation as a therapy for castration-resistant prostate cancer." *Proc Natl Acad Sci USA* 113(26): 7124-7129.

Sackton, K. L., N. Dimova, et al. (2014). "Synergistic blockade of mitotic exit by two chemical inhibitors of the APC/C." *Nature* 514(7524): 646-649.

Salami, J., S. Alabi, et al. (2018). "Androgen receptor degradation by the proteolysis-targeting chimera ARCC-4 outperforms enzalutamide in cellular models of prostate cancer drug resistance." *Commun Biol* 1: 100.

Schutte, U., S. Bisht, et al. (2014). "Hippo signaling mediates proliferation, invasiveness, and metastatic potential of clear cell renal cell carcinoma." *Transl Oncol* 7(2): 309-321.

Shi, J. and T. J. Mitchison (2017). "Cell death response to anti-mitotic drug treatment in cell culture, mouse tumor model and the clinic." *Endocr Relat Cancer* 24(9): T83-T96.

Shi, J., J. D. Orth, et al. (2008). "Cell type variation in responses to antimitotic drugs that target microtubules and kinesin-5." *Cancer Res* 68(9): 3269-3276.

Sun, B., W. Fiskus, et al. (2018). "BET protein proteolysis targeting chimera (PROTAC) exerts potent lethal activity against mantle cell lymphoma cells." *Leukemia* 32(2): 343-352.

Ve, T., P. R. Vajjhala, et al. (2017). "Structural basis of TIR-domain-assembly formation in MAL- and MyD88-dependent TLR4 signaling." *Nat Struct Mol Biol* 24(9): 743-751.

Wang, L., J. Zhang, et al. (2015). "Targeting Cdc20 as a novel cancer therapeutic strategy." *Pharmacol Ther* 151: 141-151.

Wang, P. and J. Zhou (2018). "Proteolysis Targeting Chimera (PROTAC): A Paradigm-Shifting Approach in Small Molecule Drug Discovery." *Curr Top Med Chem* 18(16): 1354-1356.

Wu, W. J., K. S. Hu, et al. (2013). "$CDCl_2 0$ overexpression predicts a poor prognosis for patients with colorectal cancer." *J Transl Med* 11: 142.

Yang, C. H. and S. B. Horwitz (2017). "Taxol((R)): The First Microtubule Stabilizing Agent." *Int J Mol Sci* 18(8).

Zeng, X. and R. W. King (2012). "An APC/C inhibitor stabilizes cyclin B1 by prematurely terminating ubiquitination." *Nat Chem Biol* 8(4): 383-392.

Zeng, X., F. Sigoillot, et al. (2010). "Pharmacologic inhibition of the anaphase-promoting complex induces a spindle checkpoint-dependent mitotic arrest in the absence of spindle damage." *Cancer Cell* 18(4): 382-395.

Zhou, Z., M. He, et al. (2016). "Insights into APC/C: from cellular function to diseases and therapeutics." *Cell Div* 11: 9.

Zur, A. and M. Brandeis (2001). "Securin degradation is mediated by fzy and fzr, and is required for complete chromatid separation but not for cytokinesis." *EMBO J* 20(4): 792-801.

While certain embodiments have been illustrated and described, it should be understood that changes and modifications can be made therein in accordance with ordinary skill in the art without departing from the invention in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed invention. Additionally, the phrase "consisting essentially of" will be understood to include those elements specifically recited and those additional elements that do not materially affect the basic and novel characteristics of the claimed invention. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting. Any recited method can be carried out in the order of events recited or in any other order which is logically possible.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Para. A. A compound of Formula I, or a pharmaceutically acceptable salt or ester thereof:

$$X-L-Y \qquad \text{(Formula I)}$$

wherein:

X is a cell-division cycle protein 20 (Cdc20) binding moiety;

Y is an E3 ubiquitin ligase binding moiety; and

L is a linker covalently attached to X and Y or a bond between X and Y.

Para. B. The compound of Para. A, wherein X comprises a moiety selected from the group consisting of Apcin and Apcin-A, or a derivative thereof.

Para. C. The compound of Para. A, wherein X comprises:

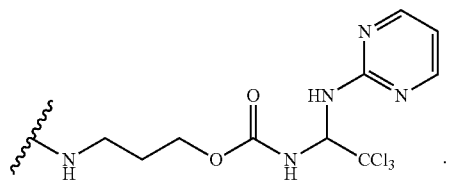

Para. D. The compound of any one of Paras. A-C, wherein Y is a moiety that binds an E3 ubiquitin ligase selected from the group consisting of Von Hippel-Lindau (VHL) E3 ubiquitin ligase, cereblon (CRBN), IAP, and MDM2.

Para. E. The compound of any one of Paras. A-D, wherein Y comprises a moiety selected from:

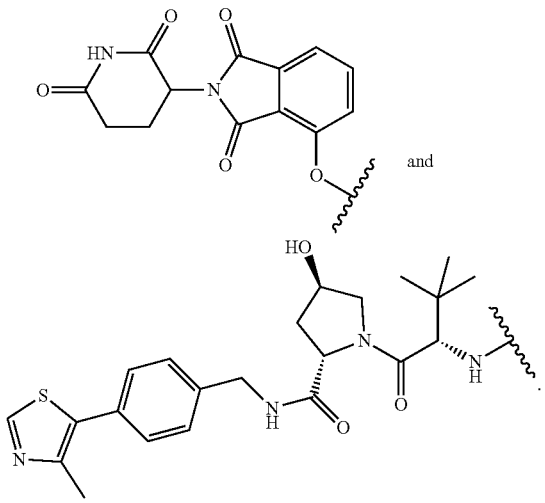

Para. F. The compound of any one of Paras. A-E, wherein L comprises:

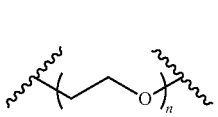

wherein n is an integer greater than or equal to 2.

Para. G. The compound of any one of Paras. A-F, wherein L is selected from the group consisting of:

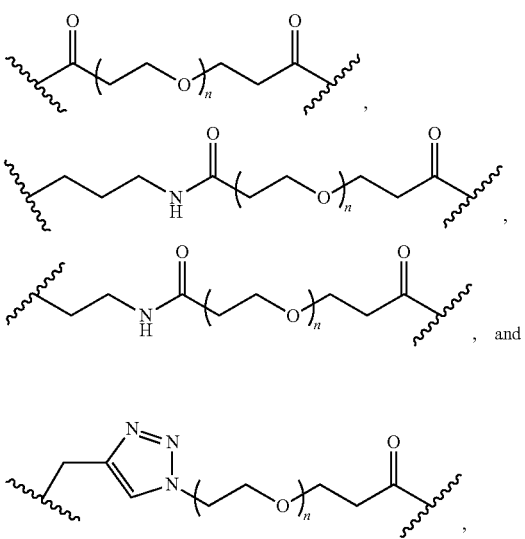

wherein n is an integer greater than or equal to 2.

Para. H. The compound of Para. A, selected from the group consisting of

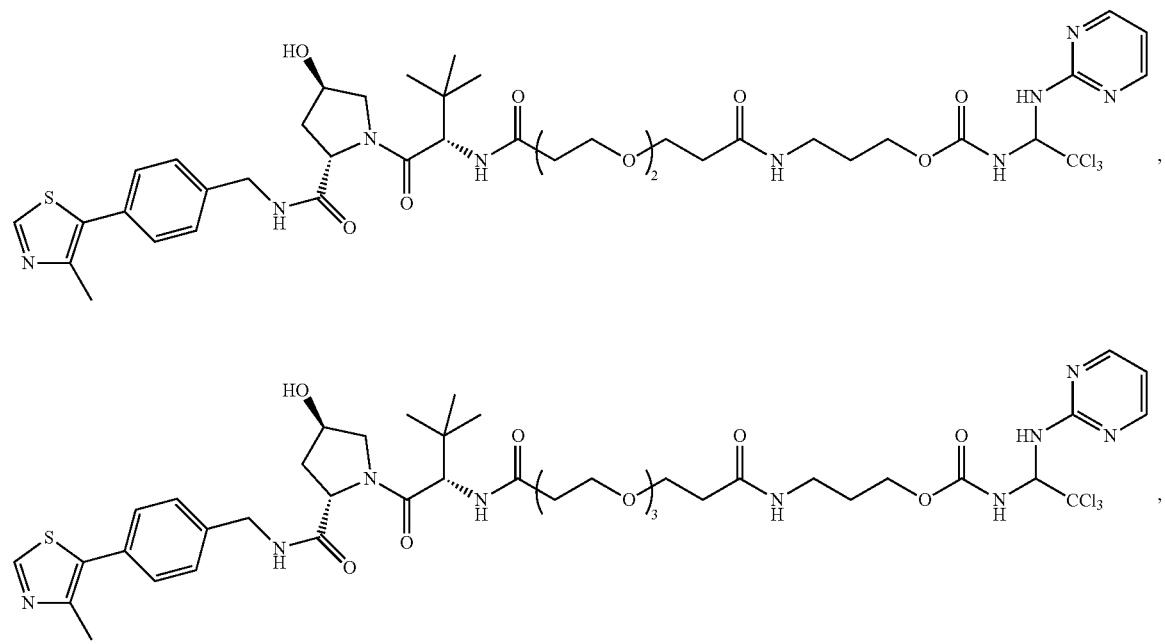

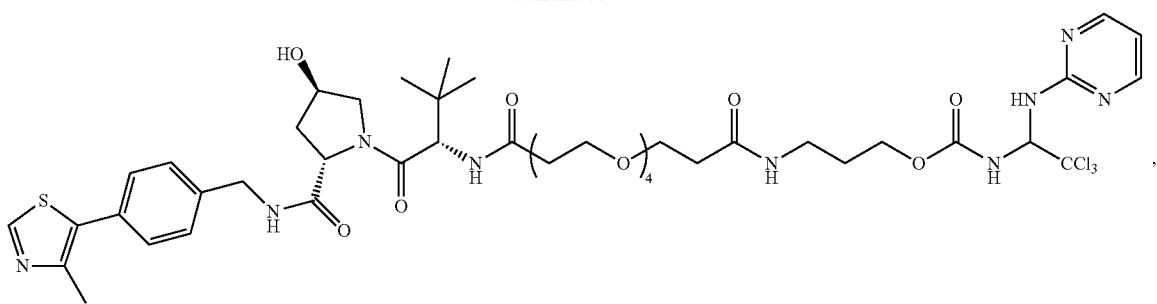,
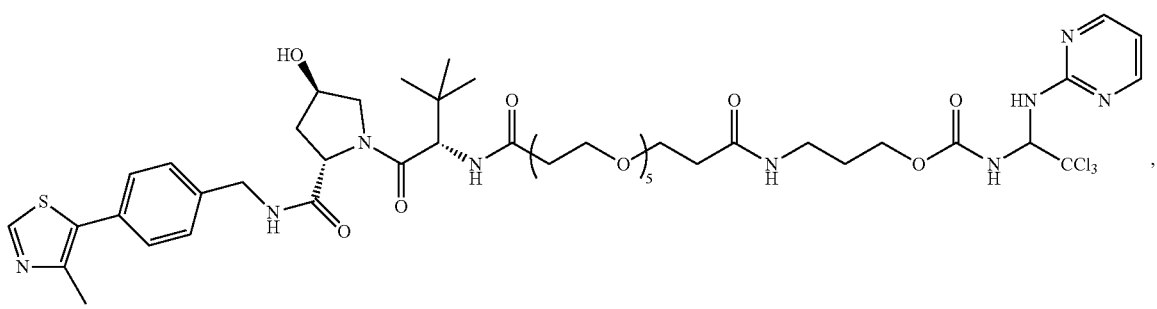,
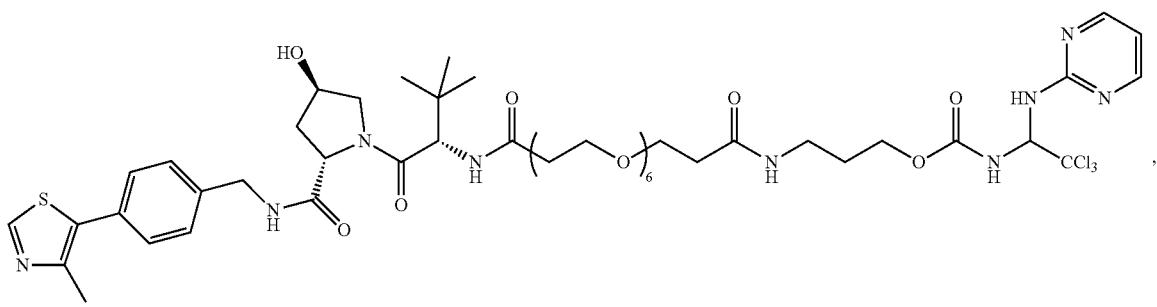,
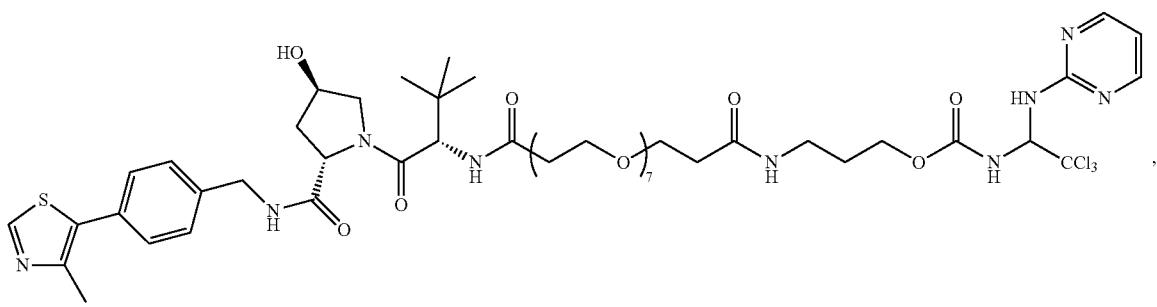,
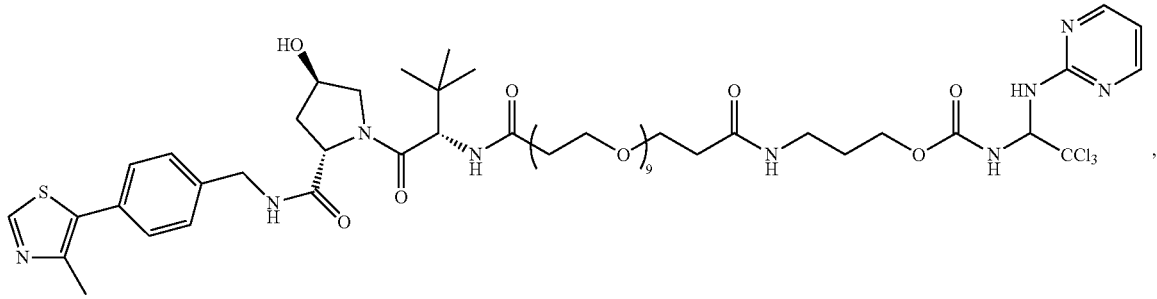,

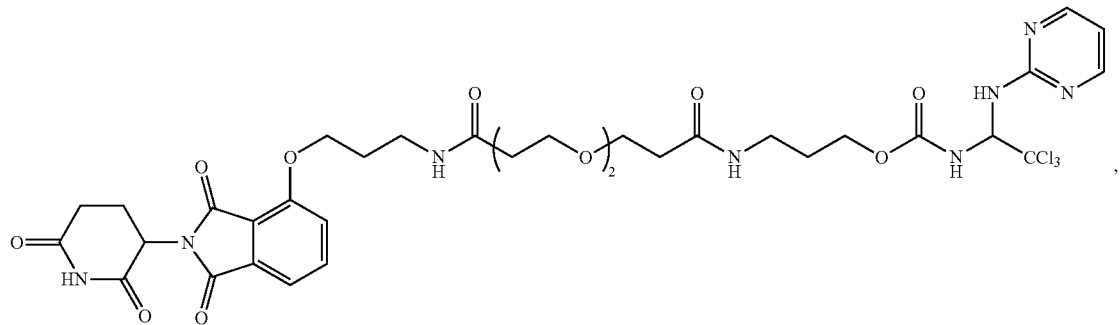
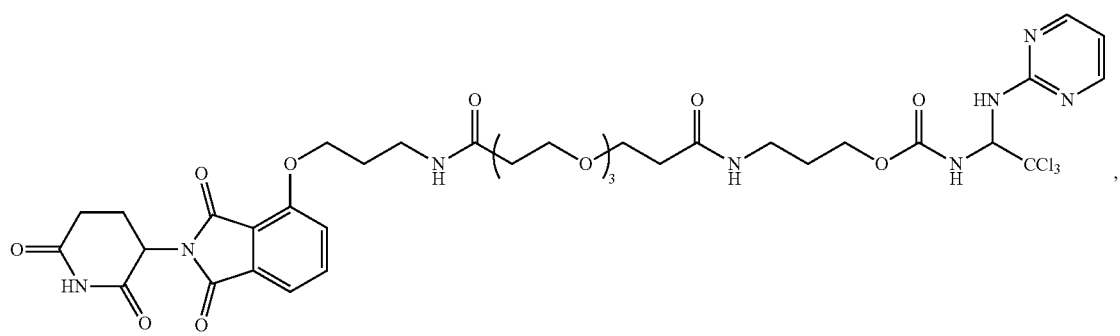
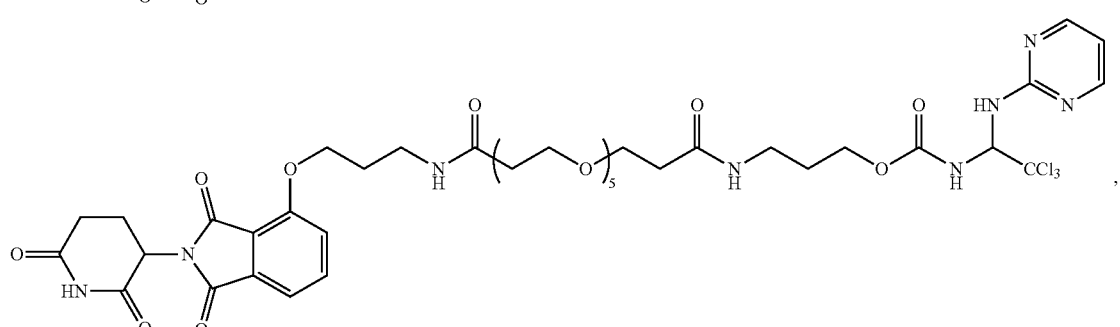
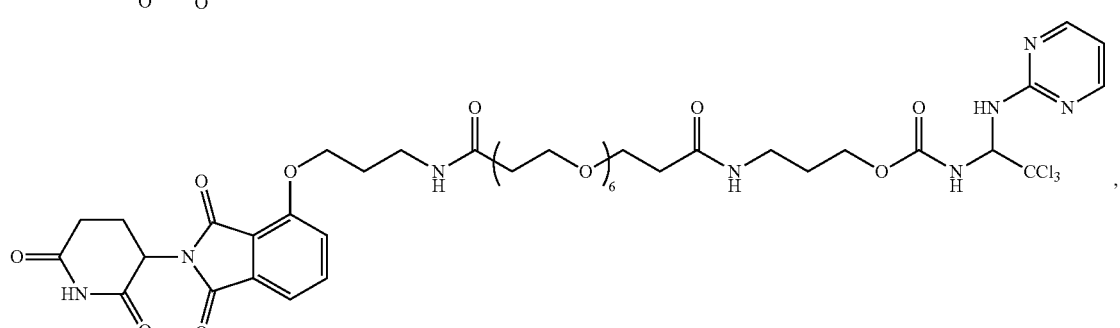
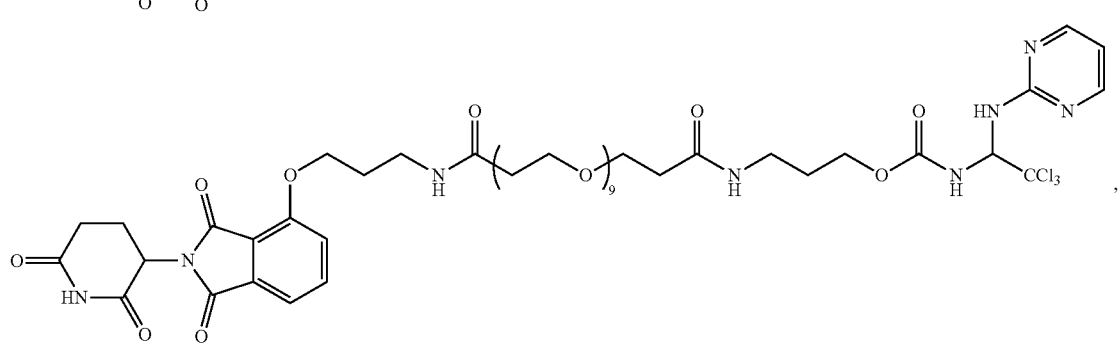

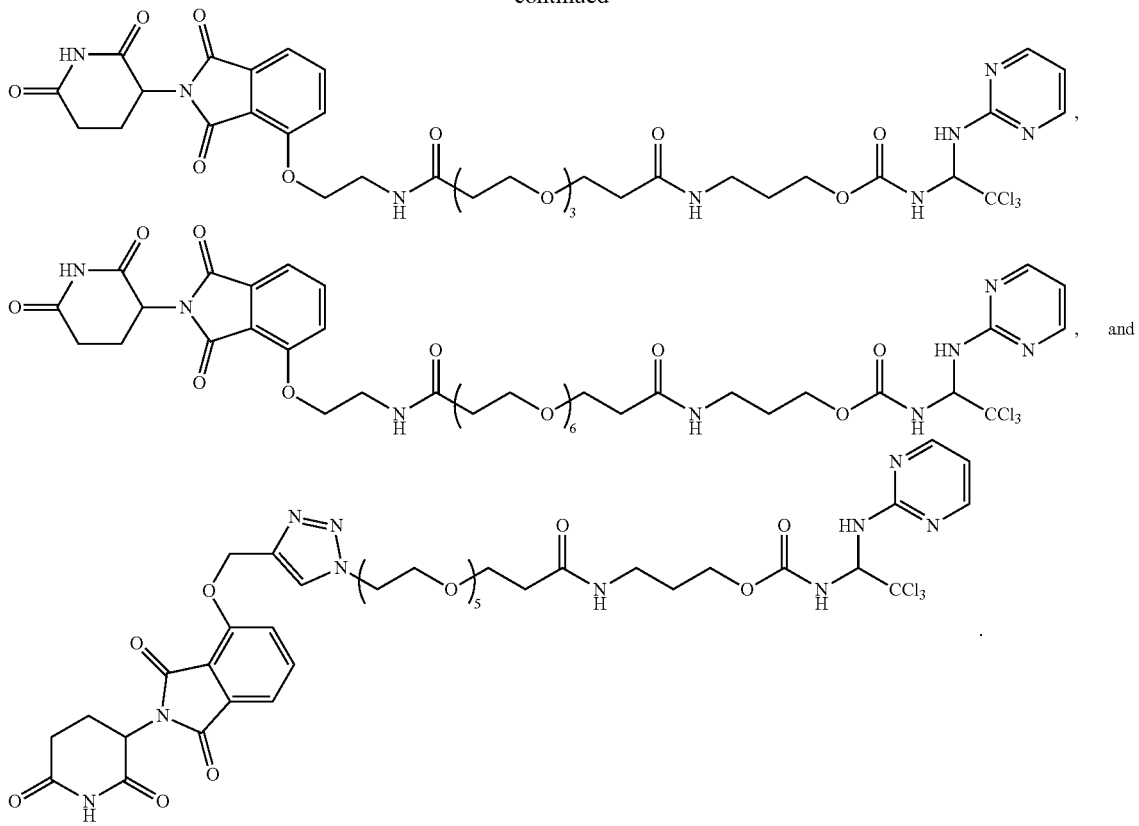

Para. I. A composition comprising an effective amount of the compound of any one of Paras. A-H and at least one pharmaceutically acceptable carrier.

Para. J. The composition of Para. I further comprising at least one additional active agent.

Para. K. The composition of Para. J, wherein the at least one additional active agent is an anti-cancer agent.

Para. L. A method of treating cancer in a subject in need thereof, the method comprising administering to the subject a therapeutically effective amount of the compound of any one of Paras. A-H or the composition of Para. I.

Para. M. The method of Para. L, wherein the cancer is breast cancer,

Para. N. A method of inducing Cdc20 degradation in a cell, the method comprising contacting the cell with an effective amount of the compound of any one of Paras. A-H or the composition of Para. I.

Para. O. A method of blocking mitotic progression in a subject, the method comprising administering to the subject a therapeutically effective amount of the compound of any one of Paras. A-H or the composition of Para. I.

Para. P. A method of inhibiting tumor proliferation in a subject, the method comprising administering to the subject a therapeutically effective amount of the compound of any one of Paras. A-H or the composition of Para. I.

Para. Q. A method of re-sensitizing a subject to cancer treatment with tamoxifen, the method comprising administering to the subject a therapeutically effective amount of the compound of any one of Paras. A-H or the composition of Para. I, wherein the subject is resistant to treatment with tamoxifen prior to administration of the compound of any one of Paras. A-H or the composition of Para. I.

Other embodiments are set forth in the following claims.

What is claimed is:

1. A compound of Formula I, or a pharmaceutically acceptable salt or ester thereof:

X-L-Y  (Formula I)

wherein:
X is a cell-division cycle protein 20 (Cdc20) binding moiety;
Y is an E3 ubiquitin ligase binding moiety; and
L is a linker covalently attached to X and Y or a bond between X and Y.

2. The compound of claim 1, wherein X comprises a moiety selected from the group consisting of Apcin and Apcin-A, or a derivative thereof.

3. The compound of claim 1, wherein X comprises:

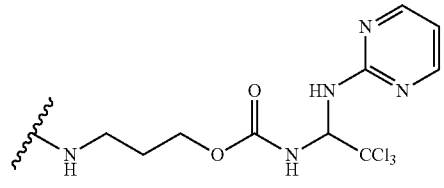

4. The compound of claim 1, wherein Y is a moiety that binds an E3 ubiquitin ligase selected from the group consisting of Von Hippel-Lindau (VHL) E3 ubiquitin ligase, cereblon (CRBN), IAP, and MDM2.

5. The compound of claim 1, wherein Y comprises a moiety selected from:

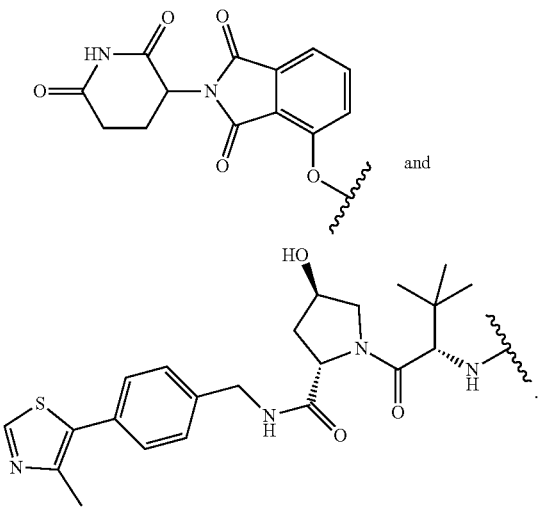
6. The compound of claim 1, wherein L comprises:
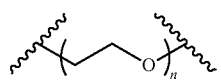
wherein n is an integer greater than or equal to 2.
7. The compound of claim 1, wherein L is selected from the group consisting of:
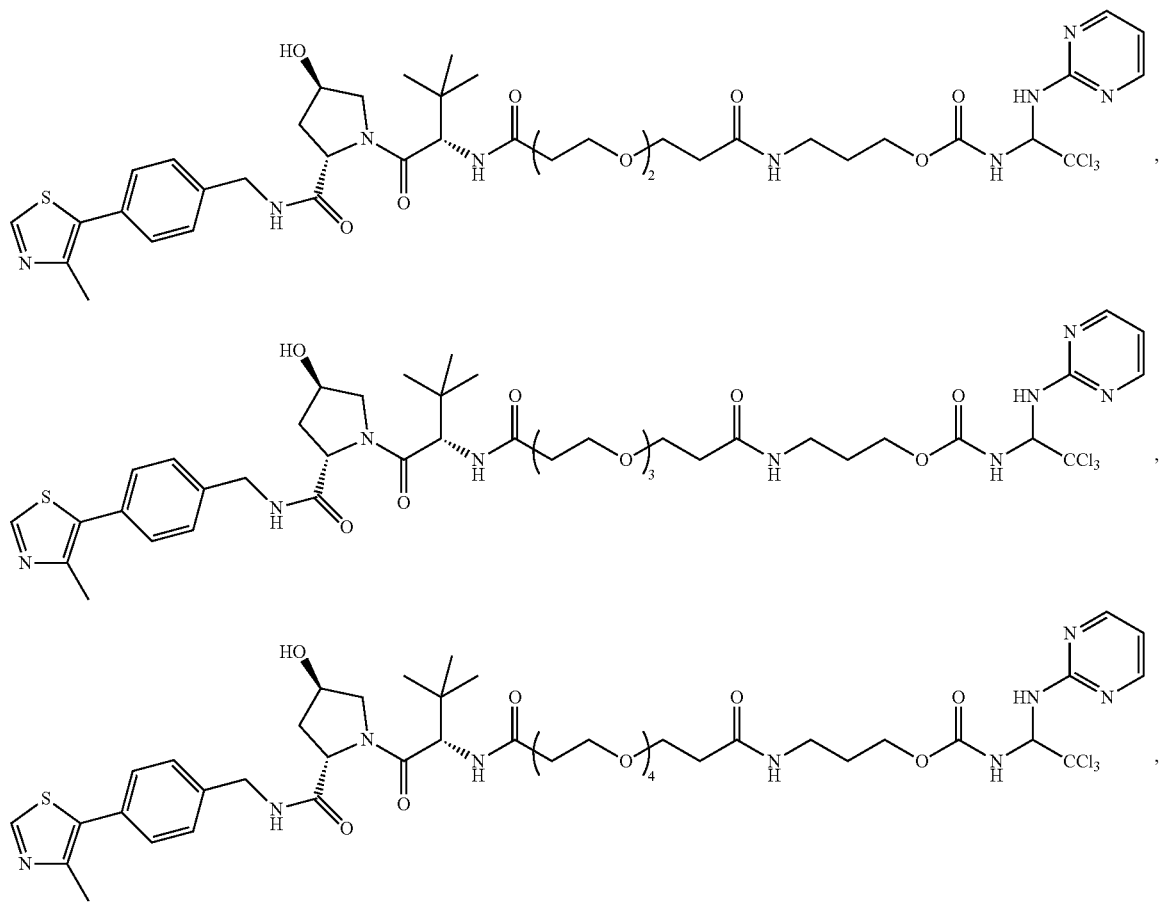
wherein n is an integer greater than or equal to 2.
8. The compound of claim 1, selected from the group consisting of

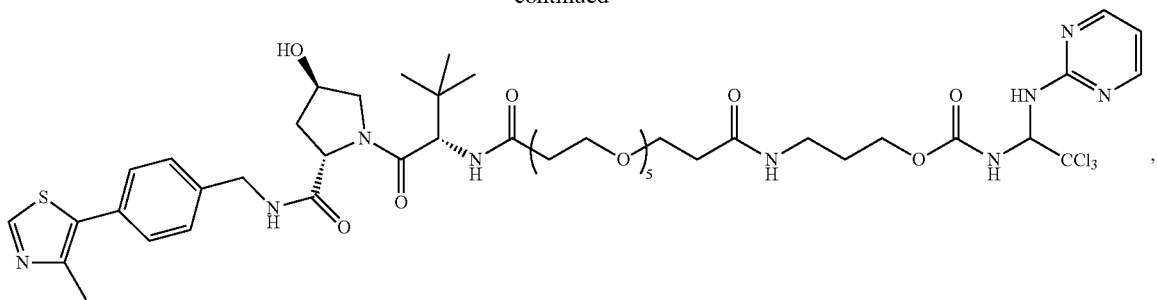
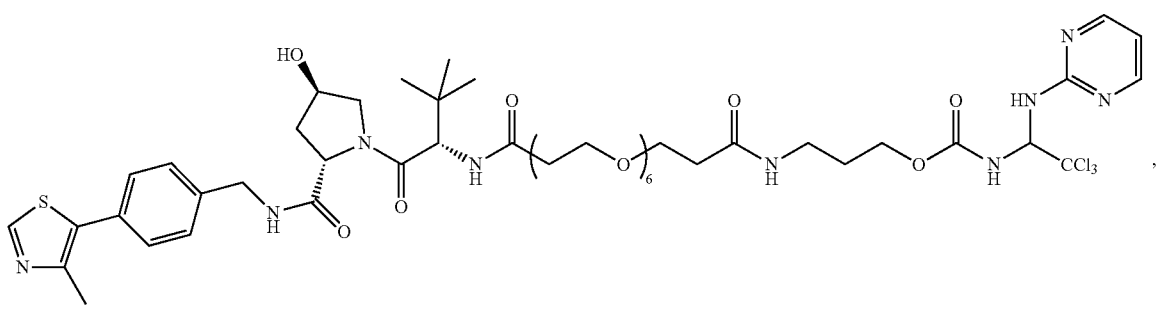
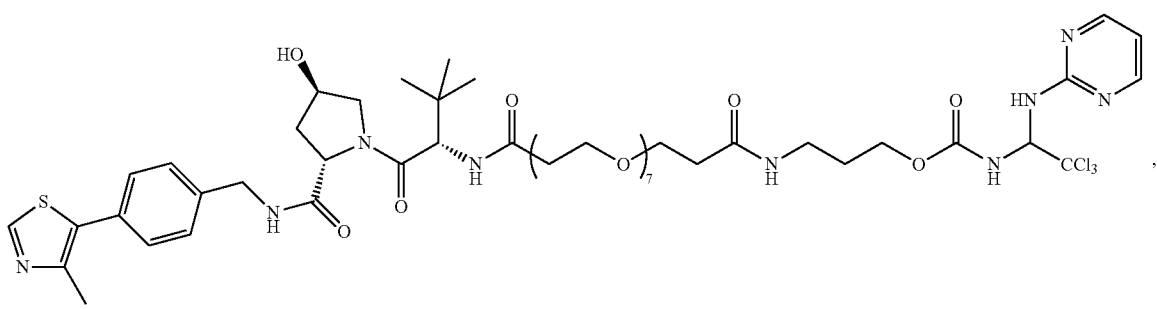
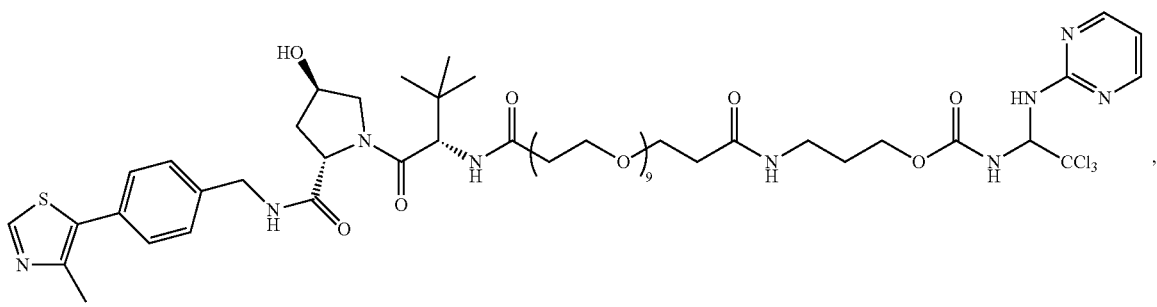
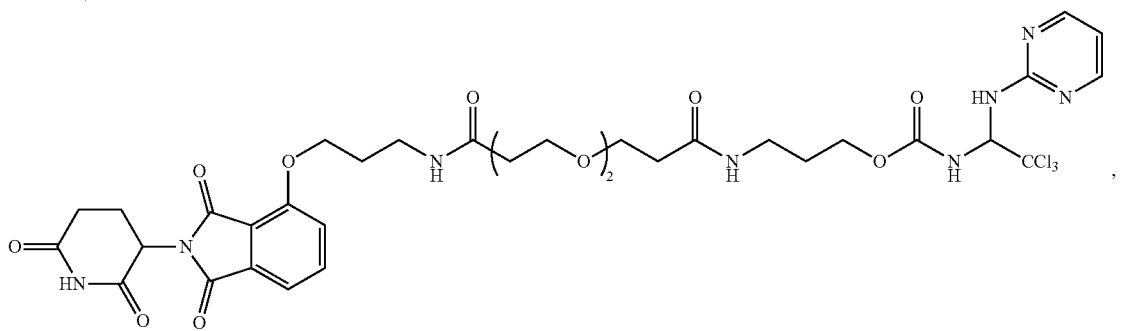

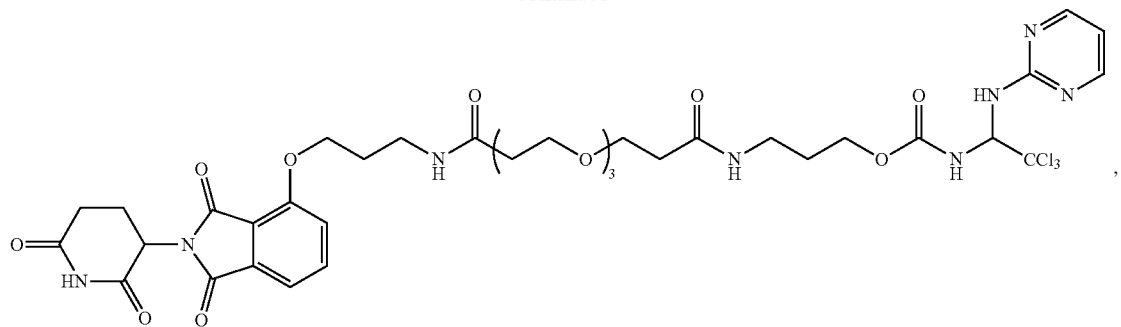
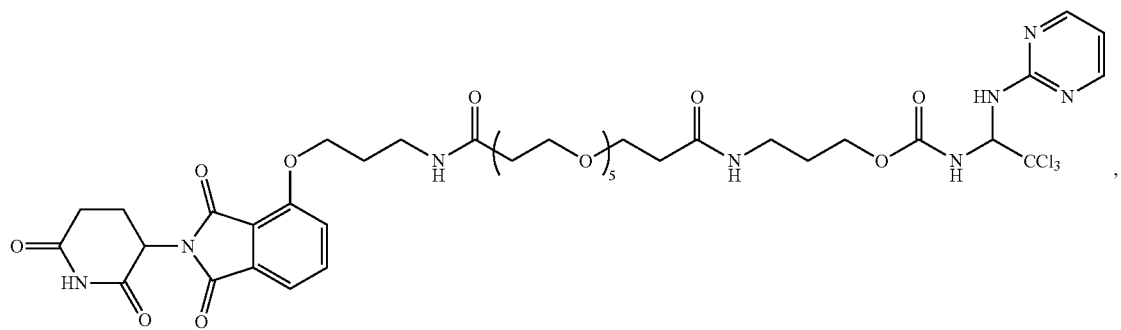
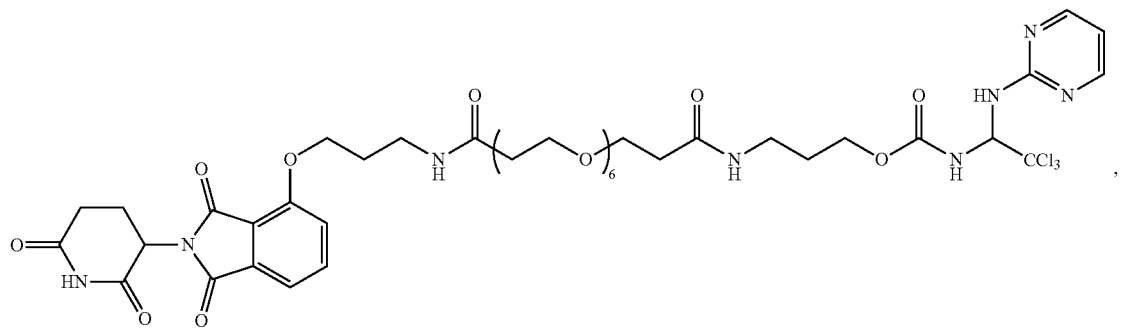
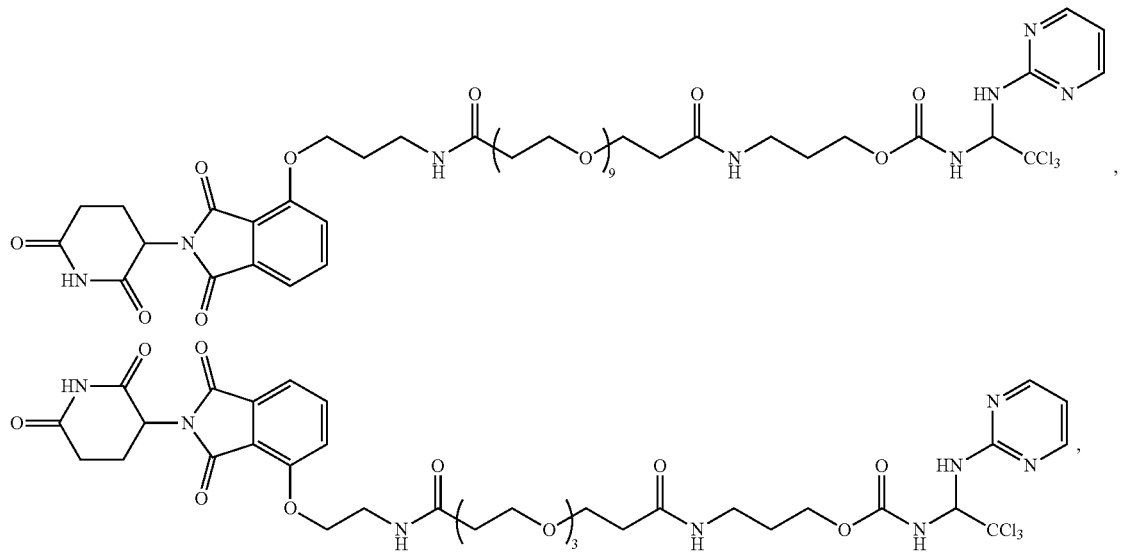

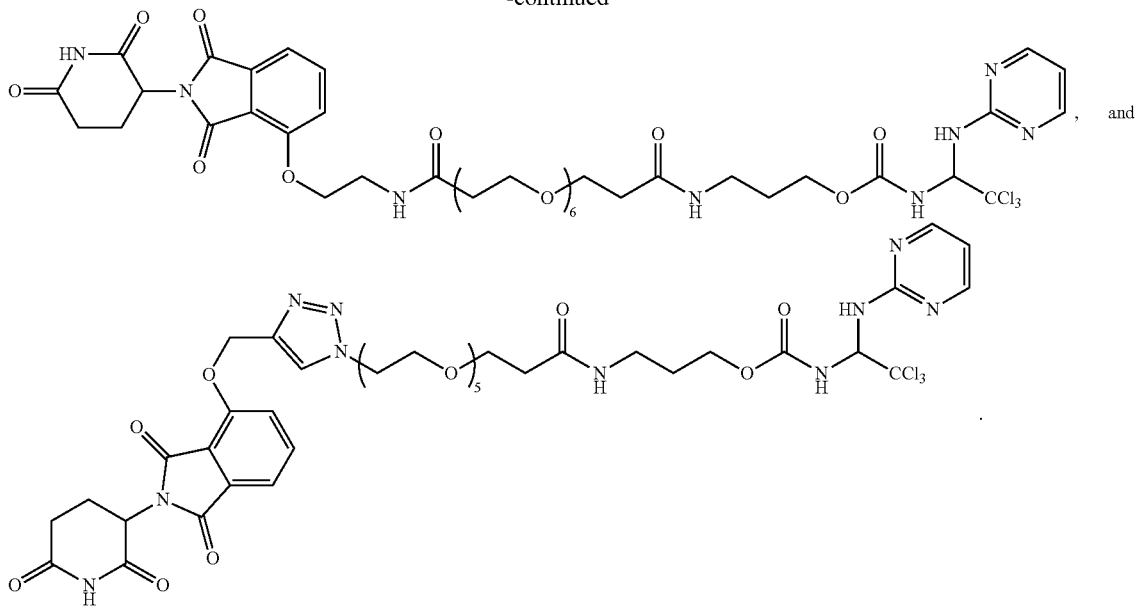

9. A composition comprising an effective amount of the compound of claim 1 and at least one pharmaceutically acceptable carrier.

10. The composition of claim 9 further comprising at least one additional active agent.

11. The composition of claim 10, wherein the at least one additional active agent is an anti-cancer agent.

12. A method of treating cancer in a subject in need thereof, the method comprising administering to the subject a therapeutically effective amount of the compound of claim 1.

13. The method of claim 12, wherein the cancer is breast cancer.

14. A method of inducing Cdc20 degradation in a cell, the method comprising contacting the cell with an effective amount of the compound of claim 1.

15. A method of blocking mitotic progression in a subject, the method comprising administering to the subject a therapeutically effective amount of the compound of claim 1.

16. A method of inhibiting tumor proliferation in a subject, the method comprising administering to the subject a therapeutically effective amount of the compound of claim 1.

17. A method of re-sensitizing a subject to cancer treatment with tamoxifen, the method comprising administering to the subject a therapeutically effective amount of the compound of claim 1, wherein the subject is resistant to treatment with tamoxifen prior to administration of the compound of claim 1.

* * * * *